United States Patent
Conway et al.

(10) Patent No.: US 11,512,287 B2
(45) Date of Patent: Nov. 29, 2022

(54) TARGETED DISRUPTION OF T CELL AND/OR HLA RECEPTORS

(71) Applicant: Sangamo Therapeutics, Inc., Richmond, CA (US)

(72) Inventors: Anthony Conway, Richmond, CA (US); Sumiti Jain, Richmond, CA (US); Gary K. Lee, Richmond, CA (US); David Paschon, Richmond, CA (US); Edward J. Rebar, Richmond, CA (US); Lei Zhang, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 574 days.

(21) Appl. No.: 16/009,975

(22) Filed: Jun. 15, 2018

(65) Prior Publication Data

US 2018/0362926 A1  Dec. 20, 2018

Related U.S. Application Data

(60) Provisional application No. 62/573,956, filed on Oct. 18, 2017, provisional application No. 62/542,052, filed on Aug. 7, 2017, provisional application No. 61/521,132, filed on Jun. 16, 2017.

(51) Int. Cl.
| | |
|---|---|
| C12N 9/22 | (2006.01) |
| C12N 5/0789 | (2010.01) |
| C07K 19/00 | (2006.01) |
| C07K 14/00 | (2006.01) |
| A61K 38/46 | (2006.01) |
| C12N 5/0783 | (2010.01) |
| C12N 15/85 | (2006.01) |
| C07K 14/725 | (2006.01) |
| A61P 37/06 | (2006.01) |
| A61K 48/00 | (2006.01) |
| A61P 35/00 | (2006.01) |
| C12N 15/90 | (2006.01) |
| C07K 14/74 | (2006.01) |

(52) U.S. Cl.
CPC ........ *C12N 5/0636* (2013.01); *A61K 48/0066* (2013.01); *A61P 35/00* (2018.01); *A61P 37/06* (2018.01); *C07K 14/7051* (2013.01); *C12N 9/22* (2013.01); *C12N 15/8509* (2013.01); *C12N 15/907* (2013.01); *A61K 48/005* (2013.01); *C07K 14/70539* (2013.01); *C12N 2015/8518* (2013.01); *C12N 2501/515* (2013.01); *C12N 2510/00* (2013.01); *C12N 2750/14143* (2013.01)

(58) Field of Classification Search
None
See application file for complete search history.

(56) References Cited

U.S. PATENT DOCUMENTS

| | | |
|---|---|---|
| 5,789,538 A | 8/1998 | Rebar et al. |
| 5,925,523 A | 7/1999 | Dove et al. |
| 5,928,638 A | 7/1999 | Uchida et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,723,551 B2 | 4/2004 | Kotin et al. |
| 6,794,136 B1 | 9/2004 | Eisenberg et al. |
| 6,824,978 B1 | 11/2004 | Cox, III et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,053,264 B2 | 5/2006 | Wolffe |
| 7,067,317 B2 | 6/2006 | Rebar et al. |
| 7,070,934 B2 | 7/2006 | Cox, III et al. |

(Continued)

FOREIGN PATENT DOCUMENTS

| | | |
|---|---|---|
| GB | WO 2338237 A | 12/1999 |
| WO | WO 95/19431 A1 | 7/1995 |

(Continued)

OTHER PUBLICATIONS

Ren et al, Multiplex genome editing to generate universal CAR T cells resistant to PD1 inhibition, 2016, AACR, pp. 2255-2266.*

(Continued)

*Primary Examiner* — Maria Marvich
(74) *Attorney, Agent, or Firm* — Foley & Lardner LLP

(57) ABSTRACT

Disclosed herein are methods and compositions for inactivating TCR and/or HLA genes, using engineered nucleases comprising at least one DNA binding domain and a cleavage domain or cleavage half-domain in conditions able to preserve cell viability. Polynucleotides encoding nucleases, vectors comprising polynucleotides encoding nucleases and cells comprising polynucleotides encoding nucleases and/or cells comprising nucleases are also provided.

12 Claims, 9 Drawing Sheets

Specification includes a Sequence Listing.

(56) References Cited

U.S. PATENT DOCUMENTS

| | | |
|---|---|---|
| 7,074,596 B2 | 7/2006 | Darzynkiewicz et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,271,002 B2 | 9/2007 | Kotin et al. |
| 7,361,635 B2 | 4/2008 | Miller et al. |
| 7,888,121 B2 | 2/2011 | Urnov et al. |
| 7,914,796 B2 | 3/2011 | Miller et al. |
| 7,951,925 B2 | 5/2011 | Ando et al. |
| 7,972,854 B2 | 7/2011 | Miller et al. |
| 8,034,598 B2 | 10/2011 | Miller |
| 8,110,379 B2 | 2/2012 | DeKelver et al. |
| 8,153,773 B2 | 4/2012 | Jemiely et al. |
| 8,409,861 B2 | 4/2013 | Guschin et al. |
| 8,563,314 B2 | 10/2013 | Gregory et al. |
| 8,586,526 B2 | 11/2013 | Gregory et al. |
| 8,597,912 B2 | 12/2013 | Collingwood et al. |
| 8,623,618 B2 | 1/2014 | Doyon et al. |
| 8,697,359 B1 | 4/2014 | Zhang |
| 8,703,489 B2 | 4/2014 | Wang |
| 8,771,985 B2 | 7/2014 | Cui et al. |
| 8,772,453 B2 | 7/2014 | Paschon et al. |
| 8,945,868 B2 | 2/2015 | Collingwood et al. |
| 8,956,828 B2 | 2/2015 | Bonini et al. |
| 8,962,281 B2 | 2/2015 | Doyon et al. |
| 9,005,973 B2 | 4/2015 | Cost et al. |
| 9,045,763 B2 | 6/2015 | DeKelver et al. |
| 9,200,266 B2 | 12/2015 | Wang |
| 9,255,250 B2 | 2/2016 | Gregory et al. |
| 9,255,259 B2 | 2/2016 | Cost et al. |
| 9,458,205 B2 | 10/2016 | Gregory et al. |
| 9,567,609 B2 | 2/2017 | Paschon et al. |
| 9,937,207 B2 | 4/2018 | Gregory et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2005/0267061 A1 | 12/2005 | Martin |
| 2006/0063231 A1 | 3/2006 | Li et al. |
| 2006/0194211 A1 | 8/2006 | Burczynski et al. |
| 2007/0218528 A1 | 9/2007 | Miller |
| 2008/0131962 A1 | 6/2008 | Miller |
| 2008/0159996 A1 | 7/2008 | Ando et al. |
| 2009/0068164 A1 | 3/2009 | Segal et al. |
| 2009/0136465 A1 | 5/2009 | Merenick et al. |
| 2010/0218264 A1 | 8/2010 | Cui et al. |
| 2011/0126317 A1* | 5/2011 | Vainstein ........... C12N 15/8279 800/280 |
| 2011/0145940 A1 | 6/2011 | Voytas et al. |
| 2011/0201055 A1 | 8/2011 | Doyon et al. |
| 2011/0265198 A1 | 10/2011 | Gregory et al. |
| 2011/0301073 A1 | 12/2011 | Gregory et al. |
| 2012/0017290 A1 | 1/2012 | Cui et al. |
| 2012/0060230 A1 | 3/2012 | Collingwood et al. |
| 2012/0195936 A1 | 8/2012 | Rudolph et al. |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2014/0120622 A1 | 5/2014 | Gregory et al. |
| 2014/0301990 A1 | 10/2014 | Gregory et al. |
| 2014/0308250 A1 | 10/2014 | Handgretinger et al. |
| 2015/0056705 A1 | 2/2015 | Conway et al. |
| 2015/0110762 A1 | 4/2015 | Holmes et al. |
| 2015/0132269 A1 | 5/2015 | Orkin et al. |
| 2015/0139943 A1 | 5/2015 | Campana et al. |
| 2015/0159172 A1 | 6/2015 | Miller et al. |
| 2015/0164954 A1 | 6/2015 | Bonini et al. |
| 2015/0174169 A1 | 6/2015 | Genovese et al. |
| 2016/0326548 A1 | 11/2016 | Cost |
| 2017/0037431 A1* | 2/2017 | Lieber ................. C12N 15/907 |
| 2017/0137845 A1 | 5/2017 | Tan et al. |
| 2017/0152527 A1 | 6/2017 | Paschon et al. |
| 2017/0173080 A1* | 6/2017 | Lee .................... C07K 14/7051 |
| 2017/0196992 A1 | 7/2017 | Holmes et al. |
| 2017/0211075 A1 | 7/2017 | Lee et al. |
| 2017/0218349 A1 | 8/2017 | Miller et al. |
| 2018/0087072 A1 | 3/2018 | Miller et al. |
| 2019/0241877 A1* | 8/2019 | DeKelver ......... C12Y 304/21022 |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/099084 A2 | 12/2002 |
| WO | WO 03/016496 A2 | 2/2003 |
| WO | WO 2010/079430 A1 | 7/2010 |
| WO | 2012127464 A2 | 9/2012 |
| WO | WO 2014/059173 A2 | 4/2014 |
| WO | WO 2014/153470 A2 | 9/2014 |
| WO | WO 2015/136001 A1 | 9/2015 |

OTHER PUBLICATIONS

Beerli, et al., "Engineering Polydactyl Zinc-Finger Transcription Factors," *Nature Biotechnology* 20:135-141 (2002).
Beurdeley, et al., "Compact Designer Talens for Efficient Genome Engineering," *Nat Comm* 4(1762): 1-8, doi:10.1038/ncomms2782 (2013).
Bitinaite, et al., "FokI Dimerization is Required for DNA Cleavage," *Proc. Natl. Acad Sci USA* 95:10,570-10,575 (1998).
Boch, et al., "Breaking the Code of DNA Binding Specificity of Tal-Type III Effectors," *Science* 326:1509-1512 (2009).
Boissel, et al., "Megatals: a Rare-Cleaving Nuclease Architecture for Therapeutic Genome Engineering," *Nucleic Acids Research* 42(4):2591-2601, doi:10.1093/nar/gkt1224 (2013).
Bonas, et al., "Genetic and Structural Characterization of the Avirulence Gene AVRBS3 From Xanthomonas Campestris Pv. Vesicatoria," *Mol Gen Genet* 218:127-136 (1989).
Brady, et al., "Antigen Receptor Allelic Exclusion: an Update and Reappraisal," *J Immunol* 185:3801-3808 (2010).
Chicaybam, et al., "Chimeric Antigen Receptors in Cancer Immuno-Gene Therapy: Current Status and Future Directions," *International Reviews Immunology* 30:294-311 (2011).
Choo, et al., "Advances in Zinc Finger Engineering," *Current Opinion in Structural Biology* 10:411-416 (2000).
Elrod-Erickson, et al., "ZIF268 Protein-DNA Complex Refined At 1.6 Å: A Model System for Understanding Zinc Finger-DNA Interactions," *Structure* 4(10):1171-1180 (1996).
Guilinger, et al., "Fusion of Catalytically Inactive CAS9 To FokI Nuclease Improves the Specificity of Genome Modification," *Nature Biotech.* 32(6):577-582 (2014).
Guilinger, et al., "Broad Specificity Profiling of Talens Results in Engineered Nucleases With Improved DNA Cleavage Specificity," *Nat Methods.* 11(4):429-435 (2014).
Guo, et al., "Directed Evolution of an Enhanced and Highly Efficient FokI Cleavage Domain for Zinc Finger Nucleases," *J. Mol. Biol.* 400(11:96-107 doi.10.1016/j.jmb.2010.04.060 (2010).
Haft, et al., "A Guild Of 45 CRISPR-Associated (CAS) Protein Families and Multiple CRISPR/CAS*Subtypes Exist in Prokaryotic Genomes,"* *PLoS Computational Biology* 1(6)e60:474-483 (2005).
Heuer, et al., "Repeat Domain Diversity of AVRBS3-Like Genes in Ralstonia Solanacearum Strains and Association With Host Preferences in the Field," *Applied and Environmental Microbiology* 73(13):4379-4384 (2007).
Isalan, et al., "A Rapid, Generally Applicable Method To Engineer Zinc Fingers Illustrated By Targeting the HIV-1 Promoter," *Nat Biotechnol.* 19(7):656-660 (2001).

(56) References Cited

OTHER PUBLICATIONS

Jansen, et al., "Identification of Genes That Are Associated With DNA Repeats in Prokaryotes," *Molecular Microbiology* 43(6):1565-1575 (2002).
Kalos, et al., "T Cells With Chimeric Antigen Receptors Have Potent Antitumor Effects and Can Establish Memory in Patirents With Advanced Leukemia," *Science Translational Medicine* 3(95):95ra73 (2011).
Kariko, et al., "Generating the Optimal MRNA for Therapy: HPLC Purification Eliminates Immune Activation and Improves Translation of Nucleoside-Modified, Protein-Encoding MRNA," *Nucleic Acid Research* 39(21):e142, doi.10.1093/nar/gkr695 (2011).
Kay, et al., "A Bacterial Effector Acts as a Plant Transcription Factor and Induces a Cell Size Regulator," *Science* 318:648-651 (2007).
Kleinstiver, et al., "High-Fidelity CRISPR-CAS9 Variants With Undetectable Genome-Wide Off-Targets," *Nature* 529(7587):490-495, doi:10.1038/nature16526 (2016).
Kollmannsperger, et al., "Live-Cell Protein Labelling With Nanometre Precision By Cell Squeezing," *Nature Communications* 7:10372, doi:10.1038/ncomms10372 (2016).
Komor, et al., "Programmable Editing of a Target Base in Genomic DNA Without Double-Stranded DNA Cleavage," *Nature* 533:420-424 (2016).
Kormann, et al., "Expression of Therapeutic Proteins After Delivery of Chemically Modified MRNA in Mice," *Nature Biotechnology* 29(2):154-157 (2011).
Lombardo, et al., "Gene Editing in Human Stem Cells Using Zinc Finger Nucleases and Integrase-Defective Lentiviral Vector Delivery," *Nature Biotechnology* 25(11):1298-1306 (2007).
MacLeod, et al., "Integration of a CD19 CAR Into the TCR Alpha Chain Locus Streamlines Production of Allogeneic Gene-Edited CAR T Cells," *Molecular Therapy* 25(4):949-961 (2017).
Makarova, et al., "A DNA Repair System Specific for Thermophilic Archaea and Bacteria Predicted By Genomic Context Anlysis," *Nucleic Acids Research* 30(2):482-496 (2002).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biology Direct* 1(7):1-26 (2006).
McCaffery, et al., "CRISPR-CAS9 D10A Nickase Target-Specific Fluorescent Labeling of Double Strand DNA for Whole Genome Mapping and Structural Variation Analysis," *Nucleic Acids Res.* 44(2):e11.doi:10.1093/nar/gkv878. (2016).
Moscou, et al., "A Simple Cipher Governs DNA Recognition By Tal Effectors," *Science* 326:1501 (2009).
Olovnikov, et al., "Bacterial Argonaute Samples the Transcriptome To Identify Foreign DNA," *Molecular Cell* 51:594-605 (2013).
Pabo, et al., "Design and Selection of Novel CYS2-HIS2 Zinc Finger Proteins," *Ann. Rev. Biochem.* 70:313-340 (2001).
Pavletich, et al., "Zinc Finger-DNA Recognition: Crystal Structure of a ZIF268-DNA Complex At 2.1 Å," *Science* 252(5007):809-817 (1991).
Ran, et al., "In Vivo Genome Editing Using *Staphylococcus aureus* CAS9," *Nature* 520:186 (2015).
Rosenberg, et al., "Durable Complete Responses in Heavily Pretreated Patients With Metastatic Melanoma Using T-Cell Transfer Immunotherapy," *Clinical Cancer Research* 17(13):4550-4557 (2011).
Schomack, et al., "Gene-For-Gene-Mediated Recognition of Nuclear-Targeted AVRBS3-Like Bacterial Effector Proteins," *Journal of Plant Physiology* 163(3):256-272 (2006).
Scott, et al., "Antibody Therapy of Cancer," *Nat Rev Cancer* 12:278-287 (2012).
Segal, et al., "Custom DNA-Binding Proteins Come of Age: Polydactyl Zinc-Finger Proteins," *Current Opinion Biotechnology* 12:632-637 (2001).
Sheng, et al., "Structure-Based Cleavage Mechanism of Thermus Thermophilus Argonaute DNA Guide Strand-Mediated DNA Target Cleavage," *Proc. Natl. Acad. Sci. U.S.A.* 111(2):652-657 (2014).
Shrout, et al., "$\beta_2$Microglobulin MRNA Expression Levels Are Prognostic for Lymph Node Metastasis in Colorectal Cancer Patients," *British Journal of Cancer* 98(12):1999 (2008).
Slaymaker, et al., "Rationally Engineered CAS9 Nucleases With Improved Specificity," *Science* 351(6268):84-88, doi:10.1126/science.aad5227 (2016).
Smietanski, et al., "Structural Analysis of Human 2'-O-Ribose Methyltransferases Involved in MRNA cap Structure Formation," *Nature Communications* 5:3004 (2014).
Swarts, et al., "DNA-Guided DNA Interference By a Prokaryotic Argonaute," *Nature* 507(7491):258-261 (2014).
Urnov, et al., "Highly Efficient Endogenous Human Gene Correction Using Designed Zinc-Finger Nucleases," *Nature* 435(7042):646-651 (2005).
Vogel, "A Bacterial Seek-And-Destroy System for Foreign DNA," *Science* 344(6187):972-973 (2014).
Wu, et al., "Adoptive T-Cell Therapy Using Autologous Tumor-Infiltrating Lymphocytes for Metastatic Melanoma: Current Status and Future Outlook," *Cancer J* 18(2):160-175 (2012).
Yuan, et al., "Crystal Structure of A. Aeolicus Argonaute, a Site-Specific DNA-Guided Endoribonuclease, Provides Insights Into Risc-Mediated mRNA Cleavage," *Molecular Cell* 19:405-419 (2005).
Cradick, et al., "ZFN-Site Searches Genomes for Zinc Finger Nuclease Target Sites and Off-Target Sites," BMC Bioinformatics, vol. 12, No. 152, 10 pgs. (2011).
Cross, et al., "Purification of CPG Islands Using a Methylated DNA Binding Column," Nature Genetics, vol. 6, pp. 236-244 (1994).
Fyodor D. Urnov et al: Genome editing with engineered zinc finger nucleases, Nature Reviews Genetics, vol. 11, No. 9, Sep. 1, 2010 (Sep. 1, 2010), pp. 636-646.

\* cited by examiner

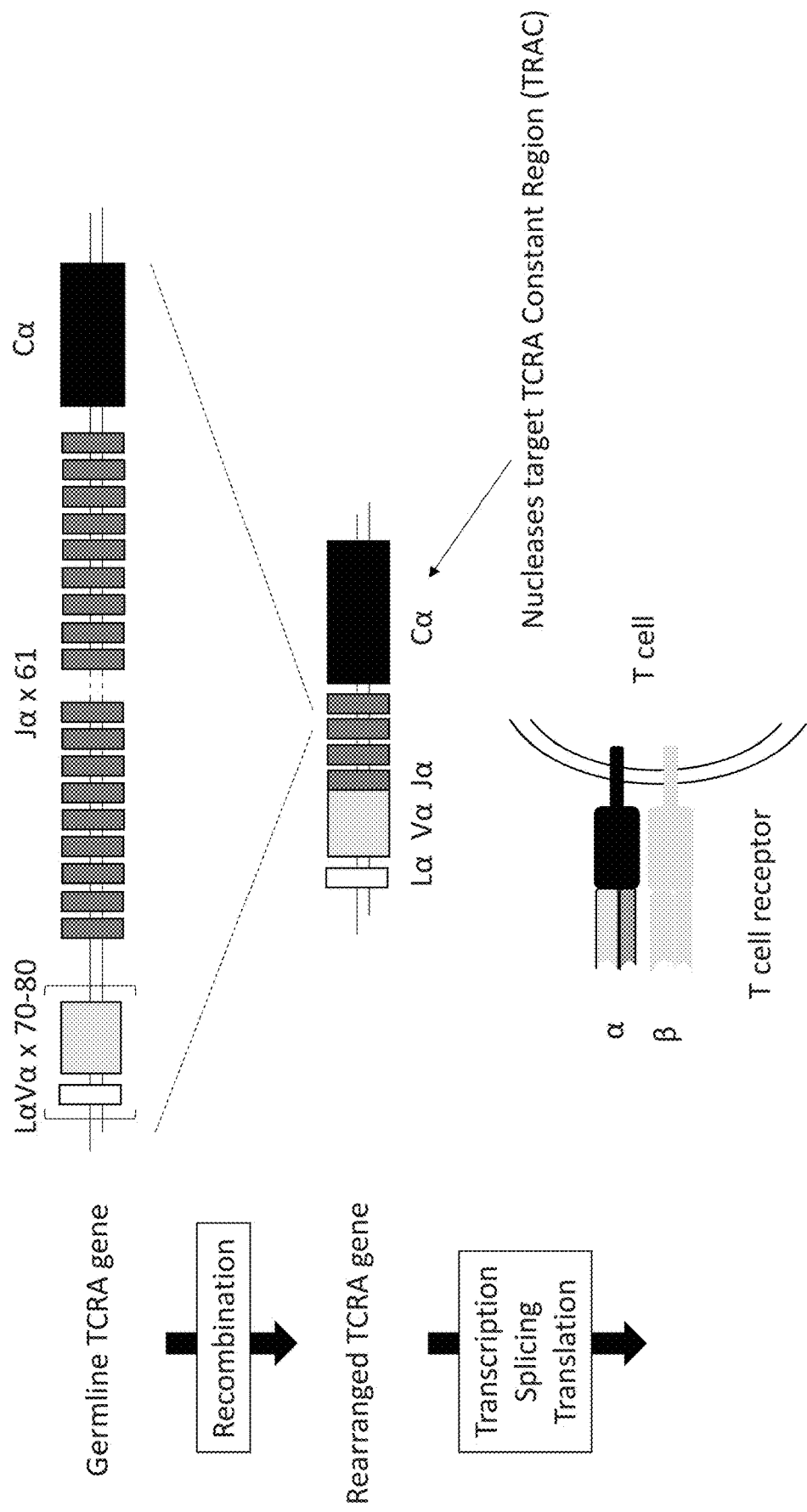

Figure 1B

Exon c1

1 aTATCCAGAACCCTGACCCTGCCCGTGTACCGAGCTGAGAGACTCTAAATCCAGTGACAAGTCTGTCTGCCTATTCACCGATTTTGATTCTCAAACAAATGT

101 GTCACAAAGTAAGGATAAGGATTCTGATGTGTATATCACAGACAAAACTGTGCTAGACATGAGGTCTA[RGGACTT]CAAGAGACT[T]CAAGA[CAGT]CT[GTGGCCTGGAGCAAC
                                                                         F                     A    B

201 AAATCTGACTTTGCATGTGCAAACGCCTTCAACAACAGAGCATTATTCCAGAAGACACCTTCTTCCCCAGCCCA...

Exon c2

2101 ...GAAAGTTCCCTGTGATGTCAAGCTGGTCGAGAAAAAGCT[TTGAAA]CAG...
                                                   E

Exon c3

3021 ...ATACGAAACCTAAACTTTCAAAACCTGTCAGTGATTGGGTTCC[AATC]TC[T]CCTGAAAGTGGCC
                                                      G    D
                                                      Arg       lys

3121 GGGTTTAATCTGCTCATGACGCTGCCGGCTGTGGTCCAGCTGAG...
                       *

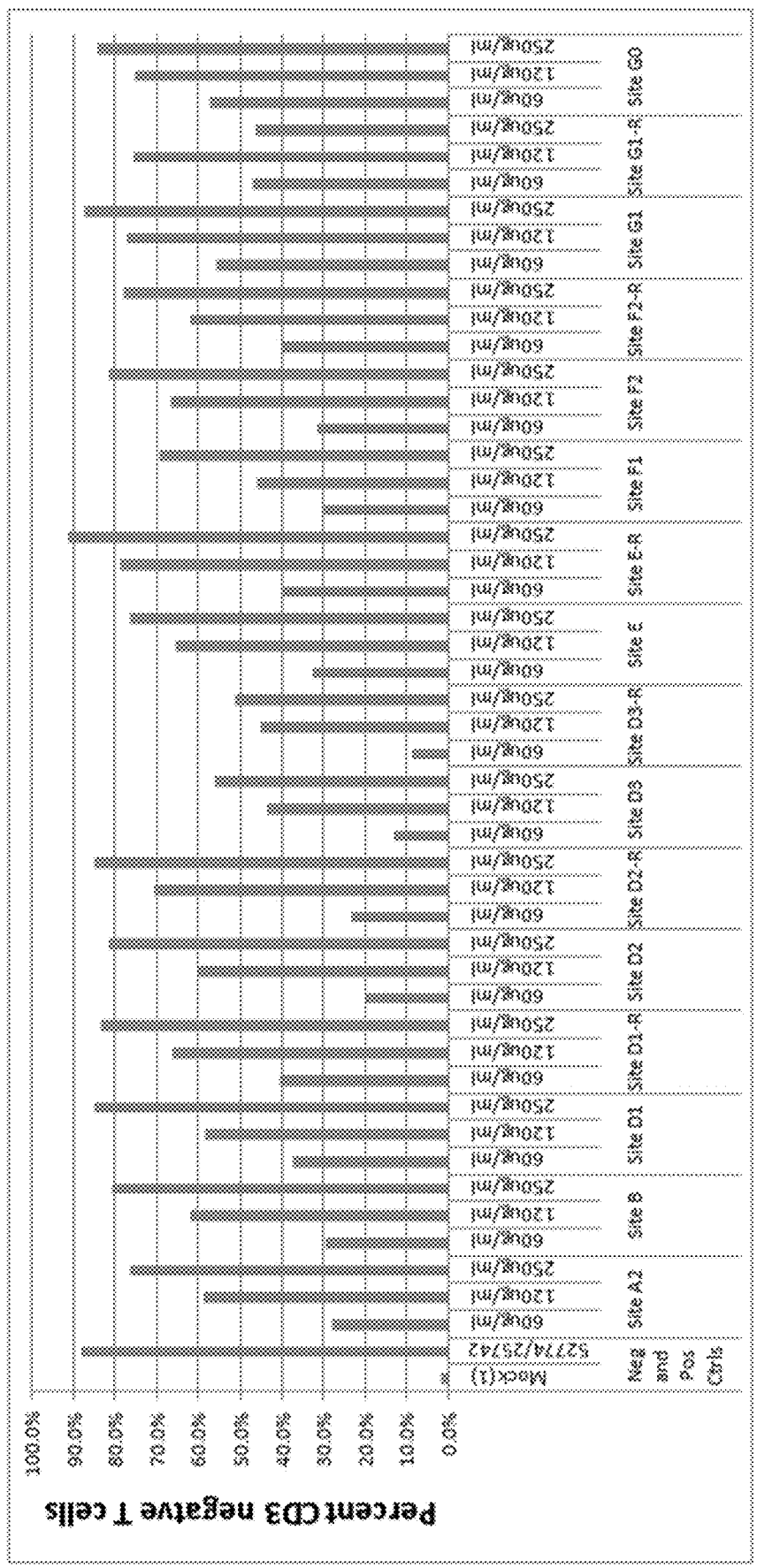

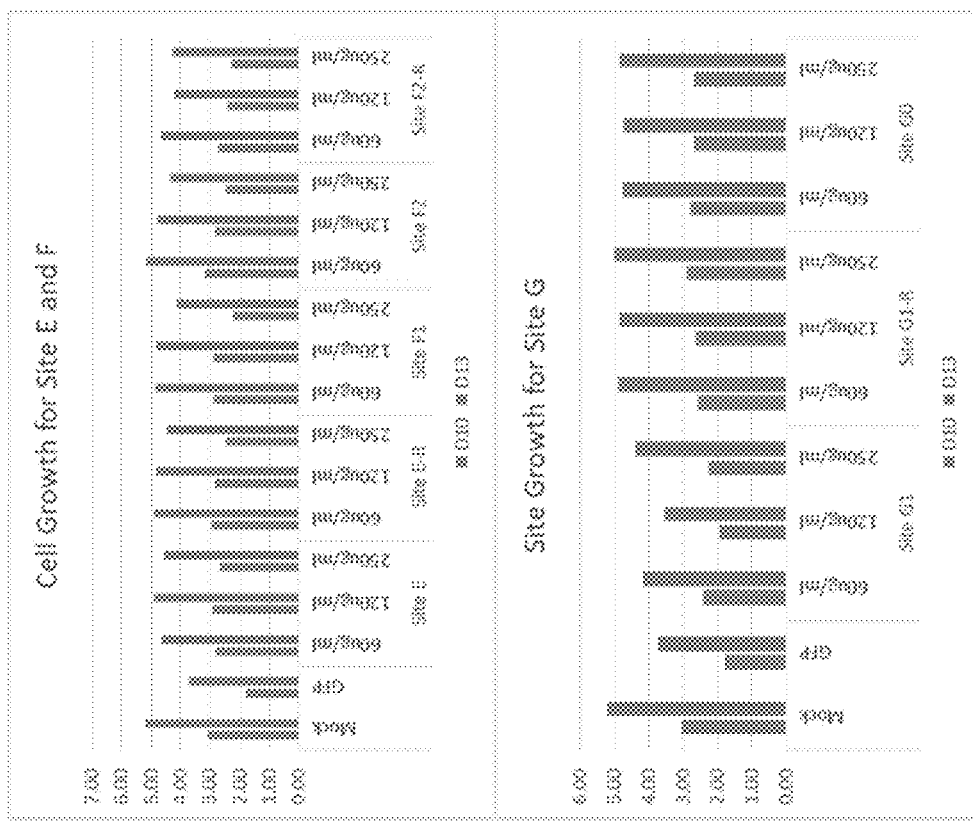
Figure 5A
Figure 5B
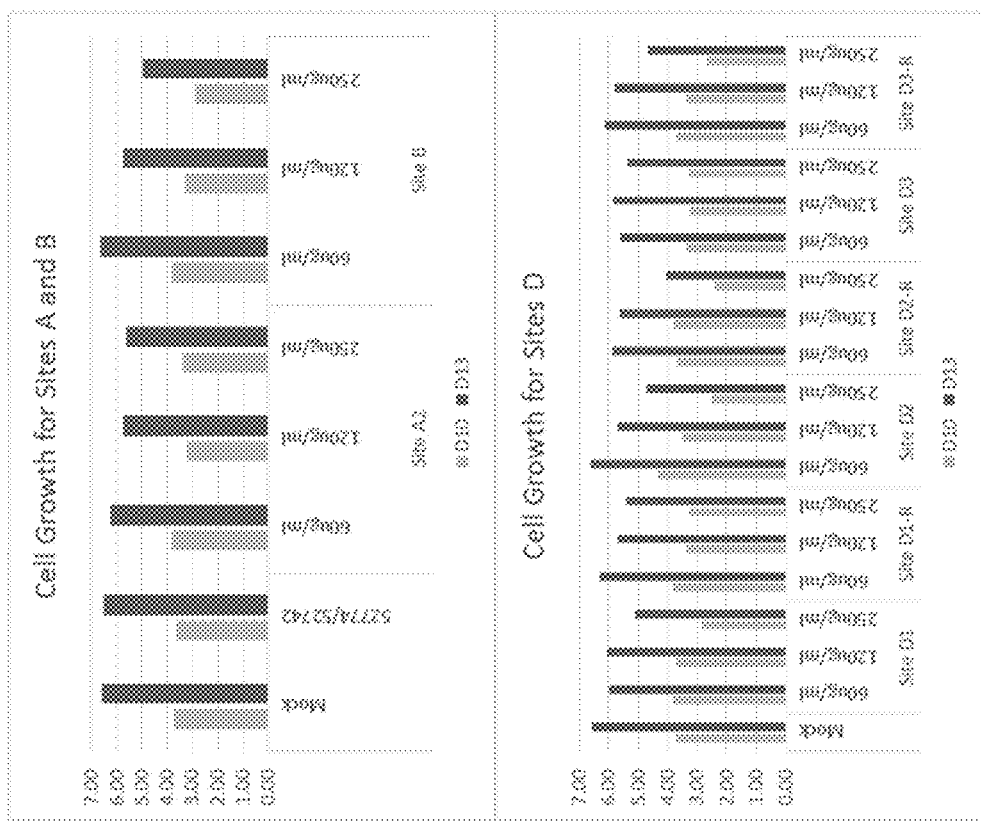
Figure 5C
Figure 5D
Total cell doublings

Figure 6

| ug/mL | FACS D10 | | | | |
|---|---|---|---|---|---|
| | TRAC- | B2M- | DOUBLE- | Total GFP+ | DOUBLE-GFP+ |
| sham | 0.5 | 0.1 | 0.0 | 0.0 | 0.0 |
| TRAC/ B2M KO only | 85.0 | 83.6 | 80.0 | 0.0 | 0.0 |
| TRAC/ B2M KO + 1E5vg/ cell TRAC locus AAV donor | 91.9 | 92.7 | 89.3 | 80.8 | 83.0 |
| TRAC/ B2M KO + 3E4vg/ cell TRAC locus AAV donor | 91.2 | 93.4 | 89.1 | 71.9 | 74.3 |
| TRAC/ B2M KO + 1E5vg/ cell B2M locus AAV donor | 88.2 | 90.5 | 86.4 | 54.9 | 59.6 |
| TRAC/ B2M KO + 3E4vg/ cell B2M locus AAV donor | 89.8 | 92.2 | 87.9 | 43.2 | 46.7 |

```
                       SEQUENCE LISTING

<160> NUMBER OF SEQ ID NOS: 190

<210> SEQ ID NO 1

<400> SEQUENCE: 1

000

<210> SEQ ID NO 2

<400> SEQUENCE: 2

000

<210> SEQ ID NO 3

<400> SEQUENCE: 3
```

000

<210> SEQ ID NO 4

<400> SEQUENCE: 4

000

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Leu Val Lys Ser
1               5

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Gly Thr Pro His Glu Val Gly Val Tyr Thr Leu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Gly Ala Ile Arg Cys His Asp Glu Phe Trp Phe
1               5                   10

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttgctcttga agtccataga cctcatgt                                       28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtgctgtggc ctggagcaac aaatctga                                       28

<210> SEQ ID NO 10

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctgttgctct tgaagtccat agacctca                                              28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctgtggcctg gagcaacaaa tctgactt                                              28

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aggattcgga acccaatcac tg                                                    22

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctcctgaaag tggccgggtt taatctgc                                              28

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aggattcgga acccaatcac tgacaggt                                              28

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tcaagctggt cgagaaaagc tttgaaac                                              28

<210> SEQ ID NO 16
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aacaggtaag acagggtct agcctggg                                              28

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctgtgctaga catgaggtct atggactt                                             28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ttcaagagca acagtgctgt ggcctgga                                             28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cctgtcagtg attgggttcc gaatcctc                                             28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tcctcctgaa agtggccggg tttaatct                                             28

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctgtgctaga catgaggtct atg                                                  23

<210> SEQ ID NO 22
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 22

Asp Arg Ser Asn Leu Ser Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Lys Val Thr Leu Ala Ala
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Arg Ser Ala Leu Ser Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Ser Gly Asn Leu Thr Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Arg Ser Ser Leu Lys Glu
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Gln Asn Val Leu Ile Asn
1               5
```

```
<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Asn Ala Thr Arg Thr Lys
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Ser Gly His Leu Ala Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asn Arg Tyr Asp Leu Met Thr
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ser Asp Ser Leu Leu Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Ser Ser Asp Leu Thr Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 33

Asp Arg Ser Ala Leu Ala Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ser Gly Asn Leu Ala Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

His Arg Ser Thr Leu Gln Gly
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ser Gly Asp Leu Thr Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Ser Gly Ser Leu Thr Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln His Gln Val Leu Val Arg
1               5

<210> SEQ ID NO 39
<211> LENGTH: 7
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ser Gly His Leu Ser Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Arg Ser Asp Leu Ser Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ser Asp Ala Leu Ala Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Gln Ser Asn Leu Arg Ala
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Ser Ser Asn Arg Lys Thr
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Ser Ser Thr Arg Lys Thr

```
<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ser Asp Asp Leu Ser Glu
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Asn Ser Asn Arg Lys Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ser Asp His Leu Ser Thr
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Arg Ser His Leu Ala Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Lys Gln His Leu Asn Glu
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 50

His Arg Thr Ser Leu Thr Asp
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Gln Gln Thr Leu Ala Asp
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Arg Glu Asp Leu Ile Thr
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Ser Ser Asn Leu Ser Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

His Asn Ser Ser Leu Lys Asp
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Asn His His Leu Gln Gln
1               5

<210> SEQ ID NO 56
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His Lys Thr Ser Leu Lys Asp
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Ser Ser Asp Leu Ser Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Ser Gly Asn Arg Thr Thr
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Ser Ala Asn Leu Ala Arg
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Ser Asp Val Leu Ser Glu
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61
```

```
Lys His Ser Thr Arg Arg Val
1               5
```

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Thr Met His Gln Arg Val Glu
1               5
```

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Thr Ser Gly His Leu Ser Arg
1               5
```

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Arg Ser Asp His Leu Thr Gln
1               5
```

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Asp Ser Ala Asn Leu Ser Arg
1               5
```

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Gln Ser Gly Ser Leu Thr Arg
1               5
```

<210> SEQ ID NO 67
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 67

Ala Lys Trp Asn Leu Asp Ala
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Asn Asp Ser Leu Lys Thr
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Ser Ser Asn Leu Ser Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Lys Ala Thr Arg Thr Thr
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Ser Ser Asn Arg Thr Lys
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Asn Ala Ser Arg Thr Arg
1               5
```

```
<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Ser Ser Asp Leu Arg Arg
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Ser Asp Asn Leu Ser Glu
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Arg Ala Asn Arg Asn Ser
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Ser Asp Asn Leu Ala Arg
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Lys Val Asn Leu Met Ser
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78
```

```
Gln Lys Val Asn Leu Arg Glu
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Ser Asp Thr Leu Ser Gln
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Lys Gln Thr Arg Thr Thr
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

His Arg Ser Ser Leu Arg Arg
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Ser Ala Asn Leu Ser Arg
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Trp His Ser Ser Leu Arg Val
1               5

<210> SEQ ID NO 84
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 84

Arg Ser Ala His Leu Ser Arg
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Ser Asp Val Leu Ser Val
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Asn Asn His Arg Ile Thr
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Pro Ser Ser Arg Arg Thr
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Ser Asp Ser Leu Ser Val
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Asn Ala Asn Arg Lys Thr
1               5
```

```
<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Ser Asp Ser Leu Ser Thr
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asp Arg Ala Asn Arg Ile Lys
1               5

<210> SEQ ID NO 92
<211> LENGTH: 23
<212> TYPE: DNA
<213> ORGANISM: Homo sapiens

<400> SEQUENCE: 92
gctggtacac ggcagggtca ggg                                              23

<210> SEQ ID NO 93
<211> LENGTH: 23
<212> TYPE: DNA
<213> ORGANISM: Homo sapiens

<400> SEQUENCE: 93
agagtctctc agctggtaca cgg                                              23

<210> SEQ ID NO 94
<211> LENGTH: 23
<212> TYPE: DNA
<213> ORGANISM: Homo sapiens

<400> SEQUENCE: 94
gagaatcaaa atcggtgaat agg                                              23

<210> SEQ ID NO 95
<211> LENGTH: 23
<212> TYPE: DNA
<213> ORGANISM: Homo sapiens

<400> SEQUENCE: 95
acaaaactgt gctagacatg agg                                              23

<210> SEQ ID NO 96
<211> LENGTH: 23
<212> TYPE: DNA
<213> ORGANISM: Homo sapiens

<400> SEQUENCE: 96
agagcaacag tgctgtggcc tgg                                              23
```

```
<210> SEQ ID NO 97
<211> LENGTH: 23
<212> TYPE: DNA
<213> ORGANISM: Homo sapiens

<400> SEQUENCE: 97
gacaccttct tccccagccc agg                                              23

<210> SEQ ID NO 98
<211> LENGTH: 23
<212> TYPE: DNA
<213> ORGANISM: Homo sapiens

<400> SEQUENCE: 98
ctcgaccagc ttgacatcac agg                                              23

<210> SEQ ID NO 99
<211> LENGTH: 23
<212> TYPE: DNA
<213> ORGANISM: Homo sapiens

<400> SEQUENCE: 99
aagttcctgt gatgtcaagc tgg                                              23

<210> SEQ ID NO 100
<211> LENGTH: 23
<212> TYPE: DNA
<213> ORGANISM: Homo sapiens

<400> SEQUENCE: 100
gtcgagaaaa gctttgaaac agg                                              23

<210> SEQ ID NO 101
<211> LENGTH: 23
<212> TYPE: DNA
<213> ORGANISM: Homo sapiens

<400> SEQUENCE: 101
ttcggaaccc aatcactgac agg                                              23

<210> SEQ ID NO 102
<211> LENGTH: 23
<212> TYPE: DNA
<213> ORGANISM: Homo sapiens

<400> SEQUENCE: 102
ccactttcag gaggaggatt cgg                                              23

<210> SEQ ID NO 103
<211> LENGTH: 23
<212> TYPE: DNA
<213> ORGANISM: Homo sapiens

<400> SEQUENCE: 103
acccggccac tttcaggagg agg                                              23

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
```
gctggtacac ggcagggtca                                              20

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gagagtctct cagctggtac a                                            21

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gagaatcaaa atcggtgaat                                              20

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gacaaaactg tgctagacat g                                            21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gagagcaaca gtgctgtggc c                                            21

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gacaccttct tccccagccc                                              20

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gctcgaccag cttgacatca c                                          21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gaagttcctg tgatgtcaag c                                          21

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gtcgagaaaa gctttgaaac                                            20

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gttcggaacc caatcactga c                                          21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gccactttca ggaggaggat t                                          21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gacccggcca ctttcaggag g                                          21

<210> SEQ ID NO 116
<211> LENGTH: 300
<212> TYPE: DNA
<213> ORGANISM: Homo sapiens

<400> SEQUENCE: 116
atatccagaa ccctgaccct gccgtgtacc agctgagaga ctctaaatcc agtgacaagt    60
ctgtctgcct attcaccgat tttgattctc aaacaaatgt gtcacaaagt aaggattctg   120

```
atgtgtatat cacagacaaa actgtgctag acatgaggtc tatggacttc aagagcaaca      180
gtgctgtggc ctggagcaac aaatctgact ttgcatgtgc aaacgccttc aacaacagca      240
ttattccaga agacaccttc ttccccagcc caggtaaggg cagctttggt gccttcgcag      300
```

```
<210> SEQ ID NO 117
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
tgtcggatgg atgaaaccca gacacata                                          28
```

```
<210> SEQ ID NO 118
<211> LENGTH: 160
<212> TYPE: DNA
<213> ORGANISM: Homo sapiens

<400> SEQUENCE: 118
aagcccataa ccgctgtggc ctcttggttt tacagatacg aacctaaact ttcaaaacct       60
gtcagtgatt gggttccgaa tcctcctcct gaaagtggcc gggtttaatc tgctcatgac      120
gctgcggctg tggtccagct gaggtgaggg gccttgaagc                            160
```

```
<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Gln His Val Leu Gln Asn
1               5
```

```
<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Ser Lys Thr Arg Thr Asn
1               5
```

```
<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Thr Glu Asp Arg Leu Ala
1               5
```

```
<210> SEQ ID NO 122
<211> LENGTH: 9
<212> TYPE: PRT
```

```
<213> ORGANISM: Unknown
<220> FEATURE:
<223> OTHER INFORMATION: Description of Unknown:
      "LAGLIDADG" family peptide motif sequence

<400> SEQUENCE: 122

Leu Ala Gly Leu Ile Asp Ala Asp Gly
1               5

<210> SEQ ID NO 123
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tagcaattca ggaaatttga ctttccat                                      28

<210> SEQ ID NO 124

<400> SEQUENCE: 124

000

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Arg Trp Tyr Leu Asp Lys
1               5

<210> SEQ ID NO 126
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gagtagcgcg agcacagcta aggccacg                                      28

<210> SEQ ID NO 127
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gccacggagc gagacatctc ggcccgaa                                      28

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 128

Ala Gln Cys Cys Leu Phe His
1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Arg Ser Ala Asn Leu Thr Arg
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Arg Ser Asp Asp Leu Thr Arg
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Arg Ser Asp Asp Leu Ser Lys
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Ser Ser Ala Arg Lys Lys
1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gln Arg Thr His Leu Arg Asp
1               5

<210> SEQ ID NO 134
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 134

Asp Ser Ser Asn Arg Glu Ala
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Leu Arg Gly Ser Gln Leu Val Lys Ser
1               5

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ser Gly Ala Ile Arg Cys His Asp Glu Phe Trp Phe
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Gly Thr Pro His Glu Val Gly Val Tyr Thr Leu
1               5                   10

<210> SEQ ID NO 138
<211> LENGTH: 579
<212> TYPE: PRT
<213> ORGANISM: Unknown
<220> FEATURE:
<223> OTHER INFORMATION: Description of Unknown:
      FokI protein sequence

<400> SEQUENCE: 138

Met Val Ser Lys Ile Arg Thr Phe Gly Trp Val Gln Asn Pro Gly Lys
1               5                   10                  15

Phe Glu Asn Leu Lys Arg Val Val Gln Val Phe Asp Arg Asn Ser Lys
            20                  25                  30

Val His Asn Glu Val Lys Asn Ile Lys Ile Pro Thr Leu Val Lys Glu
        35                  40                  45

Ser Lys Ile Gln Lys Glu Leu Val Ala Ile Met Asn Gln His Asp Leu
    50                  55                  60

Ile Tyr Thr Tyr Lys Glu Leu Val Gly Thr Gly Thr Ser Ile Arg Ser
65                  70                  75                  80

Glu Ala Pro Cys Asp Ala Ile Ile Gln Ala Thr Ile Ala Asp Gln Gly
```

```
                        85                  90                  95
Asn Lys Lys Gly Tyr Ile Asp Asn Trp Ser Ser Asp Gly Phe Leu Arg
            100                 105                 110

Trp Ala His Ala Leu Gly Phe Ile Glu Tyr Ile Asn Lys Ser Asp Ser
            115                 120                 125

Phe Val Ile Thr Asp Val Gly Leu Ala Tyr Ser Lys Ser Ala Asp Gly
            130                 135                 140

Ser Ala Ile Glu Lys Glu Ile Leu Ile Glu Ala Ile Ser Ser Tyr Pro
145                 150                 155                 160

Pro Ala Ile Arg Ile Leu Thr Leu Leu Glu Asp Gly Gln His Leu Thr
            165                 170                 175

Lys Phe Asp Leu Gly Lys Asn Leu Gly Phe Ser Gly Glu Ser Gly Phe
            180                 185                 190

Thr Ser Leu Pro Glu Gly Ile Leu Leu Asp Thr Leu Ala Asn Ala Met
            195                 200                 205

Pro Lys Asp Lys Gly Glu Ile Arg Asn Asn Trp Glu Gly Ser Ser Asp
            210                 215                 220

Lys Tyr Ala Arg Met Ile Gly Gly Trp Leu Asp Lys Leu Gly Leu Val
225                 230                 235                 240

Lys Gln Gly Lys Lys Glu Phe Ile Ile Pro Thr Leu Gly Lys Pro Asp
            245                 250                 255

Asn Lys Glu Phe Ile Ser His Ala Phe Lys Ile Thr Gly Glu Gly Leu
            260                 265                 270

Lys Val Leu Arg Arg Ala Lys Gly Ser Thr Lys Phe Thr Arg Val Pro
            275                 280                 285

Lys Arg Val Tyr Trp Glu Met Leu Ala Thr Asn Leu Thr Asp Lys Glu
            290                 295                 300

Tyr Val Arg Thr Arg Arg Ala Leu Ile Leu Glu Ile Leu Ile Lys Ala
305                 310                 315                 320

Gly Ser Leu Lys Ile Glu Gln Ile Gln Asp Asn Leu Lys Lys Leu Gly
            325                 330                 335

Phe Asp Glu Val Ile Glu Thr Ile Glu Asn Asp Ile Lys Gly Leu Ile
            340                 345                 350

Asn Thr Gly Ile Phe Ile Glu Ile Lys Gly Arg Phe Tyr Gln Leu Lys
            355                 360                 365

Asp His Ile Leu Gln Phe Val Ile Pro Asn Arg Gly Val Thr Lys Gln
            370                 375                 380

Leu Val Lys Ser Glu Leu Glu Glu Lys Lys Ser Glu Leu Arg His Lys
385                 390                 395                 400

Leu Lys Tyr Val Pro His Glu Tyr Ile Glu Leu Ile Glu Ile Ala Arg
            405                 410                 415

Asn Ser Thr Gln Asp Arg Ile Leu Glu Met Lys Val Met Glu Phe Phe
            420                 425                 430

Met Lys Val Tyr Gly Tyr Arg Gly Lys His Leu Gly Gly Ser Arg Lys
            435                 440                 445

Pro Asp Gly Ala Ile Tyr Thr Val Gly Ser Pro Ile Asp Tyr Gly Val
            450                 455                 460

Ile Val Asp Thr Lys Ala Tyr Ser Gly Gly Tyr Asn Leu Pro Ile Gly
465                 470                 475                 480

Gln Ala Asp Glu Met Gln Arg Tyr Val Glu Glu Asn Gln Thr Arg Asn
            485                 490                 495

Lys His Ile Asn Pro Asn Glu Trp Trp Lys Val Tyr Pro Ser Ser Val
            500                 505                 510
```

```
Thr Glu Phe Lys Phe Leu Phe Val Ser Gly His Phe Lys Gly Asn Tyr
        515                 520                 525

Lys Ala Gln Leu Thr Arg Leu Asn His Ile Thr Asn Cys Asn Gly Ala
        530                 535                 540

Val Leu Ser Val Glu Glu Leu Leu Ile Gly Gly Glu Met Ile Lys Ala
545                 550                 555                 560

Gly Thr Leu Thr Leu Glu Glu Val Arg Arg Lys Phe Asn Asn Gly Glu
                565                 570                 575

Ile Asn Phe

<210> SEQ ID NO 139
<211> LENGTH: 196
<212> TYPE: PRT
<213> ORGANISM: Unknown
<220> FEATURE:
<223> OTHER INFORMATION: Description of Unknown:
      FokI cleavage domain

<400> SEQUENCE: 139

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
        50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195

<210> SEQ ID NO 140
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Leu Val Lys Ser Glu Leu Glu Glu Lys Lys Ser Glu Leu Arg His
1               5                   10                  15
```

```
Lys Leu Lys Tyr Val Pro His Glu Tyr Ile Glu Leu Ile Glu Ile Ala
            20                  25                  30

Arg Asn Pro Thr Gln Asp Arg Ile Leu Glu Met Lys Val Met Glu Phe
        35                  40                  45

Phe Met Lys Val Tyr Gly Tyr Arg Gly Glu His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
                100                 105                 110

Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
                180                 185                 190

Glu Ile Asn Phe
            195

<210> SEQ ID NO 141
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
                100                 105                 110

Asp Lys His Leu Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175
```

```
Ala Gly Thr Leu Thr Leu Glu Glu Val Arg Arg Lys Phe Asn Asn Gly
            180                 185                 190

Glu Ile Asn Phe
        195

<210> SEQ ID NO 142
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Pro Thr Gln Asp Arg Ile Leu Glu Met Lys Val Met Glu Phe
        35                  40                  45

Phe Met Lys Val Tyr Gly Tyr Arg Gly Glu His Leu Gly Gly Ser Arg
50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
            100                 105                 110

Asp Lys His Leu Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 143
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Glu Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
50                  55                  60
```

```
Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Tyr Asn Leu Pro Ile
                 85                  90                  95

Gly Gln Ala Asp Glu Met Glu Arg Tyr Val Glu Asn Gln Thr Arg
            100                 105                 110

Asp Lys His Leu Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 144
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Leu Val Lys Ser Glu Leu Glu Glu Lys Ser Glu Leu Arg His
 1               5                  10                  15

Lys Leu Lys Tyr Val Pro His Glu Tyr Ile Glu Leu Ile Glu Ile Ala
                 20                  25                  30

Glu Asn Pro Thr Gln Asp Arg Ile Leu Glu Met Lys Val Met Glu Phe
             35                  40                  45

Phe Met Lys Val Tyr Gly Tyr Arg Gly Glu His Leu Gly Gly Ser Arg
 50                  55                  60

Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Tyr Asn Leu Pro Ile
                 85                  90                  95

Gly Gln Ala Asp Glu Met Glu Arg Tyr Val Glu Asn Gln Thr Arg
            100                 105                 110

Asp Lys His Leu Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195
```

```
<210> SEQ ID NO 145
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Tyr Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
            100                 105                 110

Asp Lys His Leu Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 146
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Tyr Asn Pro Thr Gln Asp Arg Ile Leu Glu Met Lys Val Met Glu Phe
        35                  40                  45

Phe Met Lys Val Tyr Gly Tyr Arg Gly Glu His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
```

100                 105                 110

Asp Lys His Leu Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 147
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Glu Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
            100                 105                 110

Asp Lys His Leu Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 148
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 148

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Glu Thr Gln Asp Arg Ile Leu Glu Met Lys Val Met Glu Phe
        35                  40                  45

Phe Met Lys Val Tyr Gly Tyr Arg Gly Glu His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
            100                 105                 110

Asp Lys His Leu Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195

<210> SEQ ID NO 149
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
            100                 105                 110

Asp Lys His Leu Asn Pro Asn Glu Trp Trp Lys Val Tyr Pro Ser Ser
        115                 120                 125

Val Thr Glu Phe Lys Phe Leu Phe Val Ser Gly His Phe Ser Gly Asn
130                 135                 140
```

-continued

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
            165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 150
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Pro Thr Gln Asp Arg Ile Leu Glu Met Lys Val Met Glu Phe
        35                  40                  45

Phe Met Lys Val Tyr Gly Tyr Arg Gly Glu His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
            100                 105                 110

Asp Lys His Leu Asn Pro Asn Glu Trp Trp Lys Val Tyr Pro Ser Ser
        115                 120                 125

Val Thr Glu Phe Lys Phe Leu Phe Val Ser Gly His Phe Ser Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
            165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 151
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

```
Arg Asn Ser Thr Gln Asp Arg Ile Leu Glu Met Lys Val Met Glu Phe
         35                  40                  45

Phe Met Lys Val Tyr Gly Tyr Arg Gly Lys His Leu Gly Gly Ser Arg
 50                  55                  60

Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Gly Tyr Asn Leu Pro Thr
                 85                  90                  95

Gly Gln Ala Asp Glu Met Glu Arg Tyr Val Glu Glu Asn Gln Thr Arg
                100                 105                 110

Asp Lys His Leu Asn Pro Asn Glu Trp Trp Lys Val Tyr Pro Ser Ser
                115                 120                 125

Val Thr Glu Phe Lys Phe Leu Phe Val Ser Gly His Phe Lys Gly Asn
130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
                180                 185                 190

Glu Ile Asn Phe
            195

<210> SEQ ID NO 152
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Leu Val Lys Ser Glu Leu Glu Glu Lys Lys Ser Glu Leu Arg His
 1               5                  10                  15

Lys Leu Lys Tyr Val Pro His Glu Tyr Ile Glu Leu Ile Glu Ile Ala
                 20                  25                  30

Arg Asn Pro Thr Gln Asp Arg Ile Leu Glu Met Lys Val Met Glu Phe
         35                  40                  45

Phe Met Lys Val Tyr Gly Tyr Arg Gly Glu His Leu Gly Gly Ser Arg
 50                  55                  60

Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Gly Tyr Asn Leu Pro Thr
                 85                  90                  95

Gly Gln Ala Asp Glu Met Glu Arg Tyr Val Glu Glu Asn Gln Thr Arg
                100                 105                 110

Asp Lys His Leu Asn Pro Asn Glu Trp Trp Lys Val Tyr Pro Ser Ser
                115                 120                 125

Val Thr Glu Phe Lys Phe Leu Phe Val Ser Gly His Phe Lys Gly Asn
130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
                180                 185                 190
```

```
Glu Ile Asn Phe
        195

<210> SEQ ID NO 153
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
        50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Asp Ile
                85                  90                  95

Gly Gln Ala Asp Glu Met Glu Arg Tyr Val Glu Glu Asn Gln Thr Arg
            100                 105                 110

Asp Lys His Leu Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 154
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Pro Thr Gln Asp Arg Ile Leu Glu Met Lys Val Met Glu Phe
            35                  40                  45

Phe Met Lys Val Tyr Gly Tyr Arg Gly Glu His Leu Gly Gly Ser Arg
        50                  55                  60

Lys Pro Asp Gly Ala Ile Tyr Thr Val Gly Ser Pro Ile Asp Tyr Gly
65                  70                  75                  80
```

```
Val Ile Val Asp Thr Lys Ala Tyr Ser Gly Gly Tyr Asn Leu Asp Ile
                85                  90                  95

Gly Gln Ala Asp Glu Met Glu Arg Tyr Val Glu Asn Gln Thr Arg
            100                 105                 110

Asp Lys His Leu Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 155
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Asp Ala Asp Glu Met Glu Arg Tyr Val Glu Asn Gln Thr Arg
            100                 105                 110

Asp Lys His Leu Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 156
<211> LENGTH: 196
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 156

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Pro Thr Gln Asp Arg Ile Leu Glu Met Lys Val Met Glu Phe
        35                  40                  45

Phe Met Lys Val Tyr Gly Tyr Arg Gly Glu His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Asp Ala Asp Glu Met Glu Arg Tyr Val Glu Glu Asn Gln Thr Arg
            100                 105                 110

Asp Lys His Leu Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 157
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser 115                 120                 125

Val Thr Glu Phe Lys Phe Leu Phe Val Ser Gly His Phe Lys Gly Asn
            130                 135                 140

Tyr Lys Ala Gln Leu Thr Arg Leu Asn Arg Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 158
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Pro Thr Gln Asp Arg Ile Leu Glu Met Lys Val Met Glu Phe
        35                  40                  45

Phe Met Lys Val Tyr Gly Tyr Arg Gly Glu His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn Arg Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 159
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Gln Leu Val Lys Ser Glu Leu Glu Glu Lys Lys Ser Glu Leu Arg His

```
  1               5                  10                 15
Lys Leu Lys Tyr Val Pro His Glu Tyr Ile Glu Leu Ile Glu Ile Ala
                20                 25                 30

Arg Asn Ser Thr Gln Asp Arg Ile Leu Glu Met Lys Val Met Glu Phe
                35                 40                 45

Phe Met Lys Val Tyr Gly Tyr Arg Gly Lys His Leu Gly Gly Ser Arg
     50                 55                 60

Lys Pro Asp Gly Ala Ile Tyr Thr Val Gly Ser Pro Ile Asp Tyr Gly
 65                 70                 75                 80

Val Ile Val Asp Thr Lys Ala Tyr Ser Gly Gly Tyr Asn Leu Pro Ile
                85                 90                 95

Gly Glu Ala Asp Glu Met Gln Arg Tyr Val Lys Glu Asn Gln Thr Arg
               100                105                110

Asn Lys His Ile Asn Pro Asn Glu Trp Trp Lys Val Tyr Pro Ser Ser
               115                120                125

Val Thr Glu Phe Lys Phe Leu Phe Val Ser Gly His Phe Lys Gly Asn
           130                135                140

Tyr Lys Ala Gln Leu Thr Arg Leu Asn Arg Lys Thr Asn Cys Asn Gly
145                150                155                160

Ala Val Leu Ser Val Glu Glu Leu Leu Ile Gly Gly Glu Met Ile Lys
               165                170                175

Ala Gly Thr Leu Thr Leu Glu Glu Val Arg Arg Lys Phe Asn Asn Gly
               180                185                190

Glu Ile Asn Phe
           195
```

<210> SEQ ID NO 160
<211> LENGTH: 196
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 160

```
Gln Leu Val Lys Ser Glu Leu Glu Glu Lys Lys Ser Glu Leu Arg His
 1               5                  10                 15

Lys Leu Lys Tyr Val Pro His Glu Tyr Ile Glu Leu Ile Glu Ile Ala
                20                 25                 30

Arg Asn Pro Thr Gln Asp Arg Ile Leu Glu Met Lys Val Met Glu Phe
                35                 40                 45

Phe Met Lys Val Tyr Gly Tyr Arg Gly Glu His Leu Gly Gly Ser Arg
     50                 55                 60

Lys Pro Asp Gly Ala Ile Tyr Thr Val Gly Ser Pro Ile Asp Tyr Gly
 65                 70                 75                 80

Val Ile Val Asp Thr Lys Ala Tyr Ser Gly Gly Tyr Asn Leu Pro Ile
                85                 90                 95

Gly Glu Ala Asp Glu Met Gln Arg Tyr Val Lys Glu Asn Gln Thr Arg
               100                105                110

Asn Lys His Ile Asn Pro Asn Glu Trp Trp Lys Val Tyr Pro Ser Ser
               115                120                125

Val Thr Glu Phe Lys Phe Leu Phe Val Ser Gly His Phe Lys Gly Asn
           130                135                140

Tyr Lys Ala Gln Leu Thr Arg Leu Asn Arg Lys Thr Asn Cys Asn Gly
145                150                155                160
```

Ala Val Leu Ser Val Glu Glu Leu Leu Ile Gly Gly Glu Met Ile Lys
            165                 170                 175

Ala Gly Thr Leu Thr Leu Glu Glu Val Arg Arg Lys Phe Asn Asn Gly
        180                 185                 190

Glu Ile Asn Phe
    195

<210> SEQ ID NO 161
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
            20                  25                  30

Glu Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn Arg Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
    195

<210> SEQ ID NO 162
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Glu Asn Pro Thr Gln Asp Arg Ile Leu Glu Met Lys Val Met Glu Phe
        35                  40                  45

```
Phe Met Lys Val Tyr Gly Tyr Arg Gly Glu His Leu Gly Gly Ser Arg
    50                  55                  60
Lys Pro Asp Gly Ala Ile Tyr Thr Val Gly Ser Pro Ile Asp Tyr Gly
65                  70                  75                  80
Val Ile Val Asp Thr Lys Ala Tyr Ser Gly Gly Tyr Asn Leu Pro Ile
                85                  90                  95
Gly Gln Ala Asp Glu Met Gln Arg Tyr Val Lys Glu Asn Gln Thr Arg
            100                 105                 110
Asn Lys His Ile Asn Pro Asn Glu Trp Trp Lys Val Tyr Pro Ser Ser
        115                 120                 125
Val Thr Glu Phe Lys Phe Leu Phe Val Ser Gly His Phe Lys Gly Asn
130                 135                 140
Tyr Lys Ala Gln Leu Thr Arg Leu Asn Arg Lys Thr Asn Cys Asn Gly
145                 150                 155                 160
Ala Val Leu Ser Val Glu Leu Leu Ile Gly Gly Glu Met Ile Lys
                165                 170                 175
Ala Gly Thr Leu Thr Leu Glu Glu Val Arg Arg Lys Phe Asn Asn Gly
            180                 185                 190
Glu Ile Asn Phe
        195

<210> SEQ ID NO 163
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gln Leu Val Lys Ser Glu Leu Glu Glu Lys Lys Ser Glu Leu Arg His
1               5                   10                  15
Lys Leu Lys Tyr Val Pro His Glu Tyr Ile Glu Leu Ile Glu Ile Ala
            20                  25                  30
Arg Asn Ser Thr Gln Asp Arg Ile Leu Glu Met Lys Val Met Glu Phe
        35                  40                  45
Phe Met Lys Val Tyr Gly Tyr Arg Gly Lys His Leu Gly Gly Ser Arg
    50                  55                  60
Lys Pro Asp Gly Ala Ile Tyr Thr Val Gly Ser Pro Ile Asp Tyr Gly
65                  70                  75                  80
Val Ile Val Asp Thr Lys Ala Tyr Ser Gly Gly Tyr Asn Leu Pro Ile
                85                  90                  95
Gly Gln Ala Asp Glu Met Gln Arg Tyr Val Lys Glu Asn Gln Thr Arg
            100                 105                 110
Asn Lys His Ile Asn Pro Asn Glu Trp Trp Lys Val Tyr Pro Ser Ser
        115                 120                 125
Val Thr Glu Phe Lys Phe Leu Phe Val Ser Gly His Phe Ser Gly Asn
130                 135                 140
Tyr Lys Ala Gln Leu Thr Arg Leu Asn Arg Lys Thr Asn Cys Asn Gly
145                 150                 155                 160
Ala Val Leu Ser Val Glu Glu Leu Leu Ile Gly Gly Glu Met Ile Lys
                165                 170                 175
Ala Gly Thr Leu Thr Leu Glu Glu Val Arg Arg Lys Phe Asn Asn Gly
            180                 185                 190
Glu Ile Asn Phe
        195
```

<210> SEQ ID NO 164
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

```
Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Pro Thr Gln Asp Arg Ile Leu Glu Met Lys Val Met Glu Phe
            35                  40                  45

Phe Met Lys Val Tyr Gly Tyr Arg Gly Glu His Leu Gly Gly Ser Arg
        50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Ser Gly Asn
    130                 135                 140

Tyr Lys Ala Gln Leu Thr Arg Leu Asn Arg Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195
```

<210> SEQ ID NO 165
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

```
Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
            20                  25                  30

Tyr Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
        50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95
```

```
Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn Arg Lys Thr Asn Cys Asn Gly
145                 150                 155                 160

Ala Val Leu Ser Val Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 166
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Tyr Asn Pro Thr Gln Asp Arg Ile Leu Glu Met Lys Val Met Glu Phe
        35                  40                  45

Phe Met Lys Val Tyr Gly Tyr Arg Gly Glu His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn Arg Lys Thr Asn Cys Asn Gly
145                 150                 155                 160

Ala Val Leu Ser Val Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 167
<211> LENGTH: 196
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 167

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Thr
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn Arg Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 168
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Pro Thr Gln Asp Arg Ile Leu Glu Met Lys Val Met Glu Phe
            35                  40                  45

Phe Met Lys Val Tyr Gly Tyr Arg Gly Glu His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Thr
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn

```
                    130                 135                 140

Tyr Lys Ala Gln Leu Thr Arg Leu Asn Arg Lys Thr Asn Cys Asn Gly
145                 150                 155                 160

Ala Val Leu Ser Val Glu Glu Leu Leu Ile Gly Gly Glu Met Ile Lys
                    165                 170                 175

Ala Gly Thr Leu Thr Leu Glu Glu Val Arg Arg Lys Phe Asn Asn Gly
                    180                 185                 190

Glu Ile Asn Phe
            195

<210> SEQ ID NO 169
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
        50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Asp Ile
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn Arg Lys Thr Asn Cys Asn Gly
145                 150                 155                 160

Ala Val Leu Ser Val Glu Glu Leu Leu Ile Gly Gly Glu Met Ile Lys
                    165                 170                 175

Ala Gly Thr Leu Thr Leu Glu Glu Val Arg Arg Lys Phe Asn Asn Gly
                    180                 185                 190

Glu Ile Asn Phe
            195

<210> SEQ ID NO 170
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
```

```
            20                  25                  30
Arg Asn Pro Thr Gln Asp Arg Ile Leu Glu Met Lys Val Met Glu Phe
             35                  40                  45

Phe Met Lys Val Tyr Gly Tyr Arg Gly Glu His Leu Gly Gly Ser Arg
 50                  55                  60

Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Gly Tyr Asn Leu Asp Ile
                 85                  90                  95

Gly Gln Ala Asp Glu Met Gln Arg Tyr Val Lys Glu Asn Gln Thr Arg
                100                 105                 110

Asn Lys His Ile Asn Pro Asn Glu Trp Trp Lys Val Tyr Pro Ser Ser
                115                 120                 125

Val Thr Glu Phe Lys Phe Leu Phe Val Ser Gly His Phe Lys Gly Asn
                130                 135                 140

Tyr Lys Ala Gln Leu Thr Arg Leu Asn Arg Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
                180                 185                 190

Glu Ile Asn Phe
            195

<210> SEQ ID NO 171
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Leu Val Lys Ser Glu Leu Glu Glu Lys Lys Ser Glu Leu Arg His
 1               5                  10                  15

Lys Leu Lys Tyr Val Pro His Glu Tyr Ile Glu Leu Ile Glu Ile Ala
                 20                  25                  30

Arg Asn Ser Thr Gln Asp Arg Ile Leu Glu Met Lys Val Met Glu Phe
             35                  40                  45

Phe Met Lys Val Tyr Gly Tyr Arg Gly Lys His Leu Gly Gly Ser Arg
 50                  55                  60

Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Gly Tyr Asn Leu Pro Ile
                 85                  90                  95

Gly Gln Ala Asp Glu Met Gln Asp Tyr Val Glu Glu Asn Gln Thr Arg
                100                 105                 110

Asp Lys His Ala Asn Pro Asn Glu Trp Trp Lys Val Tyr Pro Ser Ser
                115                 120                 125

Val Thr Glu Phe Lys Phe Leu Phe Val Ser Gly His Phe Lys Gly Asn
                130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175
```

Ala Gly Thr Leu Thr Leu Glu Glu Val Arg Arg Lys Phe Asn Asn Gly
            180                 185                 190

Glu Ile Asn Phe
        195

<210> SEQ ID NO 172
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Pro Thr Gln Asp Arg Ile Leu Glu Met Lys Val Met Glu Phe
        35                  40                  45

Phe Met Lys Val Tyr Gly Tyr Arg Gly Glu His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Asp Tyr Val Glu Glu Asn Gln Thr Arg
            100                 105                 110

Asp Lys His Ala Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 173
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

```
Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Gly Tyr Asn Leu Pro Ile
                 85                  90                  95

Gly Gln Ala Arg Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn Arg Val Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 174
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gln Leu Val Lys Ser Glu Leu Glu Glu Lys Ser Glu Leu Arg His
 1               5                  10                  15

Lys Leu Lys Tyr Val Pro His Glu Tyr Ile Glu Leu Ile Glu Ile Ala
                 20                  25                  30

Arg Asn Pro Thr Gln Asp Arg Ile Leu Glu Met Lys Val Met Glu Phe
             35                  40                  45

Phe Met Lys Val Tyr Gly Tyr Arg Gly Glu His Leu Gly Gly Ser Arg
    50                  55                  60

Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Gly Tyr Asn Leu Pro Ile
                 85                  90                  95

Gly Gln Ala Arg Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn Arg Val Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 175
```

```
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Arg Pro Phe Gln Cys Arg Ile Cys Met Arg Asn Phe Ser Arg Ser Asp
1               5                   10                  15

Asp Leu Ser Lys His Ile Arg Thr His Thr Gly Glu Lys Pro Phe Ala
            20                  25                  30

Cys Asp Ile Cys Gly Arg Lys Phe Ala Asp Ser Ser Ala Arg Lys Lys
        35                  40                  45

His Thr Lys Ile His Thr Gly Glu Lys Pro Phe Gln Cys Arg Ile Cys
    50                  55                  60

Met Arg Asn Phe Ser Asp Arg Ser Asn Leu Ser Arg His Ile Arg Thr
65                  70                  75                  80

His Thr Gly Glu Lys Pro Phe Ala Cys Asp Ile Cys Gly Arg Lys Phe
                85                  90                  95

Ala Gln Arg Thr His Leu Arg Asp His Thr Lys Ile His Thr His Pro
            100                 105                 110

Arg Ala Pro Ile Pro Lys Pro Phe Gln Cys Arg Ile Cys Met Arg Asn
        115                 120                 125

Phe Ser Gln Ser Gly His Leu Ala Arg His Ile Arg Thr His Thr Gly
    130                 135                 140

Glu Lys Pro Phe Ala Cys Asp Ile Cys Gly Arg Lys Phe Ala Asp Ser
145                 150                 155                 160

Ser Asn Arg Glu Ala His Thr Lys Ile His
                165                 170

<210> SEQ ID NO 176
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Arg Pro Phe Gln Cys Arg Ile Cys Met Arg Lys Phe Ala Ala Gln Cys
1               5                   10                  15

Cys Leu Phe His His Thr Lys Ile His Thr Gly Glu Lys Pro Phe Gln
            20                  25                  30

Cys Arg Ile Cys Met Arg Asn Phe Ser Asp Gln Ser Asn Leu Arg Ala
        35                  40                  45

His Ile Arg Thr His Thr Gly Glu Lys Pro Phe Ala Cys Asp Ile Cys
    50                  55                  60

Gly Arg Lys Phe Ala Arg Ser Ala Asn Leu Thr Arg His Thr Lys Ile
65                  70                  75                  80

His Thr His Pro Arg Ala Pro Ile Pro Lys Pro Phe Gln Cys Arg Ile
                85                  90                  95

Cys Met Arg Asn Phe Ser Arg Ser Asp Asp Leu Thr Arg His Ile Arg
            100                 105                 110

Thr His Thr Gly Glu Lys Pro Phe Ala Cys Asp Ile Cys Gly Arg Lys
        115                 120                 125

Phe Ala Gln Ser Gly Ser Leu Thr Arg His Thr Lys Ile His
    130                 135                 140
```

```
<210> SEQ ID NO 177
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Arg Pro Phe Gln Cys Arg Ile Cys Met Gln Asn Phe Ser Gln Ser Ser
1               5                   10                  15

Asp Leu Ser Arg His Ile Arg Thr His Thr Gly Glu Lys Pro Phe Ala
            20                  25                  30

Cys Asp Ile Cys Gly Arg Lys Phe Ala Gln Ser Gly Asn Arg Thr Thr
        35                  40                  45

His Thr Lys Ile His Thr His Pro Arg Ala Pro Ile Pro Lys Pro Phe
    50                  55                  60

Gln Cys Arg Ile Cys Met Gln Asn Phe Ser Arg Ser Ala Asn Leu Ala
65                  70                  75                  80

Arg His Ile Arg Thr His Thr Gly Glu Lys Pro Phe Ala Cys Asp Ile
                85                  90                  95

Cys Gly Arg Lys Phe Ala Asp Arg Ser Ala Leu Ala Arg His Thr Lys
            100                 105                 110

Ile His Thr Gly Ser Gln Lys Pro Phe Gln Cys Arg Ile Cys Met Gln
        115                 120                 125

Asn Phe Ser Arg Ser Asp Val Leu Ser Glu His Ile Arg Thr His Thr
    130                 135                 140

Gly Glu Lys Pro Phe Ala Cys Asp Ile Cys Gly Arg Lys Phe Ala Lys
145                 150                 155                 160

His Ser Thr Arg Arg Val His Thr Lys Ile His
                165                 170

<210> SEQ ID NO 178
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Arg Pro Phe Gln Cys Arg Ile Cys Met Arg Asn Phe Ser Thr Met His
1               5                   10                  15

Gln Arg Val Glu His Ile Arg Thr His Thr Gly Glu Lys Pro Phe Ala
            20                  25                  30

Cys Asp Ile Cys Gly Arg Lys Phe Ala Thr Ser Gly His Leu Ser Arg
        35                  40                  45

His Thr Lys Ile His Thr Gly Ser Gln Lys Pro Phe Gln Cys Arg Ile
    50                  55                  60

Cys Met Arg Asn Phe Ser Arg Ser Asp His Leu Thr Gln His Ile Arg
65                  70                  75                  80

Thr His Thr Gly Glu Lys Pro Phe Ala Cys Asp Ile Cys Gly Arg Lys
                85                  90                  95

Phe Ala Asp Ser Ala Asn Leu Ser Arg His Thr Lys Ile His Thr His
            100                 105                 110

Pro Arg Ala Pro Ile Pro Lys Pro Phe Gln Cys Arg Ile Cys Met Arg
        115                 120                 125
```

```
Asn Phe Ser Gln Ser Gly Ser Leu Thr Arg His Ile Arg Thr His Thr
        130                 135                 140
Gly Glu Lys Pro Phe Ala Cys Asp Ile Cys Gly Arg Lys Phe Ala Ala
145                 150                 155                 160
Lys Trp Asn Leu Asp Ala His Thr Lys Ile His
                165                 170

<210> SEQ ID NO 179
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Gly Ala Ile Arg Cys His Asp Glu Phe Trp Phe
1               5                   10

<210> SEQ ID NO 180
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Asp Tyr Lys Asp His Asp Gly Asp Tyr Lys Asp His Asp Ile Asp Tyr
1               5                   10                  15
Lys Asp Asp Asp Asp Lys
            20

<210> SEQ ID NO 181
<211> LENGTH: 7
<212> TYPE: PRT
<213> ORGANISM: Unknown
<220> FEATURE:
<223> OTHER INFORMATION: Description of Unknown:
      Nuclear localization sequence

<400> SEQUENCE: 181

Pro Lys Lys Lys Arg Lys Val
1               5

<210> SEQ ID NO 182
<211> LENGTH: 2601
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 182
atggactaca aagaccatga cggtgattat aaagatcatg acatcgatta caaggatgac      60
gatgacaaga tggccccccaa gaagaagagg aaggtcggca tccacggggt acccgccgct     120
atgggacagc tggtgaagag cgagctggag gagaagaagt ccgagctgcg gcacaagctg     180
aagtacgtgc ccacgagta catcgagctg atcgagatcg ccaggaacag cacccaggac     240
cgcatcctgg agatgaaggt gatggagttc ttcatgaagg tgtacggcta caggggaaag     300
cacctgggcg gaagcagaaa gcctgacggc gccatctata cagtgggcag ccccatcgat     360
tacggcgtga tcgtggacac aaaggcctac agcggcggct acaatctgcc taccggccag     420
```

```
gccgacgaga tggagagata cgtggaggag aaccagaccc gggataagca cctcaacccc      480
aacgagtggt ggaaggtgta ccctagcagc gtgaccgagt tcaagttcct gttcgtgagc      540
ggccacttca agggcaacta caaggcccag ctgaccaggc tgaaccacat caccaactgc      600
aatggcgccg tgctgagcgt ggaggagctg ctgatcggcg cgagatgat caaagccggc       660 accctgacac tggaggaggt gcggcgcaag ttcaacaacg gcgagatcaa cttcagcggc      720
gccatcagat gccacgacga gttctggttc aggcccttcc agtgtcgaat ctgcatgcag      780
aacttcagtc agtcctccga cctgtcccgc cacatccgca cccacaccgg cgagaagcct      840
tttgcctgtg acatttgtgg gaggaaattt gccagtccg gcaaccgcac cacccatacc       900
aagatacaca cgcatcccag ggcacctatt cccaagccct ccagtgtcg aatctgcatg       960 cagaacttca gtcgctccgc caacctggcc cgccacatcc gcacccacac cggcgagaag     1020
ccttttgcct gtgacatttg tgggaggaaa tttgccgacc gctccgccct ggcccgccat     1080
accaagatac acacgggatc tcagaagccc ttccagtgtc gaatctgcat gcagaacttc     1140
agtcgctccg acgtgctgtc cgagcacatc cgcacccaca ccggcgagaa gccttttgcc     1200
tgtgacattt gtgggaggaa atttgccaag cactccaccc gccgcgtgca taccaagata     1260
cacctgcggc agaaggacag atctggcggc ggagagggca gaggaagtct tctaacctgc     1320
ggtgacgtgg aggagaatcc cggccctagg accatggact acaaagacca tgacggtgat     1380
tataaagatc atgacatcga ttacaaggat gacgatgaca agatggcccc caagaagaag     1440
aggaaggtcg gcattcatgg ggtacccgcc gctatggctg agaggccctt ccagtgtcga     1500
atctgcatgc gtaacttcag taccatgcac cagcgcgtgg agcacatccg cacccacacc     1560
ggcgagaagc ctttcgcctg tgacatttgt gggaggaaat ttgccacctc cggccacctg     1620
tcccgccata ccaagataca cacgggcagc caaaagccct ccagtgtcg aatctgcatg     1680 cgtaacttca gtcgctccga ccacctgacc cagcacatcc gcacccacac cggcgagaag     1740
ccttttgcct gtgacatttg tgggaggaaa tttgccgact ccgccaacct gtcccgccat     1800
accaagatac acacgcaccc gcgcgcccg atcccgaagc ccttccagtg tcgaatctgc     1860
atgcgtaact tcagtcagtc cggctccctg acccgccaca tccgcaccca caccggcgag     1920
aagccttttg cctgtgacat tgtgggagg aaatttgccg ccaagtggaa cctggacgcc     1980
cataccaaga tacacctgcg gggatcccag ctggtgaaga gcgagctgga ggagaagaag     2040
tccgagctgc ggcacaagct gaagtacgtg ccccacgagt acatcgagct gatcgagatc     2100
gccaggaaca gcacccagga ccgcatcctg gagatgaagg tgatggagtt cttcatgaag     2160
gtgtacggct acaggggaaa gcacctgggc ggaagcagaa agcctgacgg cgccatctat     2220
acagtgggca gccccatcga ttacggcgtg atcgtggaca caaaggccta cagcggcggc     2280
tacaatctgc ctatcggcca ggccgacgag atgcagagat acgtgaagga gaaccagacc     2340
cggaataagc acatcaaccc caacgagtgg tggaaggtgt accctagcag cgtgaccgag     2400
ttcaagttcc tgttcgtgag cggccacttc aagggcaact acaaggccca gctgaccagg     2460
ctgaaccgca aaaccaactg caatggcgcc gtgctgagcg tggaggagct gctgatcggc     2520
ggcgagatga tcaaagccgg caccctgaca ctggaggagg tgcggcgcaa gttcaacaac     2580
ggcgagatca acttctgata a                                              2601
```

<210> SEQ ID NO 183
<211> LENGTH: 865
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 183

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Met Gly Gln Leu Val Lys Ser Glu
        35                  40                  45

Leu Glu Glu Lys Lys Ser Glu Leu Arg His Lys Leu Lys Tyr Val Pro
50                  55                  60

His Glu Tyr Ile Glu Leu Ile Glu Ile Ala Arg Asn Ser Thr Gln Asp
65                  70                  75                  80

Arg Ile Leu Glu Met Lys Val Met Glu Phe Phe Met Lys Val Tyr Gly
                85                  90                  95

Tyr Arg Gly Lys His Leu Gly Gly Ser Arg Lys Pro Asp Gly Ala Ile
            100                 105                 110

Tyr Thr Val Gly Ser Pro Ile Asp Tyr Gly Val Ile Val Asp Thr Lys
        115                 120                 125

Ala Tyr Ser Gly Gly Tyr Asn Leu Pro Thr Gly Gln Ala Asp Glu Met
130                 135                 140

Glu Arg Tyr Val Glu Glu Asn Gln Thr Arg Asp Lys His Leu Asn Pro
145                 150                 155                 160

Asn Glu Trp Trp Lys Val Tyr Pro Ser Ser Val Thr Glu Phe Lys Phe
                165                 170                 175

Leu Phe Val Ser Gly His Phe Lys Gly Asn Tyr Lys Ala Gln Leu Thr
            180                 185                 190

Arg Leu Asn His Ile Thr Asn Cys Asn Gly Ala Val Leu Ser Val Glu
        195                 200                 205

Glu Leu Leu Ile Gly Gly Glu Met Ile Lys Ala Gly Thr Leu Thr Leu
210                 215                 220

Glu Glu Val Arg Arg Lys Phe Asn Asn Gly Glu Ile Asn Phe Ser Gly
225                 230                 235                 240

Ala Ile Arg Cys His Asp Glu Phe Trp Phe Arg Pro Phe Gln Cys Arg
                245                 250                 255

Ile Cys Met Gln Asn Phe Ser Gln Ser Ser Asp Leu Ser Arg His Ile
            260                 265                 270

Arg Thr His Thr Gly Glu Lys Pro Phe Ala Cys Asp Ile Cys Gly Arg
        275                 280                 285

Lys Phe Ala Gln Ser Gly Asn Arg Thr Thr His Thr Lys Ile His Thr
290                 295                 300

His Pro Arg Ala Pro Ile Pro Lys Pro Phe Gln Cys Arg Ile Cys Met
305                 310                 315                 320

Gln Asn Phe Ser Arg Ser Ala Asn Leu Ala Arg His Ile Arg Thr His
                325                 330                 335

Thr Gly Glu Lys Pro Phe Ala Cys Asp Ile Cys Gly Arg Lys Phe Ala
            340                 345                 350

Asp Arg Ser Ala Leu Ala Arg His Thr Lys Ile His Thr Gly Ser Gln
        355                 360                 365

Lys Pro Phe Gln Cys Arg Ile Cys Met Gln Asn Phe Ser Arg Ser Asp
370                 375                 380

```
Val Leu Ser Glu His Ile Arg Thr His Thr Gly Glu Lys Pro Phe Ala
385                 390                 395                 400

Cys Asp Ile Cys Gly Arg Lys Phe Ala Lys His Ser Thr Arg Arg Val
            405                 410                 415

His Thr Lys Ile His Leu Arg Gln Lys Asp Arg Ser Gly Gly Gly Glu
        420                 425                 430

Gly Arg Gly Ser Leu Leu Thr Cys Gly Asp Val Glu Glu Asn Pro Gly
        435                 440                 445

Pro Arg Thr Met Asp Tyr Lys Asp His Asp Gly Asp Tyr Lys Asp His
    450                 455                 460

Asp Ile Asp Tyr Lys Asp Asp Asp Asp Lys Met Ala Pro Lys Lys Lys
465                 470                 475                 480

Arg Lys Val Gly Ile His Gly Val Pro Ala Ala Met Ala Glu Arg Pro
                485                 490                 495

Phe Gln Cys Arg Ile Cys Met Arg Asn Phe Ser Thr Met His Gln Arg
            500                 505                 510

Val Glu His Ile Arg Thr His Thr Gly Glu Lys Pro Phe Ala Cys Asp
        515                 520                 525

Ile Cys Gly Arg Lys Phe Ala Thr Ser Gly His Leu Ser Arg His Thr
    530                 535                 540

Lys Ile His Thr Gly Ser Gln Lys Pro Phe Gln Cys Arg Ile Cys Met
545                 550                 555                 560

Arg Asn Phe Ser Arg Ser Asp His Leu Thr Gln His Ile Arg Thr His
                565                 570                 575

Thr Gly Glu Lys Pro Phe Ala Cys Asp Ile Cys Gly Arg Lys Phe Ala
            580                 585                 590

Asp Ser Ala Asn Leu Ser Arg His Thr Lys Ile His Thr His Pro Arg
        595                 600                 605

Ala Pro Ile Pro Lys Pro Phe Gln Cys Arg Ile Cys Met Arg Asn Phe
    610                 615                 620

Ser Gln Ser Gly Ser Leu Thr Arg His Ile Arg Thr His Thr Gly Glu
625                 630                 635                 640

Lys Pro Phe Ala Cys Asp Ile Cys Gly Arg Lys Phe Ala Ala Lys Trp
                645                 650                 655

Asn Leu Asp Ala His Thr Lys Ile His Leu Arg Gly Ser Gln Leu Val
            660                 665                 670

Lys Ser Glu Leu Glu Glu Lys Lys Ser Glu Leu Arg His Lys Leu Lys
        675                 680                 685

Tyr Val Pro His Glu Tyr Ile Glu Leu Ile Glu Ile Ala Arg Asn Ser
    690                 695                 700

Thr Gln Asp Arg Ile Leu Glu Met Lys Val Met Glu Phe Phe Met Lys
705                 710                 715                 720

Val Tyr Gly Tyr Arg Gly Lys His Leu Gly Gly Ser Arg Lys Pro Asp
                725                 730                 735

Gly Ala Ile Tyr Thr Val Gly Ser Pro Ile Asp Tyr Gly Val Ile Val
            740                 745                 750

Asp Thr Lys Ala Tyr Ser Gly Gly Tyr Asn Leu Pro Ile Gly Gln Ala
        755                 760                 765

Asp Glu Met Gln Arg Tyr Val Lys Glu Asn Gln Thr Arg Asn Lys His
    770                 775                 780

Ile Asn Pro Asn Glu Trp Trp Lys Val Tyr Pro Ser Ser Val Thr Glu
785                 790                 795                 800

Phe Lys Phe Leu Phe Val Ser Gly His Phe Lys Gly Asn Tyr Lys Ala
```

```
                    805                 810                 815
Gln Leu Thr Arg Leu Asn Arg Lys Thr Asn Cys Asn Gly Ala Val Leu
                820                 825                 830

Ser Val Glu Glu Leu Leu Ile Gly Gly Glu Met Ile Lys Ala Gly Thr
            835                 840                 845

Leu Thr Leu Glu Glu Val Arg Arg Lys Phe Asn Asn Gly Glu Ile Asn
        850                 855                 860

Phe
865

<210> SEQ ID NO 184
<211> LENGTH: 2505
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 184
```

| | | | | | |
|---|---|---|---|---|---|
| atggactaca | aagaccatga | cggtgattat | aaagatcatg | acatcgatta | caaggatgac   60 |
| gatgacaaga | tggcccccaa | gaagaagagg | aaggtcggca | tccacggggt | acccgccgct  120 |
| atggctgaga | ggcccttcca | gtgtcgaatc | tgcatgcgta | acttcagtcg | tagtgacgac  180 |
| ctgagcaagc | acatccgcac | ccacacaggc | gagaagcctt | ttgcctgtga | catttgtggg  240 |
| aggaaatttg | ccgacagcag | cgcccgcaaa | agcataccag | atacacacg | ggcgagaag  300 |
| cccttccagt | gtcgaatctg | catgcgtaac | ttcagtgacc | gctccaacct | gtcccgccac  360 |
| atccgcaccc | acaccggcga | gaagcctttt | gcctgtgaca | tttgtgggag | gaaatttgcc  420 |
| cagcgcaccc | acctgcgcga | ccataccaag | atacacacgc | accgcgcgc | ccgatcccg  480 |
| aagcccttcc | agtgtcgaat | ctgcatgcgt | aacttcagtc | agtccggcca | cctggcccgc  540 |
| cacatccgca | cccacaccgg | cgagaagcct | tttgcctgtg | acatttgtgg | gaggaaattt  600 |
| gccgactcct | ccaaccgcga | ggcccatacc | aagatacacc | tgcggggatc | ccagctggtg  660 |
| aagagcgagc | tggaggagaa | gaagtccgag | ctgcggcaca | agctgaagta | cgtgccccac  720 |
| gagtacatcg | agctgatcga | gatcgccagg | aacagcaccc | aggaccgcat | cctggagatg  780 |
| aaggtgatgg | agttcttcat | gaaggtgtac | ggctacaggg | aaagcacct | gggcggaagc  840 |
| agaaagcctg | acggcgccat | ctatacagtg | gcagcccca | tcgattacgg | cgtgatcgtg  900 |
| gacacaaagg | cctacagcgg | cggctacaat | ctggacatcg | ccaggccga | cgagatggag  960 |
| agatacgtgg | aggagaacca | gacccgggat | aagcacctca | cccccaacga | gtggtggaag 1020 |
| gtgtaccccta | gcagcgtgac | cgagttcaag | ttcctgttcg | tgagcggcca | cttcaagggc 1080 |
| aactacaagg | cccagctgac | caggctgaac | cacatcacca | actgcaatgg | cgccgtgctg 1140 |
| agcgtggagg | agctgctgat | cggcggcgag | atgatcaaag | ccggcaccct | gacactggag 1200 |
| gaggtgcggc | gcaagttcaa | caacggcgag | atcaacttca | gatctggcgg | cggagagggc 1260 |
| agaggaagtc | ttctaacctg | cggtgacgtg | gaggagaatc | ccggccctag | gaccatggac 1320 |
| tacaaagacc | atgacggtga | ttataaagat | catgacatcg | attacaagga | tgacgatgac 1380 |
| aagatggccc | ccaagaagaa | gaggaaggtc | ggcattcatg | ggtacccgc | cgctatggga 1440 |
| cagctggtga | gagcgagct | ggaggagaag | aagtccgagc | tgcggcacaa | gctgaagtac 1500 |
| gtgccccacg | agtacatcga | gctgatcgag | atcgcctaca | acagcaccca | ggaccgcatc 1560 |
| ctggagatga | aggtgatgga | gttcttcatg | aaggtgtacg | gctacagggg | aaagcacctg 1620 |

```
ggcggaagca gaaagcctga cggcgccatc tatacagtgg gcagcccat cgattacggc    1680 gtgatcgtgg acacaaaggc ctacagcggc ggctacaatc tgcctatcgg ccaggccgac   1740
gagatgcaga gatacgtgaa ggagaaccag acccggaata agcacatcaa ccccaacgag   1800
tggtggaagg tgtaccctag cagcgtgacc gagttcaagt tcctgttcgt gagcggccac   1860
ttcaagggca actacaaggc ccagctgacc aggctgaacc gcaaaaccaa ctgcaatggc   1920
gccgtgctga cgtggagga gctgctgatc ggcggcgaga tgatcaaagc cggcacccctg  1980 acactggagg aggtgcggcg caagttcaac aacggcgaga tcaacttcag cggcgctcag   2040
ggatctaccc tggactttag gcccttccag tgtcgaatct gcatgcgtaa gtttgccgcc   2100
cagtgttgtc tgttccacca taccaagata cacacgggcg agaagccctt ccagtgtcga   2160
atctgcatgc gtaacttcag tgaccagtcc aacctgcgcg cccacatccg cacccacacc   2220
ggcgagaagc cttttgcctg tgacatttgt gggaggaaat tgcccgctc cgccaacctg    2280 acccgccata ccaagataca cacgcacccg cgcgccccga tcccgaagcc cttccagtgt   2340
cgaatctgca tgcgtaactt cagtcgctcc gacgacctga cccgccacat ccgcacccac   2400
accggcgaga agccttttgc ctgtgacatt tgtgggagga aatttgccca gtccggctcc   2460
ctgacccgcc ataccaagat acacctgcgg cagaaggact gataa                   2505
```

<210> SEQ ID NO 185
<211> LENGTH: 833
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 185

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Ile His Gly Val Pro Ala Ala Met Ala Glu Arg Pro Phe Gln Cys
        35                  40                  45

Arg Ile Cys Met Arg Asn Phe Ser Arg Ser Asp Asp Leu Ser Lys His
    50                  55                  60

Ile Arg Thr His Thr Gly Glu Lys Pro Phe Ala Cys Asp Ile Cys Gly
65                  70                  75                  80

Arg Lys Phe Ala Asp Ser Ser Ala Arg Lys Lys His Thr Lys Ile His
                85                  90                  95

Thr Gly Glu Lys Pro Phe Gln Cys Arg Ile Cys Met Arg Asn Phe Ser
            100                 105                 110

Asp Arg Ser Asn Leu Ser Arg His Ile Arg Thr His Thr Gly Glu Lys
        115                 120                 125

Pro Phe Ala Cys Asp Ile Cys Gly Arg Lys Phe Ala Gln Arg Thr His
    130                 135                 140

Leu Arg Asp His Thr Lys Ile His Thr His Pro Arg Ala Pro Ile Pro
145                 150                 155                 160

Lys Pro Phe Gln Cys Arg Ile Cys Met Arg Asn Phe Ser Gln Ser Gly
                165                 170                 175

His Leu Ala Arg His Ile Arg Thr His Thr Gly Glu Lys Pro Phe Ala
            180                 185                 190

Cys Asp Ile Cys Gly Arg Lys Phe Ala Asp Ser Ser Asn Arg Glu Ala
        195                 200                 205
```

```
His Thr Lys Ile His Leu Arg Gly Ser Gln Leu Val Lys Ser Glu Leu
        210                 215                 220

Glu Glu Lys Lys Ser Glu Leu Arg His Lys Leu Lys Tyr Val Pro His
225                 230                 235                 240

Glu Tyr Ile Glu Leu Ile Glu Ile Ala Arg Asn Ser Thr Gln Asp Arg
                245                 250                 255

Ile Leu Glu Met Lys Val Met Glu Phe Phe Met Lys Val Tyr Gly Tyr
            260                 265                 270

Arg Gly Lys His Leu Gly Gly Ser Arg Lys Pro Asp Gly Ala Ile Tyr
        275                 280                 285

Thr Val Gly Ser Pro Ile Asp Tyr Gly Val Ile Val Asp Thr Lys Ala
    290                 295                 300

Tyr Ser Gly Gly Tyr Asn Leu Asp Ile Gly Gln Ala Asp Glu Met Glu
305                 310                 315                 320

Arg Tyr Val Glu Glu Asn Gln Thr Arg Asp Lys His Leu Asn Pro Asn
                325                 330                 335

Glu Trp Trp Lys Val Tyr Pro Ser Ser Val Thr Glu Phe Lys Phe Leu
            340                 345                 350

Phe Val Ser Gly His Phe Lys Gly Asn Tyr Lys Ala Gln Leu Thr Arg
        355                 360                 365

Leu Asn His Ile Thr Asn Cys Asn Gly Ala Val Leu Ser Val Glu Glu
    370                 375                 380

Leu Leu Ile Gly Gly Glu Met Ile Lys Ala Gly Thr Leu Thr Leu Glu
385                 390                 395                 400

Glu Val Arg Arg Lys Phe Asn Asn Gly Glu Ile Asn Phe Arg Ser Gly
                405                 410                 415

Gly Gly Glu Gly Arg Gly Ser Leu Leu Thr Cys Gly Asp Val Glu Glu
            420                 425                 430

Asn Pro Gly Pro Arg Thr Met Asp Tyr Lys Asp His Asp Gly Asp Tyr
        435                 440                 445

Lys Asp His Asp Ile Asp Tyr Lys Asp Asp Asp Lys Met Ala Pro
    450                 455                 460

Lys Lys Lys Arg Lys Val Gly Ile His Gly Val Pro Ala Ala Met Gly
465                 470                 475                 480

Gln Leu Val Lys Ser Glu Leu Glu Glu Lys Lys Ser Glu Leu Arg His
                485                 490                 495

Lys Leu Lys Tyr Val Pro His Glu Tyr Ile Glu Leu Ile Glu Ile Ala
            500                 505                 510

Tyr Asn Ser Thr Gln Asp Arg Ile Leu Glu Met Lys Val Met Glu Phe
        515                 520                 525

Phe Met Lys Val Tyr Gly Tyr Arg Gly Lys His Leu Gly Gly Ser Arg
    530                 535                 540

Lys Pro Asp Gly Ala Ile Tyr Thr Val Gly Ser Pro Ile Asp Tyr Gly
545                 550                 555                 560

Val Ile Val Asp Thr Lys Ala Tyr Ser Gly Gly Tyr Asn Leu Pro Ile
                565                 570                 575

Gly Gln Ala Asp Glu Met Gln Arg Tyr Val Lys Glu Asn Gln Thr Arg
            580                 585                 590

Asn Lys His Ile Asn Pro Asn Glu Trp Trp Lys Val Tyr Pro Ser Ser
        595                 600                 605

Val Thr Glu Phe Lys Phe Leu Phe Val Ser Gly His Phe Lys Gly Asn
    610                 615                 620
```

```
Tyr Lys Ala Gln Leu Thr Arg Leu Asn Arg Lys Thr Asn Cys Asn Gly
625                 630                 635                 640

Ala Val Leu Ser Val Glu Glu Leu Leu Ile Gly Gly Glu Met Ile Lys
            645                 650                 655

Ala Gly Thr Leu Thr Leu Glu Glu Val Arg Arg Lys Phe Asn Asn Gly
        660                 665                 670

Glu Ile Asn Phe Ser Gly Ala Gln Gly Ser Thr Leu Asp Phe Arg Pro
    675                 680                 685

Phe Gln Cys Arg Ile Cys Met Arg Lys Phe Ala Ala Gln Cys Cys Leu
690                 695                 700

Phe His His Thr Lys Ile His Thr Gly Glu Lys Pro Phe Gln Cys Arg
705                 710                 715                 720

Ile Cys Met Arg Asn Phe Ser Asp Gln Ser Asn Leu Arg Ala His Ile
                725                 730                 735

Arg Thr His Thr Gly Glu Lys Pro Phe Ala Cys Asp Ile Cys Gly Arg
            740                 745                 750

Lys Phe Ala Arg Ser Ala Asn Leu Thr Arg His Thr Lys Ile His Thr
        755                 760                 765

His Pro Arg Ala Pro Ile Pro Lys Pro Phe Gln Cys Arg Ile Cys Met
770                 775                 780

Arg Asn Phe Ser Arg Ser Asp Asp Leu Thr Arg His Ile Arg Thr His
785                 790                 795                 800

Thr Gly Glu Lys Pro Phe Ala Cys Asp Ile Cys Gly Arg Lys Phe Ala
                805                 810                 815

Gln Ser Gly Ser Leu Thr Arg His Thr Lys Ile His Leu Arg Gln Lys
            820                 825                 830

Asp

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Arg Ser Asp Thr Leu Ser Glu
1               5

<210> SEQ ID NO 187
<211> LENGTH: 100
<212> TYPE: DNA
<213> ORGANISM: Homo sapiens

<400> SEQUENCE: 187
tctggatgct gaaagaatgt ctgttttttcc ttttagaaag ttcctgtgat gtcaagctgg     60
tcgagaaaag ctttgaaaca ggtaagacag gggtctagcc                          100

<210> SEQ ID NO 188
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
aaaaaaaaaa aaaaaaaaaa aaaaaaaaaa aaaaaaaaaa aaaaaaaaaa aaaaaaaa       60
```

-continued aaaa                                                              64

<210> SEQ ID NO 189
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
aaaaaaaaaa aaaaaaaaaa aaaaaaaaaa aaaaaaaaaa aaaaaaaaaa aaaaaaaaaa    60

<210> SEQ ID NO 190
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Leu Arg Gly Ser
1

TARGETED DISRUPTION OF T CELL AND/OR HLA RECEPTORS

CROSS-REFERENCE TO RELATED APPLICATIONS

The present application claims the benefit of U.S. Provisional Application No. 62/521,132, filed Jun. 16, 2017; U.S. Provisional Application 62/542,052, filed Aug. 7, 2017 and U.S. Provisional Application No. 62/573,956, filed Oct. 18, 2017, the disclosures of which are hereby incorporated by reference in their entireties.

SEQUENCE LISTING 0.1] The instant application contains a Sequence Listing which has been submitted electronically in ASCII format and is hereby incorporated by reference in its entirety. Said ASCII copy, created on Jul. 17, 2018, is named 8325-0164_SL.txt and is 129,471 bytes in size.

TECHNICAL FIELD

The present disclosure is in the field of genome modification of human cells, including lymphocytes and stem cells.

BACKGROUND

Gene therapy holds enormous potential for a new era of human therapeutics. These methodologies will allow treatment for conditions that have not been addressable by standard medical practice. Gene therapy can include the many variations of genome editing techniques such as disruption (inactivation) or correction of a gene locus, and/or insertion of an expressible transgene that can be controlled either by a specific exogenous promoter operably linked to the transgene, or by the endogenous promoter found at the site of insertion into the genome.

Delivery and insertion of the transgene are examples of hurdles that must be solved for any real implementation of this technology. For example, although a variety of gene delivery methods are potentially available for therapeutic use, all involve substantial tradeoffs between safety, durability and level of expression. Methods that provide the transgene as an episome (e.g., adenovirus (Ad), adeno-associated virus (AAV) and plasmid-based systems) can yield high initial expression levels, however, these methods lack robust episomal replication, which may limit the duration of expression in mitotically active tissues. In contrast, delivery methods that result in the random integration of the desired transgene (e.g., integrating lentivirus (LV)) provide more durable expression but, due to the untargeted nature of the random insertion, may provoke unregulated growth in the recipient cells, potentially leading to malignancy via activation of oncogenes in the vicinity of the randomly integrated transgene cassette. Moreover, although transgene integration avoids replication-driven loss, it does not prevent eventual silencing of the exogenous promoter fused to the transgene. Over time, such silencing results in reduced transgene expression for the majority of non-specific insertion events. In addition, integration of a transgene rarely occurs in every target cell, which can make it difficult to achieve a high enough expression level of the transgene of interest to achieve the desired therapeutic effect.

In recent years, a new strategy for genetic modification (e.g., inactivation, correction and/or transgene integration) has been developed that uses cleavage with site-specific nucleases (e.g., zinc finger nucleases (ZFNs), transcription activator-like effector domain nucleases (TALENs), CRISPR/Cas system with an engineered crRNA/tracr RNA ('single guide RNA') to guide specific cleavage, etc.) to bias editing at a chosen genomic locus. See, e.g., U.S. Pat. Nos. 9,937,207; 9,255,250; 9,045,763; 9,005,973; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publication Nos. 2017/0211075; 2003/0232410; 2005/0208489; 2005/0026157; 2005/0064474; 2006/0063231; 2008/0159996; 2010/0218264; 2012/0017290; 2011/0265198; 2013/0137104; 2013/0122591; 2013/0177983 and 2013/0177960 and 2015/0056705. Further, targeted nucleases are being developed based on the Argonaute system (e.g., from *T thermophilus*, known as 'TtAgo', see Swarts, et al. (2014) *Nature* 507(7491): 258-261), which also may have the potential for uses in genome editing and gene therapy. This nuclease-mediated approach to genetic modification offers the prospect of improved transgene expression, increased safety and expressional durability, as compared to classic integration approaches, since it allows exact transgene positioning for a minimal risk of gene silencing or activation of nearby oncogenes.

The T cell receptor (TCR) is an essential part of the selective activation of T cells. Bearing some resemblance to an antibody, the antigen recognition part of the TCR is typically made from two chains, α and β, which co-assemble to form a heterodimer. The antibody resemblance lies in the manner in which a single gene encoding a TCR alpha and beta complex is put together. TCR alpha (TCR α) and beta (TCR β) chains are each composed of two regions, a C-terminal constant region and an N-terminal variable region. The genomic loci that encode the TCR alpha and beta chains resemble antibody encoding loci in that the TCR α gene comprises V and J segments, while the β chain locus comprises D segments in addition to V and J segments. For the TCR β locus, there are additionally two different constant regions that are selected from during the selection process. During T cell development, the various segments recombine such that each T cell comprises a unique TCR variable portion in the alpha and beta chains, called the complementarity determining region (CDR), and the body has a large repertoire of T cells which, due to their unique CDRs, are capable of interacting with unique antigens displayed by antigen presenting cells. Once a TCR α or β gene rearrangement has occurred, the expression of the second corresponding TCR α or TCR β is repressed such that each T cell only expresses one unique TCR structure in a process called 'antigen receptor allelic exclusion' (see, Brady, et al. (2010) *J Immunol* 185:3801-3808).

During T cell activation, the TCR interacts with antigens displayed as peptides on the major histocompatability complex (MHC) of an antigen presenting cell. Recognition of the antigen-MHC complex by the TCR leads to T cell stimulation, which in turn leads to differentiation of both T helper cells (CD4+) and cytotoxic T lymphocytes (CD8+) in memory and effector lymphocytes. These cells then can expand in a clonal manner to give an activated subpopulation within the whole T cell population capable of reacting to one particular antigen.

MHC proteins are of two classes, I and II. The class I MHC proteins are heterodimers of two proteins, the α chain, which is a transmembrane protein encoded by the MHC 1 class I genes, and the β2 microglobulin chain (sometimes referred to as B2M), which is a small extracellular protein that is encoded by a gene that does not lie within the MHC gene cluster. The α chain folds into three globular domains and when the β2 microglobulin chain is associated, the globular structure complex functional and expressed on the cell surface. Peptides are presented on the two most N-terminal domains which are also the most variable. Class II MHC proteins are also heterodimers, but the heterodimers comprise two transmembrane proteins encoded by genes within the MHC complex. The class I MHC:antigen complex interacts with cytotoxic T cells while the class II MHC presents antigens to helper T cells. In addition, class I MHC proteins tend to be expressed in nearly all nucleated cells and platelets (and red blood cells in mice) while class II MHC protein are more selectively expressed. Typically, class II MHC proteins are expressed on B cells, some macrophage and monocytes, Langerhans cells, and dendritic cells.

In humans, the major histocompatibility complex (MHC) is commonly known as the human leukocyte antigen (HLA). The class I HLA gene cluster in humans comprises three major loci, B, C and A, as well as several minor loci (including E, G and F, all found in the HLA region on chromosome 6). The class II HLA cluster also comprises three major loci, DP, DQ and DR, and both the class I and class II gene clusters are polymorphic, in that there are several different alleles of both the class I and II genes within the population. There are also several accessory proteins that play a role in HLA functioning as well. β-2 microglobulin functions as a chaperon (encoded by B2M, located on chromosome 15) and stabilizes the HLA A, B or C protein expressed on the cell surface and also stabilizes the antigen display groove on the class I structure. It is found in the serum and urine in low amounts normally.

HLA plays a major role in transplant rejection. The acute phase of transplant rejection can occur within about 1-3 weeks and usually involves the action of host T lymphocytes on donor tissues due to sensitization of the host system to the donor class I and class II HLA molecules. In most cases, the triggering antigens are the class I HLAs. For best success, donors are typed for HLA and matched to the patient recipient as completely as possible. But donation even between family members, which can share a high percentage of HLA identity, is still often not successful. Thus, in order to preserve the graft tissue within the recipient, the patient often must be subjected to profound immunosuppressive therapy to prevent rejection. Such therapy can lead to complications and significant morbidities due to opportunistic infections that the patient may have difficulty overcoming. Regulation of the class I or II genes can be disrupted in the presence of some tumors and such disruption can have consequences on the prognosis of the patients. For example, reduction of B2M expression was found in metastatic colorectal cancers (Shrout, et al. (2008) *Br J Canc* 98:1999). Since B2M has a key role in stabilizing the MHC class I complex, loss of B2M in certain solid cancers has been hypothesized to be a mechanism of immune escape from T cell driven immune surveillance. Depressed B2M expression has been shown to be a result of suppression of the normal IFN gamma B2M expressional regulation and/or specific mutations in the B2M coding sequence that result in gene knock-out (Shrout, et al., ibid). Confoundingly, increased B2M is also associated with some types of cancer. Increased B2M levels in the urine serves as a prognosticator for several cancers including prostate, chronic lymphocytic leukemia (CLL) and Non-Hodgkin's lymphomas.

Adoptive cell therapy (ACT) is a developing form of cancer therapy based on delivering tumor-specific immune cells to a patient in order for the delivered cells to attack and clear the patient's cancer. ACT can involve the use of tumor-infiltrating lymphocytes (TILs) which are T-cells that are isolated from a patient's own tumor masses and expanded ex vivo to re-infuse back into the patient. This approach has been promising in treating metastatic melanoma, where in one study, a long term response rate of >50% was observed (see for example, Rosenberg, et al. (2011) *Clin Canc Res* 17(13): 4550). TILs are a promising source of cells because they are a mixed set of the patient's own cells that have T-cell receptors (TCRs) specific for the Tumor associated antigens (TAAs) present on the tumor (Wu, et al. (2012) *Cancer J* 18(2): 160). Other approaches involve editing T cells isolated from a patient's blood such that they are engineered to be responsive to a tumor in some way (Kalos, et al. (2011) *Sci Transl Med* 3(95):95ra73).

Chimeric Antigen Receptors (CARs) are molecules designed to target immune cells to specific molecular targets expressed on cell surfaces. In their most basic form, they are receptors introduced into a cell that couple a specificity domain expressed on the outside of the cell to signaling pathways on the inside of the cell such that when the specificity domain interacts with its target, the cell becomes activated. Often CARs are made from emulating the functional domains of T-cell receptors (TCRs) where an antigen specific domain, such as a scFv or some type of receptor, is fused to the signaling domain, such as ITAMs and other co-stimulatory domains. These constructs are then introduced into a T-cell ex vivo allowing the T-cell to become activated in the presence of a cell expressing the target antigen, resulting in the attack on the targeted cell by the activated T-cell in a non-MHC dependent manner (see Chicaybam, et al. (2011) *Int Rev Immunol* 30:294-311) when the T-cell is re-introduced into the patient. Thus, adoptive cell therapy using T cells altered ex vivo with an engineered TCR or CAR is a very promising clinical approach for several types of diseases. For example, cancers and their antigens that are being targeted includes follicular lymphoma (CD20 or GD2), neuroblastoma (CD171), non-Hodgkin lymphoma (CD19 and CD20), lymphoma (CD19), glioblastoma (IL13Ra2), chronic lymphocytic leukemia or CLL and acute lymphocytic leukemia or ALL (both CD19). Virus specific CARs have also been developed to attack cells harboring virus such as HIV. For example, a clinical trial was initiated using a CAR specific for Gp100 for treatment of HIV (Chicaybam, ibid).

ACTRs (Antibody-coupled T-cell Receptors) are engineered T cell components that are capable of binding to an exogenously supplied antibody. The binding of the antibody to the ACTR component arms the T cell to interact with the antigen recognized by the antibody, and when that antigen is encountered, the ACTR comprising T cell is triggered to interact with antigen (see U.S. Patent Publication No. 2015/0139943).

One of the drawbacks of adoptive cell therapy however is the source of the cell product must be patient specific (autologous) to avoid potential rejection of the transplanted cells. This has led researchers to develop methods of editing a patient's own T cells to avoid this rejection. For example, a patient's T cells or hematopoietic stem cells can be manipulated ex vivo with the addition of an engineered CAR, ACTR and/or T cell receptor (TCR), and then further treated with engineered nucleases to knock out T cell check point inhibitors such as PD1 and/or CTLA4 (see International Patent Publication No. WO 2014/059173). For application of this technology to a larger patient population, it would be advantageous to develop a universal population of cells (allogeneic). In addition, knockout of the TCR will result in cells that are unable to mount a graft-versus-host disease (GVHD) response once introduced into a patient.

Thus, there remains a need for methods and compositions that can be used to modify (e.g., knock out) TCR and/or HLA expression in effector T cells, regulatory T cells, B cells, NK cells or stem cells (e.g., hematopoietic stem cells, induced pluripotent stem cells and embryonic stem cells).

SUMMARY

Disclosed herein are compositions and methods for partial or complete inactivation or disruption of a TCR and/or B2M gene and compositions and methods for introducing and expressing to desired levels of exogenous transgenes in T lymphocytes, after or simultaneously with the disruption of the endogenous TCR and/or B2M. Also provided herein are methods and compositions for deleting (inactivating) or repressing a TCR and/or B2M gene to produce TCR null T cell or TCR and HLA class I null T cell, B cells, NK cell, stem cell, tissue or whole organism, for example a cell that does not express one or more T cell receptors and/or one or more HLA class I receptors on its surface. Additional genomic modifications may be present in the TCR and/or HLA class I null cells described herein, including, but not limited to genomic modifications to a different gene (e.g., a programmed cell death 1 (PD 1) gene, a Cytotoxic T-Lymphocyte Antigen 4 (CTLA-4) gene, a CISH gene, a tet2 gene, an human leukocyte antigen (HLA) A gene, an HLA B gene, an HLA C gene, an HLA-DPA gene, an HLA-DQ gene, an HLA-DRA gene, a LMP7 gene, a Transporter associated with Antigen Processing (TAP) 1 gene, a TAP2 gene, a tapasin gene (TAPBP), a class II major histocompatibility complex transactivator (CIITA) gene, a glucocorticoid receptor gene (GR), an IL2RG gene, an RFX5 gene), insertion of transgene (e.g., CAR) into one or more of these or other genes (e.g., safe harbor genes) and any combination of such genomic modifications. In certain embodiments, the TCR null cells and/or HLA class I null cells, or tissues are human cells or tissues that are advantageous for use in transplants. In preferred embodiments, the TCR null T cells and/or HLA class I null cells are prepared for use in adoptive T cell therapy.

In one aspect, described herein is a zinc finger nuclease comprising: a ZFP from a ZFN designated 68957, 72678, 72732 or 72748; an engineered FokI cleavage domain; and a linker between the FokI cleavage domain and the ZFP. In certain embodiments, the ZFN comprises first and second ZFNs as follows (amino acid and polynucleotide sequences disclosed in the Examples): a ZFN comprising a ZFP from the ZFN designated 72678 and a ZFN comprising a ZFP from the ZFN designated 72732. In certain embodiments the ZFN comprises left and right (first and second) ZFNs as follows: a ZFN designated 57531 and a ZFN designated 72732; a ZFN designated 57531 and a ZFN designated 72748; a ZFN designated 68957 and a ZFN designated 57071; a ZFN designated 68957 and a ZFN designated 72732; a ZFN designated 68957 and a ZFN designated 72748; a ZFN designated 72678 and a ZFN designated 57071; a ZFN designated 72678 and a ZFN designated 72732; and a comprising a ZFP ZFN designated 72678 and a ZFN designated 72748. A zinc finger nuclease (ZFN) comprising left and right (first and second) ZFNs as follows: a ZFN designated 68796 and a ZFN designated 68813; a ZFN designated 68796 and a ZFN designated 68861; a ZFN designated 68812 and a ZFN designated 68813; a ZFN designated 68876 and a ZFN designated 68877; a ZFN designated 68815 and a ZFN designated 55266; a ZFN designated 68879 and a ZFN designated 55266; a ZFN designated 68798 and a ZFN designated 68815; or a ZFN designated 68846 and a ZFN designated 53853. Polynucleotides (e.g., mRNA, plasmids, viral vectors, etc.) encoding a ZFN (including a pair) as disclosed herein are also provided, including a polynucleotide comprising a 2A sequence between the sequences encoding the left and ZFNs. Also disclosed are genetically modified cells (e.g., stem cells, precursor cells, T cells (effector and regulatory), etc.) comprising one or more of the ZFNs and/or polynucleotides disclosed herein and cells descended from these cells (e.g., genetically modified cells that do not comprise the ZFN but include the genetic modification). The genetic modifications include insertions, deletions and combinations thereof in the gene targeted by the ZFN. Additional genomic modifications, for example, modification of a T cell receptor (TCR) gene, modification of an HLA-A gene, modification of an HLA-B gene, modification of an HLA-C gene, modification of a TAP gene, modification of a CTLA-4 gene, modification of a PD1 gene, modification of a CISH gene, modification of a tet-2 gene, and/or insertion of a transgene (e.g., CAR) may be present at the target and/or one or more different loci. Pharmaceutical compositions comprising any of the zinc finger nucleases, polynucleotides, and/or cells as described herein are also provided. Methods of modifying an endogenous beta-2-microglobulin (B2M) and/or TCR gene in a cell are also provided, the method comprising administering a polynucleotide or pharmaceutical composition as described herein to the cell such that the endogenous gene is modified (e.g., deletion, insertion of an exogenous sequence such as a transgene). Methods of using the ZFNs, polynucleotides, cells and/or pharmaceutical compositions as described herein for the treatment and/or prevention of a cancer, an autoimmune disease or graft-versus-host disease are also provided. Kits comprising any of the ZFNs, polynucleotides, cells and/or pharmaceutical compositions as described herein are also provided.

In other aspects, described herein is an isolated cell (e.g., a eukaryotic cell such as a mammalian cell including a lymphoid cell, a stem cell (e.g., iPSC, embryonic stem cell, MSC or HSC), or a progenitor/precursor cell) in which expression of a TCR gene is modulated by modification of exonic sequences of the TCR gene. In certain embodiments, the modification is to a sequence comprising a sequence of 9-25 (including target sites of 9, 10, 11, 12, 13, 14, 15, 16, 17, 18, 19, 20, 21, 22, 23, 24, 25) or more nucleotides (contiguous or non-contiguous) of a sequence as shown in the target sites herein) of a target site as shown in one or more of Tables 1, 2 or 6 (SEQ ID NO: 8-21 and/or 92-103); within 1-5, within 1-10 or within 1-20 base pairs on either side (the flanking genomic sequence) of the target sites shown in Tables 1, 2 or 6 (SEQ ID NO:8-21 and/or 92-103); or within AACAGT, AGTGCT, CTCCT, TTGAAA, TGGACTT and AATCCTC or a target site comprising AACAGT, AGTGCT, CTCCT, TTGAAA, TGGACTT and AATCCTC. Alternatively, or in addition, the modifications may also be made to sequences (e.g., genomic sequences) between paired target sites of as described herein (e.g., target sites for the nuclease pairs shown in Table 3, including between the target sites for 55204 and 53759 (between SEQ ID NO:8 and SEQ ID NO:9); between the target sites for 55229 and 53785 (between SEQ ID NO: 10 and SEQ ID NO: 11); between the target sites for 53810 and 55255 (between SEQ ID NO:12 and SEQ ID NO: 13); between target sites shown for 55248 and 55254/55260 (between SEQ ID NO: 14 and SEQ ID NO: 13); between the target sites for 55266 and 53853 (between SEQ ID NO:15 and SEQ ID NO:16); between the target sites for 53860 and 53863 (between SEQ ID NO:17 and SEQ ID NO: 18); between the target sites for 53856 and 55287 (between SEQ ID NO:21 and SEQ ID NO:18); or between the target sites for 53885 or 52774 and 53909 or 52742 (between SEQ ID NO:19 and SEQ ID NO:20). The modification may be by an exogenous fusion molecule comprising a functional domain (e.g., transcriptional regulatory domain, nuclease domain including any FokI cleavage domain with one or more mutations as compared to wild-type) and a DNA-binding domain, including, but not limited to: (i) a cell comprising an exogenous transcription factor comprising a DNA-binding domain that binds to a target site as shown in any of SEQ ID NO:8-21 and/or 92-103 and a transcriptional regulatory domain in which the transcription factor modifies TRAC gene expression and/or (ii) a cell comprising an insertion and/or a deletion within one or more of the target sites shown herein, including SEQ ID NO:8-21 and/or 92-103; within 1-5, within 1-10 or within 1-20 base pairs on either side (the flanking genomic sequence) of the target sites shown in Tables 1 and 2 (SEQ ID NO: 8-21 and/or 92-103); within AACAGT, AGTGCT, CTCCT, TTGAAA, TGGACTT and AATCCTC; and/or between paired target sites as described herein (e.g., target sites for the nuclease pairs shown in Table 3). Cells comprising these modifications to TCR gene(s) and additional genetic modifications (e.g., B2M gene modification, CTLA, CISH, PD1 and/or tet2 gene modifications, CAR, an antigen-specific TCR (alpha and beta chains), insertions at these or other loci including a transgene encoding an Antibody-coupled T-cell Receptor (ACTR) and/or a transgene encoding an antibody, etc.) are also described.

In another aspect, described herein is an isolated cell (e.g., a eukaryotic cell such as a mammalian cell including a lymphoid cell, a stem cell (e.g., iPSC, embryonic stem cell, MSC or HSC), or a progenitor/precursor cell) in which expression of a B2M gene is modulated by modification of the B2M gene. In certain embodiments, the modification is to a sequence comprising a sequence of 9-25 (including target sites of 9, 10, 11, 12, 13, 14, 15, 16, 17, 18, 19, 20, 21, 22, 23, 24, 25) or more nucleotides (contiguous or non-contiguous) of a sequence as shown in the target sites herein) of a target site as shown in one or more of Tables 5 and 8 (SEQ ID NO: 117, 123, 126 and/or 127); within 1-5, within 1-10 or within 1-20 base pairs on either side (the flanking genomic sequence) of the target sites shown in Tables 5 and 8 (SEQ ID NO:117, 123, 126 and/or 127). Alternatively, or in addition, the modifications may also be made to sequences (e.g., genomic sequences) between paired target sites of as described herein (e.g., target sites for the nuclease pairs shown in Tables 5 and 8, including between the target sites as shown in Table 8 (SEQ ID NO: 126 and 127). The modification may be by an exogenous fusion molecule comprising a functional domain (e.g., transcriptional regulatory domain, nuclease domain including any FokI cleavage domain with one or more mutations as compared to wild-type) and a DNA-binding domain (e.g., a ZFP as shown in Table 8 (the ZFP component (designs) of the ZFNs designated 72732; 72748; 68957; or 72678), including, but not limited to: (i) a cell comprising an exogenous transcription factor comprising a DNA-binding domain that binds to a target site as shown in any of Tables 5 or 8 (e.g., SEQ ID NO: 126 or 127) and a transcriptional regulatory domain in which the transcription factor modifies B2M gene expression and/or (ii) a cell comprising an insertion and/or a deletion within one or more of the target sites shown herein, including Tables 5 and 8; within 1-5, within 1-10 or within 1-20 base pairs on either side (the flanking genomic sequence); and/or between paired target sites as described herein (e.g., target sites for the nuclease pairs shown in Table 8). Cells comprising these modifications to B2M genes and additional genetic modifications (e.g., TCR gene modification, CTLA, CISH, PD1 and/or tet2 gene modifications, PD1 modification, a CAR insertion, an antigen-specific TCR (alpha and beta chains), insertions at these or other loci including a transgene encoding an Antibody-coupled T-cell Receptor (ACTR) and/or a transgene encoding an antibody, etc.) are also described.

The TCR and/or B2M modified cells described herein may include further modifications, for example one or more inactivated T-cell receptor genes in B2M modified cells, additional inactivated TCR genes, PD 1 and/or CTLA4 gene and/or a transgene a transgene encoding a chimeric antigen receptor (CAR), a transgene encoding an Antibody-coupled T-cell Receptor (ACTR) and/or a transgene encoding an antibody. Pharmaceutical compositions comprising any cell as described herein are also provided as well as methods of using the cells and pharmaceutical compositions in ex vivo therapies for the treatment of a disorder (e.g., a cancer) in a subject. In certain embodiments, a population of cells comprising one or more modifications (TCR edits, B2M edits, PD1 edits, CISH, tet2 and/or CTLA4 edits, HLA class I gene edits and/or transgene (e.g., CAR) insertions into these or other genes, etc.) as described herein are provided, including a population of cells in which less than 5% (e.g., 0-5% or any value therebetween), preferably less than 3%, even more preferably less than 2% of the cells include any other modifications (e.g., modifications at off-target sites). In certain embodiments, the population of cells includes modifications at off-target sites at background levels (e.g., 2-10-fold less (or any value therebetween)) as compared to cells modified with ZFNs that are not modified as described herein (which unmodified ZFNs are also referred to as "parent" or "parental" ZFNs). The modifications made by the ZFNs are heritable in that, in vivo or in culture, cells descended from (including differentiated cells) cells comprising the ZFNs (and modifications) include the modifications described herein.

Thus, in one aspect, described herein are cells in which the expression of a TCR gene is modulated (e.g., activated, repressed or inactivated). In preferred embodiments, exonic sequences of a TCR gene are modulated. The modulation may be by an exogenous molecule (e.g., engineered transcription factor comprising a DNA-binding domain and a transcriptional activation or repression domain) that binds to the TCR gene and regulates TCR expression and/or via sequence modification of the TCR gene (e.g., using a nuclease that cleaves the TCR gene and modifies the gene sequence by insertions and/or deletions), including for example a ZFN (e.g., ZFN pair of left and right ZFNs) as shown in Table 6. In some embodiments, cells are described that comprise an engineered nuclease to cause a knockout of a TCR gene. In other embodiments, cells are described that comprise an engineered transcription factor (TF) such that the expression of a TCR gene is modulated. In some embodiments, the cells are T cells. Further described are cells wherein the expression of a TCR gene is modulated and wherein the cells are further engineered to comprise a least one exogenous transgene and/or an additional knock out of at least one endogenous gene (e.g., beta 2 microglobuin (B2M) and/or immunological checkpoint gene such as PD 1 and/or CTLA4) or combinations thereof.

In another aspect, described herein are cells in which the expression of a B2M gene is modulated (e.g., activated, repressed or inactivated). The modulation may be by an exogenous molecule (e.g., engineered transcription factor comprising a DNA-binding domain and a transcriptional activation or repression domain) that binds to the B2M gene and regulates B2M expression and/or via sequence modification of the B2M gene (e.g., using a nuclease that cleaves the B2M gene and modifies the gene sequence by insertions and/or deletions), including for example a ZFN (e.g., ZFN pair of left and right ZFNs) as shown in Table 8 or a ZFN comprising a ZFP having the design (recognition helix region and backbone of ZFPs in ZFNs designated 72732; 72748; 68957; or 72678) described herein (e.g., Table 8) in combination with any FokI domain (wild-type or engineered) and optionally any linker between the FokI domain and the ZFP (e.g., L0, N7a, N7c, etc.). In some embodiments, cells are described that comprise an engineered nuclease to cause a knockout of a B2M gene. In other embodiments, cells are described that comprise an engineered transcription factor (TF) such that the expression of a B2M gene is modulated. In some embodiments, the cells are T cells, including effector T cells and regulatory T cells. Further described are cells wherein the expression of a B2M gene is modulated and wherein the cells are further engineered to comprise a least one exogenous transgene and/or an additional knock out of at least one endogenous gene (e.g., one or more TCR genes and/or immunological checkpoint gene such as PD1 and/or CTLA4) or combinations thereof.

In any of the cells described herein comprising an exogenous transgene, the exogenous transgene may be integrated into a TCR and/or B2M gene (e.g., when the TCR and/or B2M gene is knocked out) and/or may be integrated into a gene such as a safe harbor gene. In some cases, the exogenous transgene encodes an ACTR, an antigen-specific TCR, and/or a CAR. The transgene construct may be inserted by either HDR- or NHEJ-driven processes. In some aspects the cells with modulated TCR and/or B2M expression comprise at least an exogenous ACTR, an exogenous TCR and an exogenous CAR. Some cells comprising a TCR modulator further comprise a knockout of one or more check point inhibitor genes. In some embodiments, the check point inhibitor is PD1. In other embodiments, the check point inhibitor is CTLA4. In further aspects, the TCR and/or B2M modulated cell comprises a PD1 knockout and a CTLA4 knockout. In some embodiments, the TCR gene modulated is a gene encoding TCR β (TCRB). In some embodiments this is achieved via targeted cleavage of the constant region of this gene (TCR β Constant region, or TRBC). In certain embodiments, the TCR gene modulated is a gene encoding TCR α (TCRA). In further embodiments, insertion is achieved via targeted cleavage of the constant region of a TCR gene, including targeted cleavage of the constant region of a TCR α gene (referred to herein as "TRAC" sequences). In some embodiments, the TCR gene modified cells are further modified at the B2M gene, the HLA-A, -B, -C genes, or the TAP gene, or any combination thereof. In other embodiments, the regulator for HLA class II, CIITA, is also modified.

In certain embodiments, the cells described herein comprise a modification (e.g., deletion and/or insertion, binding of an engineered TF to repress TCR expression) to a TCRA gene (e.g., modification of exons). In certain embodiments, the modification is within any of the target sites shown in Tables 1, 2 or 6 (SEQ ID NO:8-21 and/or 92-103) and/or between paired target sites (e.g., target sites of nuclease pairs shown in Table 3), including modification by binding to, cleaving, inserting and/or deleting one or more nucleotides within any of these sequences and/or within 1-50 base pairs (including any value therebetween such as 1-5, 1-10 or 1-20 base pairs) of the gene (genomic) sequences flanking these sequences in the TCRA gene. In certain embodiments, the modifications are made using a ZFN (e.g., one or more ZFN pairs) as shown in Table 6. In certain embodiments, the cells comprise a modification (binding to, cleaving, insertions and/or deletions) within one or more of the following sequences: AACAGT, AGTGCT, CTCCT, TTGAAA, TGGACTT and AATCCTC within a TCRA gene (e.g., exons, see FIG. 1B). In certain embodiments, the modification comprises binding of an engineered TF as described herein such that a TCRA gene expression is modulated, for example, repressed or activated.

In certain embodiments, the cells described herein comprise a modification (e.g., deletion and/or insertion, binding of an engineered TF to repress B2M expression) to a B2M gene. In certain embodiments, the modification is within any of the target sites shown in Tables 5 or 8 and/or between paired target sites (e.g., target sites of nuclease pairs shown in Table 8), including modification by binding to, cleaving, inserting and/or deleting one or more nucleotides within any of these sequences and/or within 1-50 base pairs (including any value therebetween such as 1-5, 1-10 or 1-20 base pairs) of the gene (genomic) sequences flanking these sequences in the B2M gene. In certain embodiments, the modifications are made using a ZFN comprising a ZFP comprising the recognition helix regions and backbone of the ZFP designs of the ZFNs shown in Table 8, a FokI domain (any wild-type or engineered FokI domain) and optionally a linker (any linker between the N- or C-terminal of the FokI domain and the N- or C-terminal of the ZFP designs shown including but not limited to L0, N7a, N7c, etc.). In certain embodiments, the ZFN comprises a ZFN (e.g., a pair of first and second ZFNs) as shown in Table 8. In certain embodiments, the cells comprise a modification (binding to, cleaving, insertions and/or deletions) within one or more of the following sequences: SEQ ID NO: 126 and 127. In certain embodiments, the modification comprises binding of an engineered TF as described herein such that B2M gene expression is modulated, for example, repressed or activated.

In other embodiments, the modification is a genetic modification (alteration of nucleotide sequence) at or near nuclease(s) binding (target) and/or cleavage site(s), including but not limited to, modifications to sequences within 1-300 (or any number of base pairs therebetween) base pairs upstream, downstream and/or including 1 or more base pairs of the site(s) of cleavage and/or binding site; modifications within 1-100 base pairs (or any number of base pairs therebetween) of including and/or on either side of the binding and/or cleavage site(s); modifications within 1 to 50 base pairs (or any number of base pairs therebetween) including and/or on either side (e.g., 1 to 5, 1 to 10, 1 to 20 or more base pairs) of the binding and/or cleavage site(s); and/or modifications to one or more base pairs within the nuclease binding site and/or cleavage site. In certain embodiments, the modification is at or near (e.g., 1-300 base pairs, 1-50, 1-20, 1-10 or 1-5 or any number of base pairs therebetween) and/or between paired target sites (e.g., Table 3 or 8) of the gene sequence surrounding or between any of the target sites disclosed herein. In certain embodiments, the modification includes modifications of a TCRA and/or B2M gene within one or more of the sequences shown in in the target sites of Tables 1, 2 and 6 (TCRA) and/or Tables 5 and 8 (B2M), for example a modification of 1 or more base pairs to one or more of these sequences. In certain embodiments, the nuclease-mediated genetic modifications are between paired target sites (when a dimer is used to cleave the target). The nuclease-mediated genetic modifications may include insertions and/or deletions of any number of base pairs, including insertions of non-coding sequences of any length and/or transgenes of any length and/or deletions of 1 base pair to over 1000 kb (or any value therebetween including, but not limited to, 1-100 base pairs, 1-50 base pairs, 1-30 base pairs, 1-20 base pairs, 1-10 base pairs or 1-5 base pairs).

The modified cells of the invention may be a eukaryotic cell, including a non-human mammalian and a human cell such as lymphoid cell (e.g., a T-cell (including an effector T cell (Teff) and a regulatory T cell (Treg)), a B cell or an NK cell), a stem/progenitor cell (e.g., an induced pluripotent stem cell (iPSC), an embryonic stem cell (e.g., human ES), a mesenchymal stem cell (MSC), or a hematopoietic stem cell (HSC). The stem cells may be totipotent or pluripotent (e.g., partially differentiated such as an HSC that is a pluripotent myeloid or lymphoid stem cell). In other embodiments, the invention provides methods for producing cells that have a null genotype for TCR and or HLA expression. Any of the modified stem cells described herein (modified at the TCRA and/or B2M loci) may then be differentiated to generate a differentiated (in vivo or in vitro (culture)) cell descended from a stem cell as described herein with the modifications described herein, including modified TCRA and/or B2M gene expression.

In another aspect, the compositions (modified cells) and methods described herein can be used, for example, in the treatment or prevention or amelioration of a disorder. The methods typically comprise (a) cleaving or down regulating an endogenous TCR and/or B2M gene in an isolated cell (e.g., T-cell or other lymphocytes) using a nuclease (e.g., ZFN or TALEN) or nuclease system such as CRISPR/Cas with an engineered crRNA/tracr RNA, or using an engineered transcription factor (e.g., ZFP-TF, TALE-TF, Cfp1-TF or Cas9-TF) such that the TCR and/or B2M gene is inactivated or down modulated; and (b) introducing the cell into the subject, thereby treating or preventing the disorder. In some embodiments, the gene encoding TCR β (TCRB) is inactivated or down-modulated. In some embodiments, the gene encoding B2M is inactivated or down-modulated. In some embodiments inactivation is achieved via targeted cleavage of the constant region of this gene (TCR β Constant region, or TRBC). In preferred embodiments, the gene encoding TCR α (TCRA) and/or B2M is inactivated or down modulated. In further preferred embodiments, the disorder is a cancer, an infectious disease or an autoimmune disease. In some embodiments, the modifications are made to induce immune tolerance. In further preferred embodiments inactivation is achieved via targeted cleavage of the constant region of this gene (TCR α Constant region, or abbreviated as TRAC). In some embodiments, a B2M gene is cleaved. In further embodiments, the additional genes (in addition to TCR and/or B2M) are modulated (knocked-out), for example, TCR/B2M double knockouts, additional TCR genes, PD1 and/or CTLA4 and/or one or more therapeutic transgenes are present in the cell (episomal, randomly integrated or integrated via targeted integration such as nuclease-mediated integration). The modified cells may include one or more ZFNs (e.g., ZFN pairs) as described herein, including but not limited to a zinc finger nuclease (ZFN) comprising first and second ZFNs, each ZFN comprising a cleavage domain (e.g., any wild-type or engineered FokI cleavage domain) and a ZFP DNA-binding domain. In certain embodiments, the modifications are made using a ZFN comprising a ZFP (recognition helix regions and backbone) of the "designs" described herein (e.g., Table 6 or Table 8 including the ZFPs of the ZFNs designated 68846, 53853, 72732; 72748; 68957; 55266, 68798, 68879, 68815, 68799 or 72678), a FokI domain (any wild-type or engineered FokI domain) and optionally a linker (any linker between the N- or C-terminal of the FokI domain and the N- or C-terminal of the ZFP designs described herein). In some embodiments the ZFN comprises a pair of ZFNs, in which one ZFN comprises the ZFP of 68846 (SEQ ID NO: 177) operably linked to a FokI domain and the other ZFN of the pair comprises the ZFP of 53853 (SEQ ID NO: 178) operably linked to a FokI domain. In some embodiments the ZFN comprises a pair of ZFNs, in which one ZFN comprises the ZFP of 72732 (SEQ ID NO:175) operably linked to a FokI domain and the other ZFN of the pair comprises the ZFP of 72678 (SEQ ID NO:176) operably linked to a FokI domain. In certain embodiments, the ZFN comprises a ZFN (e.g., a pair of first and second (also referred to as left and right) partner ZFNs) described herein as follows: a ZFN designated 68796 and a ZFN designated 68813; a ZFN designated 68796 and a ZFN designated 68861; a ZFN designated 68812 and a ZFN designated 68813; a ZFN designated 68876 and a ZFN designated 68877; a ZFN designated 68815 and a ZFN designated 55266; a ZFN designated 68879 and a ZFN designated 55266; a ZFN designated 68798 and a ZFN designated 68815; or a ZFN designated 68846 and a ZFN designated 53853; a ZFN designated 57531 and a ZFN designated 72732; a ZFN designated 57531 and a ZFN designated 72748; a ZFN designated 68957 and a ZFN designated 57071; a ZFN designated 68957 and a ZFN designated 72732; a ZFN designated 68957 and a ZFN designated 72748; a ZFN designated 72678 and a ZFN designated 57071; a ZFN designated 72678 and a ZFN designated 72732; and a comprising a ZFP ZFN designated 72678 and a ZFN designated 72748. Thus, a ZFN (e.g., each ZFN partner of a paired ZFN) comprises the recognition helix regions and may comprise additional ZFP modifications (e.g., to the backbone regions) described below (e.g., designs shown in Tables 1, 2, 5, 6 and 8) and further comprises any wild-type or engineered FokI cleavage domain (including any combination of the FokI substitution, addition and/or deletion mutants). For example, a ZFN partner may comprise specific zinc finger DNA binding domain fused to any FokI cleavage domain including the cleavage domain (SEQ ID NO: 139) from the wildtype protein or from a mutated sequence (as shown in the Examples, SEQ ID NO:140-174). A B2M-specific ZFN partner may comprise a B2M-specific zinc finger DNA binding domain (e.g., 72732) fused with a FokI cleavage domain selected from SEQ ID NOs: 139-174. Further, the B2M-specific ZFN partner may comprise a B2M-specific zinc finger DNA binding domain (e.g., 72678) fused to a FokI cleavage domain selected from SEQ ID NOs: 139-174. Similarly, a TRAC-specific ZFN partner may comprise a TRAC-specific zinc finger DNA binding domain (e.g., 68846) fused to a FokI cleavage domain selected from SEQ ID NOs: 139-174, and the TRAC-specific zinc finger DNA binding domain 53853 may be fused to a FokI cleavage domain selected from any of wild-type or engineered FokI cleavage shown, for example a domain as shown in the appended Examples (SEQ ID NOs:139-174). In some embodiments, the FokI domain is fused at the N-terminal end of the ZFP DNA binding domain while in others, it is fused to the C-terminal end of the ZFP DNA binding domain. Further, any linker can be used to link the DNA-binding domain to the FokI cleavage domain.

Cells descended from cells modified as described herein (e.g., cells comprising the ZFNs described herein), including but not limited partially or fully differentiated from stem cells modified as described herein, are also provided. These cells typically do not include the ZFNs but do include the genetic modifications made thereby.

The transcription factor(s) and/or nuclease(s) can be introduced into a cell or the surrounding culture media as mRNA, in protein form and/or as a DNA sequence encoding the nuclease(s). In certain embodiments, the isolated cell introduced into the subject further comprises additional genomic modification, for example, an integrated exogenous sequence (into the cleaved TCR and/or B2M gene or a different gene, for example a safe harbor gene or locus) and/or inactivation (e.g., nuclease-mediated) of additional genes, for example one or more HLA genes, or CTLA-4, CISH, PD1, or tet2 genes. The exogenous sequence (e.g., a CAR or exogenous TCR) or protein may be introduced via a vector (e.g., Ad, AAV, LV), or by using a technique such as electroporation or transient transfection. In some embodiments, the proteins are introduced into the cell by inducing mechanical stress such as cell squeezing (see Kollmannsperger, et al. (2016) *Nat Comm* 7, 10372 doi: 10.1038/ncomms10372). In some aspects, the composition may comprise isolated cell fragments and/or differentiated (partially or fully) cells.

In some aspects, the modified cells may be used for cell therapy, for example, for adoptive cell transfer. In other embodiments, the cells for use in T cell transplant contain another gene modification of interest. In one aspect, the T cells contain an inserted chimeric antigen receptor (CAR) specific for a marker found on cancer cells. In a further aspect, the inserted CAR is specific for the CD19 marker characteristic of B cells, including B cell malignancies. Such cells would be useful in a therapeutic composition for treating patients without having to match HLA, and so would be able to be used as an "off-the-shelf" therapeutic for any patient in need thereof. In other instances, stem or precursor cells, for example, hematopoietic stem cell or precursor cells (HSC/PC) or induced pluripotent stem cells (iPSC) containing the modifications described herein are expanded prior to introduction. In other aspects, the genetically modified HSC/PCs are given to the subject in a bone marrow transplant wherein the HSC/PC engraft, differentiate and mature in vivo. In some embodiments, the HSC/PC are isolated from the subject following G-CSF-induced mobilization, plerixafor-induced mobilization, and combinations of G-CSF- and plerixafor-induced mobilization, and in others, the cells are isolated from human bone marrow or human umbilical cords. In other embodiments, iPSC are derived from patient or healthy donor cells. In some aspects, the subject is treated to a mild myeloablative procedure prior to introduction of the graft comprising the modified HSC/PC or modified cells derived from iPSC, while in other aspects, the subject is treated with a vigorous myeloablative conditioning regimen. In some embodiments, the methods and compositions of the invention are used to treat or prevent a cancer.

In another aspect, the TCR- and/or B2M-modulated (modified) T cells contain an inserted Antibody-coupled T-cell Receptor (ACTR) donor sequence. In some embodiments, the ACTR donor sequence is inserted into a TCR gene to disrupt expression of that TCR gene following nuclease induced cleavage. In other embodiments, the donor sequence is inserted into a "safe harbor" locus, such as the AAVS1, HPRT, albumin and CCR5 genes. In some embodiments, the ACTR sequence is inserted via targeted integration where the ACTR donor sequence comprises flanking homology arms that have homology to the sequence flanking the cleavage site of the engineered nuclease. In some embodiments the ACTR donor sequence further comprises a promoter and/or other transcriptional regulatory sequences. In other embodiments, the ACTR donor sequence lacks a promoter. In some embodiments, the ACTR donor is inserted into a TCR β encoding gene (TCRB). In some embodiments insertion is achieved via targeted cleavage of the constant region of this gene (TCR β Constant region, or TRBC). In preferred embodiments, the ACTR donor is inserted into a TCR α encoding gene (TCRA). In further preferred embodiments insertion is achieved via targeted cleavage of the constant region of this gene (TCR α Constant region, abbreviated TRAC). In some embodiments, the donor is inserted into an exon sequence in TCRA, while in others, the donor is inserted into an intronic sequence in TCRA. In still further embodiments, the ACTR donor is inserted into a B2M gene. In some embodiments, the B2M and/or TCR-modulated cells further comprise a CAR. In still further embodiments, the B2M and/or TCR-modulated cells are additionally modulated at an HLA gene or a checkpoint inhibitor gene.

Also provided are pharmaceutical compositions comprising the modified cells as described herein (e.g., T cells or stem cells with inactivated TCR gene), or pharmaceutical compositions comprising one or more of the TCR and/or B2M gene binding molecules (e.g., engineered transcription factors and/or nucleases) as described herein. In certain embodiments, the pharmaceutical compositions further comprise one or more pharmaceutically acceptable excipients. The modified cells, TCR and/or B2M gene binding molecules (or polynucleotides encoding these molecules) and/or pharmaceutical compositions comprising these cells or molecules are introduced into the subject via methods known in the art, e.g., through intravenous infusion, infusion into a specific vessel such as the hepatic artery, or through direct tissue injection (e.g., muscle). In some embodiments, the subject is an adult human with a disease or condition that can be treated or ameliorated with the composition. In other embodiments, the subject is a pediatric subject where the composition is administered to prevent, treat or ameliorate the disease or condition (e.g., cancer, graft versus host disease, etc.).

In some aspects, the composition (TCR and/or B2M modulated cells comprising an ACTR) further comprises an exogenous antibody. See, also, U.S. Patent Publication No. 2017/0196992. In some aspects, the antibody is useful for arming an ACTR-comprising T cell to prevent or treat a condition. In some embodiments, the antibody recognizes an antigen associated with a tumor cell or with cancer associate processes such as EpCAM, CEA, gpA33, mucins, TAG-72, CAIX, PSMA, folate-binding antibodies, CD19, EGFR, ERBB2, ERBB3, MET, IGF1R, EPHA3, TRAILR1, TRAILR2, RANKL, FAP, VEGF, VEGFR, αVβ3 and α5β1 integrins, CD20, CD30, CD33, CD52, CTLA4, and enascin (Scott, et al. (2012) *Nat Rev Cancer* 12:278). In other embodiments, the antibody recognizes an antigen associated with an infectious disease such as HIV, HCV and the like.

In another aspect, provided herein are TCR gene DNA-binding domains (e.g., ZFPs, TALEs and sgRNAs) that bind to a target site in a TCR gene. In certain embodiments, the DNA binding domain comprises a ZFP with the recognition helix regions in the order as shown in a single row of Table 1; a TAL-effector domain DNA-binding protein with the RVDs that bind to a target site as shown in the first column of Table 1 or the third column of Table 2; and/or a sgRNA as shown in a single row of Table 2. These DNA-binding proteins can be associated with transcriptional regulatory domains to form engineered transcription factors that modulate TCR expression. Alternatively, these DNA-binding proteins can be associated with one or more nuclease domains to form engineered zinc finger nucleases (ZFNs), TALENs and/or CRISPR/Cas systems that bind to and cleave a TCR gene. In certain embodiments, the ZFNs, TALENs or single guide RNAs (sgRNA) of a CRISPR/Cas system bind to target sites in a human TCR gene. The DNA-binding domain of the transcription factor or nuclease (e.g., ZFP, TALE, sgRNA) may bind to a target site in a TCRA gene comprising 9, 10, 11, 12 or more (e.g., 13, 14, 15, 16, 17, 18, 19, 20 or more) nucleotides of any of the target sites shown herein (e.g., target sites of Table 1 or 2 as shown in SEQ ID NOs:8-21 and/or 92-103). The zinc finger proteins may include 1, 2, 3, 4, 5, 6 or more zinc fingers, each zinc finger having a recognition helix that specifically contacts a target subsite in the target gene. In certain embodiments, the zinc finger proteins comprise 4 or 5 or 6 fingers (designated F1, F2, F3, F4, F5 and F6 and ordered F1 to F4 or F5 or F6 from N-terminus to C-terminus), for example as shown in Table 1. The ZFPs as described herein may also include one or more mutations to phosphate contact residues of the zinc finger protein, for example, the nR-5Qabc mutant described in U.S. Patent Publication No. 2018/0087072. In other embodiments, the single guide RNAs or TAL-effector DNA-binding domains may bind to a target site as described herein (e.g., target sites of Table 1 or Table 2 or Table 6 as shown in any of SEQ ID NOs:8-21 and/or 92-103) or 12 or more base pairs within any of these target sites or between paired target sites. Exemplary sgRNA target sites are shown in Table 2 (SEQ ID NOs:92-103). sgRNAs that bind to 12 or more nucleotides of the target sites shown in Table 1 or Table 2 are also provided. TALENs may be designed to target sites as described herein (target sites of Table 1 or Table 2 or Table 6) using canonical or non-canonical RVDs as described in U.S. Pat. Nos. 8,586,526 and 9,458,205. The nucleases described herein (comprising a ZFP, a TALE or a sgRNA DNA-binding domain) are capable of making genetic modifications within a TCRA gene comprising any of SEQ ID NO:8-21 and/or 92-103, including modifications (insertions and/or deletions) within any of these sequences (SEQ ID NO:8-21 and/or 92-103) and/or modifications to TCRA gene sequences flanking the target site sequences shown in SEQ ID NO:8-21 and/or 92-103, for instance modifications within exonic sequences of a TCR gene within one or more of the following sequences: AACAGT, AGTGCT, CTCCT, TTGAAA, TGGACTT and AATCCTC.

In another aspect, provided herein are B2M gene DNA-binding domains (e.g., ZFPs, TALEs and sgRNAs) that bind to a target site in a B2M gene. In certain embodiments, the DNA binding domain comprises a ZFP with the recognition helix regions in the order as shown in a single row of Table 5 or Table 8 (columns labeled "designs", including the ZFPs of the ZFNs designated 72732; 72748; 68957; or 72678); a TAL-effector domain DNA-binding protein with the RVDs that bind to a target site as shown in the first column of Table 5 or Table 8; and/or a sgRNA that binds to a B2M target site as described herein (Table 5 or Table 8). These DNA-binding proteins can be associated with transcriptional regulatory domains to form engineered transcription factors that modulate B2M expression. Alternatively, these DNA-binding proteins can be associated with one or more nuclease (cleavage) domains to form engineered zinc finger nucleases (ZFNs), TALENs and/or CRISPR/Cas systems that bind to and cleave a B2M gene. In certain embodiments, the ZFNs, TALENs or single guide RNAs (sgRNA) of a CRISPR/Cas system bind to target sites in a human B2M gene. The DNA-binding domain of the transcription factor or nuclease (e.g., ZFP, TALE, sgRNA) may bind to a target site in a B2M gene comprising 9, 10, 11, 12 or more (e.g., 13, 14, 15, 16, 17, 18, 19, 20 or more) nucleotides of any of the target sites shown herein (e.g., Table 5 or Table 8 as shown in SEQ ID NOs: 117, 123, 126 or 127). The zinc finger proteins may include 1, 2, 3, 4, 5, 6 or more zinc fingers, each zinc finger having a recognition helix that specifically contacts a target subsite in the target gene. In certain embodiments, the zinc finger proteins comprise 4 or 5 or 6 fingers (designated F1, F2, F3, F4, F5 and F6 and ordered F1 to F4 or F5 or F6 from N-terminus to C-terminus), for example as shown in Table 5 or Table 8. The ZFPs as described herein may also include one or more mutations to phosphate contact residues of the zinc finger protein, for example, the nR-SQabc mutant described in U.S. Patent Publication No. 2018/0087072, including the ZFP designs (recognition helix regions and backbone mutants) of Table 8. In other embodiments, the single guide RNAs or TAL-effector DNA-binding domains may bind to a target site as described herein (e.g., target sites of Tables 5 or 8) or 12 or more base pairs within any of these target sites or between paired target sites. TALE domains may be designed to target sites as described herein (target sites of Tables 5 or 8) using canonical or non-canonical RVDs as described in U.S. Pat. Nos. 8,586,526 and 9,458,205. The nucleases described herein (comprising a ZFP, a TALE or a sgRNA DNA-binding domain) are capable of making genetic modifications within a B2M gene comprising any of the B2M target sites disclosed herein, including modifications (insertions and/or deletions) within any of these sequences and/or modifications to B2M gene sequences flanking the target site sequences shown in Tables 5 and 8 (SEQ ID NO:117, 123, 126 or 127).

Any of the nucleases described herein may comprise a DNA-binding domain (e.g., ZFP designs of Table 6 or 8, TALE or sgRNA) as described herein and a cleavage domain and/or a cleavage half-domain (e.g., a wild-type or engineered FokI cleavage half-domain). Thus, in any of the nucleases (e.g., ZFNs, TALENs, CRISPR/Cas systems) described herein, the nuclease domain may comprise a wild-type nuclease domain or nuclease half-domain (e.g., a FokI cleavage half domain). In other embodiments, the nucleases (e.g., ZFNs, TALENs, CRISPR/Cas nucleases) comprise engineered nuclease domains or half-domains, for example engineered FokI cleavage half domains that form obligate heterodimers. See, e.g., U.S. Pat. Nos. 7,914,796 and 8,034,598. In certain embodiments, one or more FokI endonuclease domains of the nucleases described herein may also comprise phosphate contact mutants (e.g., R416S and/or K525S) as described in U.S. Patent Publication No. 2018/0087072. Thus, the FokI domain of the nucleases described herein (e.g., ZFNs comprising: (i) ZFP designs as shown in Table 8, including ZFPs of the ZFNs designated 72732; 72748; 68957; or 72678 and (ii) a FokI domain) may include any combination of mutations to the FokI domain (positions numbered relative to full length FokI), including the wildtype FokI catalytic domain sequence, and also, but not limited to, the FokI domains indicated in Table 8, FokI-Sharkey (S418P+K441E); FokI ELD (Q→E at position 486, I→L at 499, N→D at position 496); FokI ELD, Sharkey (Q→E at position 486, I→L at position 499, N→D at position 496, S418P+K441E); FokI ELD, R416E (Q→E at position 486, I→L at position 499, N→D at position 496, R416E); FokI ELD, Sharkey, R416E (Q→E at position 486, I→L at position 499, N→D at position 496, S418P+K441E, R416E); FokI ELD, R416Y (Q→E at position 486, I→L at position 499, N→D at position 496, R416Y); FokI ELD, Sharkey, R416E (Q→E at position 486, I→L at position 499, N→D at position 496, S418P+K441E, R416E); FokI ELD, S418E (Q→E at position 486, I→L at position 499, N→D at position 496, S418E); FokI ELD, Sharkey partial, S418E (Q→E at position 486, I→L at position 499, N→D at position 496, K441E, S418E); FokI ELD, K525S (Q→E at position 486, I→L at position 499, N→D at position 496, K525S); FokI ELD, Sharkey K525S (Q→E at position 486, I→L at position 499, N→D at position 496, S418P+K441E, K525S); FokI ELD, I479T (Q→E at position 486, I→L at position 499, N→D at position 496, I479T); FokI ELD, Sharkey, I479T (Q→E at position 486, I→L at position 499, N→D at position 496, S418P+K441E, I479T); FokI ELD, P478D (Q→E at position 486, I→L at position 499, N→D at position 496, P478D); FokI ELD, Sharkey, P478D (Q→E at position 486, I→L at position 499, N→D at position 496, S418P+K441E, P478D); FokI ELD, Q481D (Q→E at position 486, I→L at position 499, N→D at position 496, Q481D); FokI ELD, Sharkey, Q481D (Q→E at position 486, I→L at position 499, N→D at position 496, S418P+K441E, Q481D); FokI KKR (E→K at position 490, I→K at position 538, H→R at position 537); FokI KKR Sharkey, (E→K at position 490, I→K at position 538, H→R at position 537, S418P+K441E); FokI KKR, Q481E (E→K at position 490, I→K at position 538, H→R at position 537, Q481E); FokI KKR, Sharkey Q481E (E→K at position 490, I→K at position 538, H→R at position 537, S418P+K441E, Q481E); FokI KKR, R416E (E→K at position 490, I→K at position 538, H→R at position 537, R416E); FokI KKR, Sharkey, R416E (E→K at position 490, I→K at position 538, H→R at position 537, S418P+K441E, R416E); FokI KKR, K525S (E→K at position 490, I→K at position 538, H→R at position 537, K525S); FokI KKR, Sharkey, K525S (E→K at position 490, I→K at position 538, H→R at position 537, S418P+K441E, K525S); FokI KKR, R416Y (E→K at position 490, I→K position 538, H→R at position 537, R416Y); FokI KKR, Sharkey, R416Y (E→K at position 490, I→K at position 538, H→R at position 537, S418P+K441E, R416Y); FokI, KKR I479T (E→K at position 490, I→K at position 538, H→R at position 537, I479T); FokI, KKR Sharkey I479T (E→K at position 490, I→K at position 538, H→R at position 537, S418P+K441E, I479T; FokI, KKR P478D (E→K at position 490, I→K at positions 538, H→R at position 537, P478D), FokI KKR Sharkey P478D(E→K at position 490, I→K at position 538, H→R at position 537, P478D); FokI DAD (R→D at position 487, N→D at position 496, I→A at position 499); FokI DAD Sharkey (R→D at position 487, N→D at position 496, I→A at position 499, S418P+K441E); FokI RVR (D→R at position 483, H→R at position 537, I→V at position 538); FokI RVR Sharkey (D→R at position 483, H→R at position 537, I→V at position 538, S418P+K441E). The ZFNs described herein may also include any linker sequence, including but not limited to sequences disclosed in U.S. Pat. Nos. 7,888, 121; 7,914,796; 8,034,598; 8,623,618; 9,567,609; and U.S. Publication No. 2017/0218349, which may be used between the N- or C-terminal of the DNA-binding domain (e.g., ZFP) and N- or C-terminal of the FokI cleavage domain.

In another aspect, the disclosure provides a polynucleotide encoding any of the proteins, fusion molecules and/or components thereof (e.g., sgRNA or other DNA-binding domain) described herein. The polynucleotide may be part of a viral vector, a non-viral vector (e.g., plasmid) or be in mRNA form. Any of the polynucleotides described herein may also comprise sequences (donor, homology arms or patch sequences) for targeted insertion into the TCR α and/or the TCR β gene. In yet another aspect, a gene delivery vector comprising any of the polynucleotides described herein is provided. In certain embodiments, the vector is an adenoviral vector (e.g., an Ad5/F35 vector) or a lentiviral vector (LV) including integration competent or integration-defective lentiviral vectors or an adeno-associated vector (AAV). Thus, also provided herein are viral vectors comprising a sequence encoding a nuclease (e.g., ZFN or TALEN) and/or a nuclease system (CRISPR/Cas or Ttago) and/or a donor sequence for targeted integration into a target gene. In some embodiments, the donor sequence and the sequences encoding the nuclease are on different vectors. In other embodiments, the nucleases are supplied as polypeptides. In preferred embodiments, the polynucleotides are mRNAs. In some aspects, the mRNA may be chemically modified (See e.g., Kormann, et al. (2011) *Nature Biotechnology* 29(2): 154-157). In other aspects, the mRNA may comprise an ARCA cap (see U.S. Pat. Nos. 7,074,596 and 8,153,773). In some aspects, the mRNA may comprise a cap introduced by enzymatic modification. The enzymatically introduced cap may comprise Cap0, Cap1 or Cap2 (see e.g., Smietanski, et al. (2014) *Nature Communications* 5:3004). In further aspects, the mRNA may be capped by chemical modification. In further embodiments, the mRNA may comprise a mixture of unmodified and modified nucleotides (see U.S. Patent Publication No. 2012/0195936). In still further embodiments, the mRNA may comprise a WPRE element (see U.S. Patent Publication No. 2016/0326548). In some embodiments, the mRNA is double stranded (See, e.g., Kariko, et al. (2011) *Nucl Acid Res* 39:e142).

In yet another aspect, the disclosure provides an isolated cell comprising any of the proteins, polynucleotides and/or vectors described herein. In certain embodiments, the cell is selected from the group consisting of a stem/progenitor cell, or a T-cell (e.g., effective or regulatory T-cell). In a still further aspect, the disclosure provides a cell or cell line which is descended from a cell or line comprising any of the nucleases, transcription factors, polynucleotides and/or vectors described herein, namely a cell or cell line descended (e.g., in culture) from a cell in which TCR and/or B2M has been inactivated by one or more ZFNs and/or in which a donor polynucleotide (e.g., ACTR and/or CAR) has been stably integrated into the genome of the cell. Thus, descendants of cells as described herein may not themselves comprise the molecule, polynucleotides and/or vectors described herein, but, in these cells, a TCR and/or B2M gene is inactivated and/or a donor polynucleotide is integrated into the genome and/or expressed.

In another aspect, described herein are methods of inactivating a TCR and/or B2M gene in a cell by introducing one or more proteins, polynucleotides and/or vectors into the cell as described herein. In certain embodiments, one or more polynucleotides encoding a ZFN (e.g., ZFN pair) as shown in Table 6 is used to modify the TCR gene in the cell and cells descended from these cells (including differentiated cells) comprise the modification(s). In other embodiments, one or more polynucleotide encoding a ZFN (e.g., ZFN pair) as shown in Table 8 is used to modify the B2M gene in the cell and cells descended from these (including differentiated cells) comprise the modification. In any of the methods described herein the nucleases may induce targeted mutagenesis, deletions of cellular DNA sequences, and/or facilitate targeted recombination at a predetermined chromosomal locus. Thus, in certain embodiments, the nucleases delete and/or insert one or more nucleotides from or into the target gene. In some embodiments a TCR and/or B2M gene is inactivated by nuclease cleavage followed by non-homologous end joining. In other embodiments, a genomic sequence in the target gene (e.g., TCR or B2M) is replaced, for example using a nuclease (or vector encoding said nuclease) as described herein and a "donor" sequence that is inserted into the gene following targeted cleavage with the nuclease. The donor sequence may be present in the nuclease vector, present in a separate vector (e.g., plasmid, linear single or double-stranded DNA, AAV, Ad or LV vector) or, alternatively, may be introduced into the cell using a different nucleic acid delivery mechanism. In some embodiments, the methods further comprise inactivating one or more additional genes (e.g., B2M) and/or integrating one or more transgenes into the genome of the cell, including, but not limited to, integration of one or more transgenes into the inactivated TCR and/or B2M gene and/or into one or more safe harbor genes. In certain embodiments, the methods described herein result in a population of cells in which at least 80-100% (or any value therebetween), including least 90-100% (or any value therebetween) of the cells include the knockout(s) and/or the integrated transgene(s).

Furthermore, any of the methods described herein can be practiced in vitro, in vivo and/or ex vivo. In certain embodiments, the methods are practiced ex vivo, for example to modify T-cells (effector or regulatory), to make them useful as therapeutics in an allogenic setting to treat a subject (e.g., a subject with cancer or autoimmune disease). Non-limiting examples of cancers that can be treated and/or prevented include lung carcinomas, pancreatic cancers, liver cancers, bone cancers, breast cancers, colorectal cancers, leukemias, ovarian cancers, lymphomas, brain cancers and the like. Non-limiting examples of autoimmune disease include transplant rejection, type 1 diabetes, irritable bowel disease/disorder, multiple sclerosis, lupus, scleroderma, rheumatoid arthritis and the like. The cells may also be used to induce immune tolerance.

In another aspect, described herein is a method of integrating one or more transgenes into a genome of an isolated cell, the method comprising: introducing, into the cell, (a) one or more donor vectors (e.g., plasmid, linear single or double-stranded DNA, AAVs, plasmids, Ads, mRNAs, etc.) comprising the one or more transgenes and (b) at least one non-naturally occurring nuclease in mRNA form, wherein the at least one nuclease cleaves the genome of the cell such that the one or more transgenes are integrated into the genome of the cell (e.g., into a TCR receptor), wherein the donor vector is introduced into introduced into the electroporation buffer comprising the isolated cell and the mRNA immediately before or immediately after electroporation of the nuclease into the cell. In certain embodiments, the donor vector is introduced into the electroporation buffer after electroporation and prior to transfer of the cells into a culture medium. See, e.g., U.S. Patent Publication Nos. 2015/0174169 and 2015/0110762. The methods may be used to introduce the transgene(s) into any genomic location, including, but not limited to, a TCR gene, a B2M gene and/or a safe harbor gene (e.g., AAVS1, Rosa, albumin, CCR5, CXCR4, etc.).

BRIEF DESCRIPTION OF THE DRAWINGS

FIGS. 1A and 1B are a depiction of the TCRA gene showing the locations of the sites targeted by the nucleases. FIG. 1A is an illustration of the processing of the TCRA gene from the germline form to that of a mature T cell and indicates the general target of the nucleases. FIG. 1B (SEQ ID NOs:116 (exon c1), 187(exon c2) and 118 (exon c3)) shows the regions between the target sites in the constant region sequence. The sequence shown in uppercase black lettering is the sequence of the indicated exon sequence, while the sequence in lowercase grey lettering is the adjoining intron sequence.

FIG. 3 depicts the percent of CD3 negative T cells following treatment with the TCRA-specific ZFN pairs as analyzed by FACS analysis.

FIGS. 5A through 5D are graphs depicting the growth of T cells following treatment with the TCRA-specific ZFN grouped according to the target site in the TCRA gene.

FIG. 6 shows results from TRAC (TCRA) and B2M double knockout and targeted integration of a donor into either the TRAC (TCRA) or B2M locus.

DETAILED DESCRIPTION

Figure 2A:
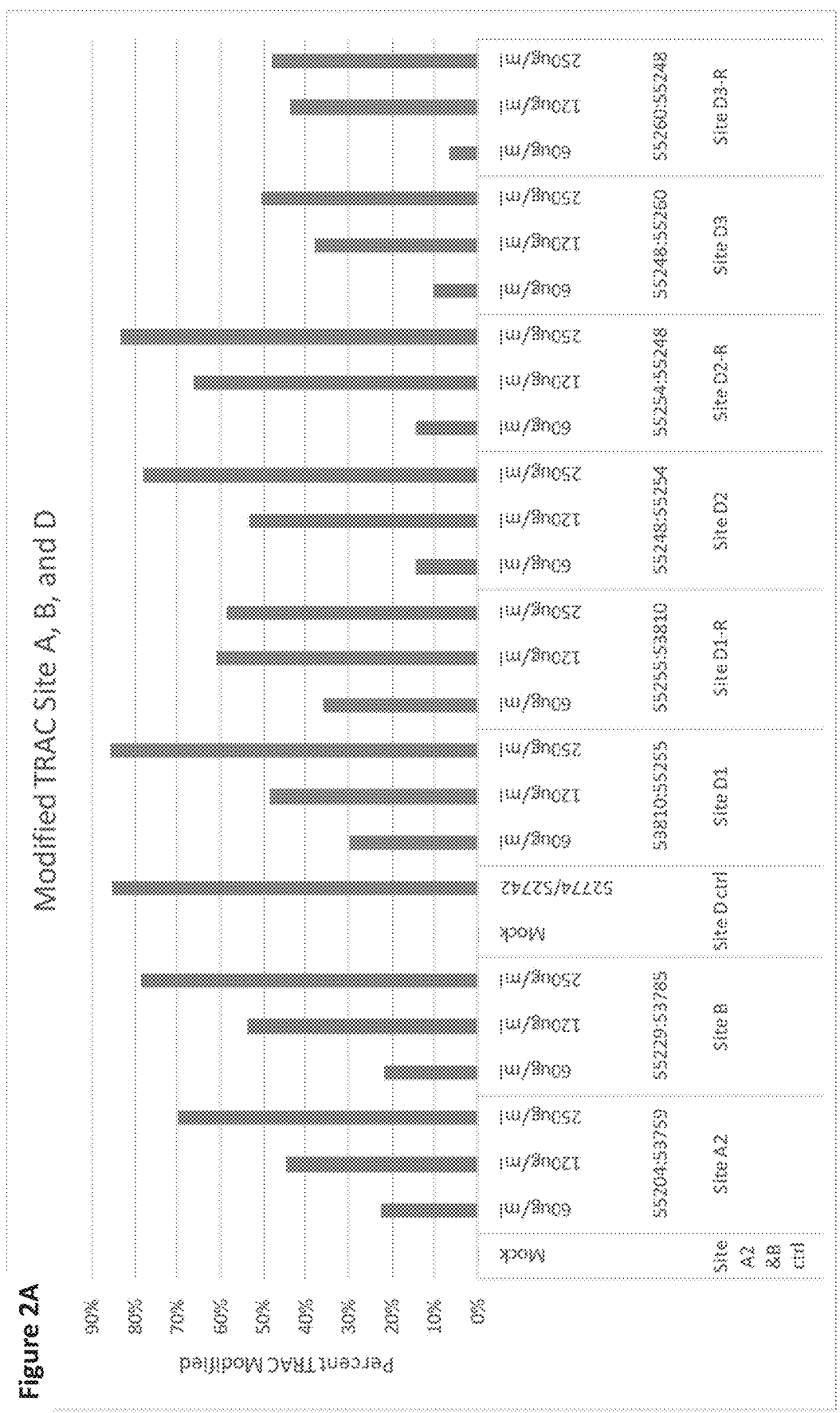
FIGS. 2A and 2B are graphs depicting the percent of each site modified in T cells treated with ZFNs specific for TCRA sites A, B and D (FIG. 2A) and sites E, F and G (FIG. 2B). Many of the pairs gave modification rates of 80% or greater.

Disclosed herein are compositions and methods for generating cells in which expression of a TCR gene is modulated such that the cells no longer comprise a TCR on their cell surfaces and/or in which expression of a B2M gene is modulated such that the cells no longer express B2M. Cells modified in this manner can be used as therapeutics, for example, transplants, as the lack of a TCR complex prevents or reduces an HLA-based immune response. Additionally, other genes of interest (e.g., transgenes) may be inserted into cells in which the TCR and/or B2M gene have been manipulated. One or more additional (non-TCR and/or B2M) genes (e.g., other TCR, B2M, PD1, CTLA4, HLA genes, safe harbor genes, etc.) may be modified via knock out and/or targeted insertion of exogenous sequences. Exogenous sequences can include chimeric antigen receptors for integration into the modified cells, which can be used to treat cancer and autoimmune disorders.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al., MOLECULAR CLONING: A LABORATORY MANUAL, Second edition, Cold Spring Harbor Laboratory Press, 1989 and Third edition, 2001; Ausubel et al., CUR- RENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$. "Non-specific binding" refers to, non-covalent interactions that occur between any molecule of interest (e.g., an engineered nuclease) and a macromolecule (e.g., DNA) that are not dependent on target sequence.

A "DNA binding molecule" is a molecule that can bind to DNA. Such DNA binding molecule can be a polypeptide, a domain of a protein, a domain within a larger protein or a polynucleotide. In some embodiments, the polynucleotide is DNA, while in other embodiments, the polynucleotide is RNA. In some embodiments, the DNA binding molecule is a protein domain of a nuclease (e.g., the FokI domain), while in other embodiments, the DNA binding molecule is a guide RNA component of an RNA-guided nuclease (e.g., Cas9 or Cfp1).

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. Thus, each zinc finger of a multi-finger ZFP includes a recognition helix region for binding to DNA within a backbone. The term zinc finger DNA binding protein is often abbreviated as zinc finger protein or ZFP. The term "zinc finger nuclease" includes one ZFN as well as a pair of ZFNs (the members of the pair are referred to as "left and right" or "first and second" or "pair") that dimerize to cleave the target gene.

A "TALE DNA binding domain" or "TALE" is a polypeptide comprising one or more TALE repeat domains/units. The repeat domains, each comprising a repeat variable diresidue (RVD), are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. TALE proteins may be designed to bind to a target site using canonical or non-canonical RVDs within the repeat units. See, e.g., U.S. Pat. Nos. 8,586,526 and 9,458,205. Zinc finger and TALE DNA-binding domains can be "engineered" to bind to a predetermined nucleotide sequence, for example via engineering (altering one or more amino acids) of the recognition helix region of a naturally occurring zinc finger protein or by engineering of the amino acids involved in DNA binding (the repeat variable diresidue or RVD region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs (canonical and non-canonical RVDs) and binding data. See, for example, U.S. Pat. Nos. 9,458,205; 8,586,526; 6,140,081; 6,453,242; and 6,534,261; see also International Patent Publication Nos. WO 98/53058; WO 98/53059; WO 98/53060; WO 02/16536; and WO 03/016496. The term "TALEN" includes one TALEN as well as a pair of TALENs (the members of the pair are referred to as "left and right" or "first and second" or "pair") that dimerize to cleave the target gene.

A "selected" zinc finger protein, TALE protein or CRISPR/Cas system is not found in nature and whose production results primarily from an empirical process such as phage display, interaction trap or hybrid selection. See e.g., U.S. Pat. Nos. 5,789,538; 5,925,523; 6,007,988; 6,013,453; 6,200,759 and International Patent Publication Nos. WO 95/19431; WO 96/06166; WO 98/53057; WO 98/54311; WO 00/27878; WO 01/60970; WO 01/88197; and WO 02/099084.

"TtAgo" is a prokaryotic Argonaute protein thought to be involved in gene silencing. TtAgo is derived from the bacteria *Thermus thermophilus*. See, e.g., Swarts, et al., ibid, G. Sheng, et al. (2013) *Proc. Natl. Acad. Sci. U.S.A.* 111, 652). A "TtAgo system" is all the components required including e.g., guide DNAs for cleavage by a TtAgo enzyme.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break (DSB) in the target sequence (e.g., cellular chromatin) at a predetermined site (e.g., a gene or locus of interest), and a "donor" polynucleotide, having homology to the nucleotide sequence in the region of the break, can be introduced into the cell. The presence of the DSB has been shown to facilitate integration of the donor sequence. Optionally, the construct has homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,888,121; 7,914,796; 8,034,598; 8,623,618 and U.S. Patent Publication No. 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5' GAATTC 3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. See, e.g., U.S. Pat. Nos. 8,703,489 and 9,255,259. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid. The term also includes systems in which a polynucleotide component associates with a polypeptide component to form a functional molecule (e.g., a CRISPR/Cas system in which a single guide RNA associates with a functional domain to modulate gene expression).

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci that are targeted by nuclease(s) include CCR5, CCR5, HPRT, AAVS1, Rosa and albumin. See, e.g., U.S. Pat. Nos. 8,771, 985; 8,110,379; 7,951,925; U.S. Patent Publication Nos. 2010/0218264; 2011/0265198; 2013/0137104; 2013/0122591; 2013/0177983; 2013/0177960; 2015/0056705; and 2015/0159172).

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. "Modulation" or "modification" of gene expression refers to a change in the activity of a gene. Modulation of expression can include, but is not limited to, gene activation and gene repression, including by modification of the gene via binding of an exogenous molecule (e.g., engineered transcription factor). Modulation may also be achieved by modification of the gene sequence via genome editing (e.g., cleavage, alteration, inactivation, random mutation). Gene inactivation refers to any reduction in gene expression as compared to a cell that has not been modified as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a DNA-binding domain (e.g., ZFP, TALE) is fused to an activation domain, the DNA-binding domain and the activation domain are in operative linkage if, in the fusion polypeptide, the DNA-binding domain portion is able to bind its target site and/or its binding site, while the activation domain is able to up-regulate gene expression. When a fusion polypeptide in which a DNA-binding domain is fused to a cleavage domain, the DNA-binding domain and the cleavage domain are in operative linkage if, in the fusion polypeptide, the DNA-binding domain portion is able to bind its target site and/or its binding site, while the cleavage domain is able to cleave DNA in the vicinity of the target site. Similarly, with respect to a fusion polypeptide in which a DNA-binding domain is fused to an activation or repression domain, the DNA-binding domain and the activation or repression domain are in operative linkage if, in the fusion polypeptide, the DNA-binding domain portion is able to bind its target site and/or its binding site, while the activation domain is able to upregulate gene expression or the repression domain is able to downregulate gene expression.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel, et al., supra. The ability of a protein to interact with another protein can be determined, for example, by co-immunoprecipitation, two-hybrid assays or complementation, both genetic and biochemical. See, for example, Fields, et al. (1989) *Nature* 340:245-246; U.S. Pat. No. 5,585,245 and International Patent Publication No. WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the expression cassettes of the invention can be administered. Subjects of the present invention include those with a disorder or those at risk for developing a disorder.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Cancer and graft versus host disease are non-limiting examples of conditions that may be treated using the compositions and methods described herein. Thus, "treating" and "treatment" includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to effect treatment in the mammal, preferably a human. The amount of a composition of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

DNA-Binding Domains

Described herein are compositions comprising a DNA-binding domain that specifically binds to a target site in any gene comprising a HLA gene or a HLA regulator. Any DNA-binding domain can be used in the compositions and methods disclosed herein, including but not limited to a zinc finger DNA-binding domain, a TALE DNA binding domain, the DNA-binding portion (sgRNA) of a CRISPR/Cas nuclease, or a DNA-binding domain from a meganuclease. The DNA-binding domain may bind to any target sequence within the gene, including, but not limited to, a target sequence of 12 or more nucleotides as shown in any of target sites disclosed herein (SEQ ID NO:8-21 and/or 92-103).

In certain embodiments, the DNA binding domain comprises a zinc finger protein. Preferably, the zinc finger protein is non-naturally occurring in that it is engineered to bind to a target site of choice. See, for example, Beerli, et al. (2002) Nature Biotechnol. 20:135-141; Pabo, et al. (2001) Ann. Rev. Biochem. 70:313-340; Isalan, et al. (2001) Nature Biotechnol. 19:656-660; Segal, et al. (2001) Curr. Opin. Biotechnol. 12:632-637; Choo, et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; and 7,253,273; and U.S. Patent Publication Nos. 2005/0064474; 2007/0218528; and 2005/0267061, all incorporated herein by reference in their entireties. In certain embodiments, the DNA-binding domain comprises a zinc finger protein disclosed in U.S. Patent Publication No. 2012/0060230 (e.g., Table 1), incorporated by reference in its entirety herein. In other embodiments, the DNA-binding domain comprises the ZFP component (referred to as "designs") and including recognition helix regions and backbones as set forth in the ZFNs of Tables 1, 2, 4, 5, 6 or 8, including but not limited to the ZFP domains of ZFNs 72732; 72748; 68957; or 72678.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; and WO 01/88197 and GB 2,338,237. In addition, enhancement of binding specificity for zinc finger binding domains has been described, for example, in U.S. Pat. No. 6,794,136.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; and International Patent Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/16536; and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; 7,153,949; 7,888,121; 7,914,796; 8,034,598; 8,623,618; 9,567,609; and U.S. Patent Publication No. 2017/0218349 for exemplary linker sequences. The proteins described herein may include any combination of suitable linkers between the individual zinc fingers of the protein.

In certain embodiments, the DNA-binding domain is an engineered zinc finger protein that binds (in a sequence-specific manner) to a target site in a TCR gene or TCR regulatory gene and modulates expression of a TCR gene. In some embodiments, the zinc finger protein binds to a target site in TCRA, while in other embodiments, the zinc finger binds to a target site in TRBC. In other embodiments, the DNA-binding domain is an engineered zinc finger protein that binds (in a sequence-specific manner) to a target site in a B2M gene and modulates expression of a B2M gene. Non-limiting exemplary embodiments of these DNA-binding domains are shown in Tables 1, 2 and 6 (TCR) and Tables 5 and 8 (B2M). In certain embodiments, the ZFP comprises the ZFP portion of the ZFNs designated 72732; 72748; 68957; or 72678.

Usually, the ZFPs include at least three fingers. Certain of the ZFPs include four, five or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains.

In some embodiments, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort, et al. (1997) *Nucleic Acids Res.* 25:3379-3388; Dujon, et al. (1989) *Gene* 82:115-118; Perler, et al. (1994) *Nucleic Acids Res.* 22, 1125-1127; Jasin (1996) *Trends Genet.* 12:224-228; Gimble, et al. (1996) *J. Mol. Biol.* 263:163-180; Argast, et al. (1998) *J. Mol. Biol.* 280: 345-353 and the New England Biolabs catalogue. In addition, the DNA-binding specificity of homing endonucleases and meganucleases can be engineered to bind non-natural target sites. See, for example, Chevalier, et al. (2002) *Molec. Cell* 10:895-905; Epinat, et al. (2003) *Nucleic Acids Res.* 31:2952-2962; Ashworth, et al. (2006) *Nature* 441:656-659; Pâques, et al. (2007) *Current Gene Therapy* 7:49-66; U.S. Patent Publication No. 2007/0117128.

In other embodiments, the DNA binding domain comprises an engineered domain from a TAL effector similar to those derived from the plant pathogens *Xanthomonas* (see Boch, et al. (2009) *Science* 326: 1509-1512 and Moscou and Bogdanove (2009) *Science* 326:1501) and *Ralstonia* (see Heuer, et al. (2007) *Applied and Environmental Microbiology* 73(13): 4379-4384); U.S. Patent Publication Nos. 2011/0301073 and 2011/0145940. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like effectors (TALE) which mimic plant transcriptional activators and manipulate the plant transcriptome (see Kay, et al. (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas, et al. (1989) *Mol Gen Genet* 218: 127-136 and International Patent Publication No. WO 2010/079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S., et al. (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer, et al. (2007) *Appl and Envir Micro* 73(13):4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TAL effectors depends on the sequences found in the tandem repeats. The repeated sequence comprises approximately 102 base pairs and the repeats are typically 91-100% homologous with each other (Bonas, et al., ibid). Polymorphism of the repeats is usually located at positions 12 and 13 and there appears to be a one-to-one correspondence between the identity of the hypervariable diresidues (the repeat variable diresidue or RVD region) at positions 12 and 13 with the identity of the contiguous nucleotides in the TAL-effector's target sequence (see Moscou and Bogdanove (2009) *Science* 326: 1501 and Boch, et al. (2009) *Science* 326:1509-1512). Experimentally, the natural code for DNA recognition of these TAL-effectors has been determined such that an HD sequence at positions 12 and 13 (Repeat Variable Diresidue or RVD) leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch, et al., ibid). Engineered TAL proteins have been linked to a FokI cleavage half domain to yield a TAL effector domain nuclease fusion (TALEN), including TALENs with atypical RVDs. See, e.g., U.S. Pat. No. 8,586,526.

In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel, et al. (2013) *Nucl Acid Res:* 1-13, doi: 10.1093/nar/gkt1224).

In still further embodiments, the nuclease comprises a compact TALEN. These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley, et al. (2013) *Nat Comm* 4:1762 DOI: 10.1038/ncomms2782). In addition, the nuclease domain may also exhibit DNA-binding functionality. Any TALENs may be used in combination with additional TALENs (e.g., one or more TALENs (cTALENs or FokI-TALENs) with one or more mega-TALEs.

In addition, as disclosed in these and other references, zinc finger domains and/or multi-fingered zinc finger proteins or TALEs may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136.

In certain embodiments, the DNA-binding domain is part of a CRISPR/Cas nuclease system, including a single guide RNA (sgRNA) that binds to DNA. See, e.g., U.S. Pat. No. 8,697,359 and U.S. Patent Publication Nos. 2015/0056705 and 2015/0159172. The CRISPR (clustered regularly interspaced short palindromic repeats) locus, which encodes RNA components of the system, and the cas (CRISPR-associated) locus, which encodes proteins (Jansen, et al. (2002) *Mol. Microbiol.* 43:1565-1575; Makarova, et al. (2002) *Nucleic Acids Res.* 30:482-496; Makarova, et al. (2006) *Biol. Direct* 1:7; Haft, et al. (2005) *PLoS Comput. Biol.* 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs functional domain (e.g., nuclease such as Cas) to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof such as derivative Cas proteins. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran, et al. (2015) Nature 520:186).

In some embodiments, the DNA binding domain is part of a TtAgo system (see Swarts, et al., ibid; Sheng, et al., ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan, et al. (2005) *Mol. Cell* 19, 405; Olovnikov, et al. (2013) *Mol. Cell* 51:594; Swarts, et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts, et al., ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olovnikov, et al., ibid).

Exogenous guide DNAs of arbitrary DNA sequence can be loaded onto the TtAgo protein (Swarts, et al., ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37° C. Ago-RNA-mediated DNA cleavage could be used to affect a panopoly of outcomes including gene knock-out, targeted gene addition, gene correction, targeted gene deletion using techniques standard in the art for exploitation of DNA breaks.

Thus, any DNA-binding domain can be used.

Fusion Molecules

Fusion molecules comprising DNA-binding domains (e.g., ZFPs or TALEs, CRISPR/Cas components such as single guide RNAs) as described herein associated with a heterologous regulatory (functional) domain (or functional fragment thereof) are also provided. Common domains include, e.g., transcription factor domains (activators, repressors, co-activators, co-repressors), silencers, onco-genes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g., kinases, acetylases and deacetylases); and DNA modifying enzymes (e.g., methyltransferases, topoisomerases, helicases, ligases, kinases, phosphatases, polymerases, endonucleases) and their associated factors and modifiers. Such fusion molecules include transcription factors comprising the DNA-binding domains described herein and a transcriptional regulatory domain as well as nucleases comprising the DNA-binding domains and one or more nuclease domains.

Suitable domains for achieving activation (transcriptional activation domains) include the HSV VP16 activation domain (see, e.g., Hagmann, et al. (1997) *J Virol.* 71:5952-5962) nuclear hormone receptors (see, e.g., Torchia, et al. (1998) *Curr. Opin. Cell. Biol.* 10:373-383); the p65 subunit of nuclear factor kappa B (Bitko & Barik (1998) *J. Virol.* 72:5610-5618 and Doyle & Hunt (1997) *Neuroreport* 8:2937-2942); Liu, et al. (1998) *Cancer Gene Ther.* 5:3-28), or artificial chimeric functional domains such as VP64 (Beerli, et al. (1998) *Proc. Natl. Acad. Sci. USA* 95:14623-33), and degron (Molinari, et al. (1999) *EMBO J.* 18, 6439-6447). Additional exemplary activation domains include, Oct 1, Oct-2A, Spl, AP-2, and CTF1 (Seipel, et al. (1992) *EMBO J.* 11, 4961-4968 as well as p300, CBP, PCAF, SRC1 PvALF, AtHD2A and ERF-2. See, for example, Robyr, et al. (2000) *Mol. Endocrinol.* 14:329-347; Collingwood, et al. (1999) *J. Mol. Endocrinol.* 23:255-275; Leo, et al. (2000) *Gene* 245:1-11; Manteuffel-Cymborowska (1999) *Acta Biochim. Pol.* 46:77-89; McKenna, et al. (1999) *J. Steroid Biochem. Mol. Biol.* 69:3-12; Malik, et al. (2000) *Trends Biochem. Sci.* 25:277-283; and Lemon, et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB 1. See, for example, Ogawa, et al. (2000) *Gene* 245:21-29; Okanami, et al. (1996) *Genes Cells* 1:87-99; Goff, et al. (1991) *Genes Dev.* 5:298-309; Cho, et al. (1999) *Plant Mol. Biol.* 40:419-429; Ulmason, et al. (1999) *Proc. Natl. Acad. Sci. USA* 96:5844-5849; Sprenger-Haussels, et al. (2000) *Plant J.* 22:1-8; Gong, et al. (1999) *Plant Mol. Biol.* 41:33-44; and Hobo, et al. (1999) *Proc. Natl. Acad. Sci. USA* 96:15,348-15,353.

It will be clear to those of skill in the art that, in the formation of a fusion protein (or a nucleic acid encoding same) between a DNA-binding domain and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in U.S. Pat. No. 7,053,264.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird, et al. (1999) *Cell* 99:451-454; Tyler, et al. (1999) *Cell* 99:443-446; Knoepfler, et al. (1999) *Cell* 99:447-450; and Robertson, et al. (2000) *Nature Genet.* 25:338-342. Additional exemplary repression domains include, but are not limited to, ROM2 and AtHD2A. See, for example, Chem, et al. (1996) *Plant Cell* 8:305-321; and Wu, et al. (2000) *Plant J.* 22:19-27.

Fusion molecules are constructed by methods of cloning and biochemical conjugation that are well known to those of skill in the art. Fusion molecules comprise a DNA-binding domain (e.g., ZFP, TALE, sgRNA) associated with a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp, et al. (2000) *Proc. Natl. Acad. Sci. USA* 97:3930-3935. Furthermore, single guide RNAs of the CRISPR/Cas system associate with functional domains to form active transcriptional regulators and nucleases.

In certain embodiments, the target site is present in an accessible region of cellular chromatin. Accessible regions can be determined as described, for example, in U.S. Pat. Nos. 7,217,509 and 7,923,542. If the target site is not present in an accessible region of cellular chromatin, one or more accessible regions can be generated as described in U.S. Pat. Nos. 7,785,792 and 8,071,370. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3) (Cordingley, et al. (1987) *Cell* 48:261-270; Pina, et al. (1990) *Cell* 60:719-731; and Cirillo, et al. (1998) *EMBO J.* 17:244-254).

The fusion molecule may be formulated with a pharmaceutically acceptable carrier, as is known to those of skill in the art. See, for example, Remington's Pharmaceutical Sciences, 17th ed., 1985; and U.S. Pat. Nos. 6,453,242 and 6,534,261.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Additional exemplary functional domains are disclosed, for example, in U.S. Pat. Nos. 6,534,261 and 6,933,113.

Functional domains that are regulated by exogenous small molecules or ligands may also be selected. For example, RheoSwitch® technology may be employed wherein a functional domain only assumes its active conformation in the presence of the external RheoChem™ ligand (see for example U.S. Patent Publication No. 2009/0136465). Thus, the ZFP may be operably linked to the regulatable functional domain wherein the resultant activity of the ZFP-TF is controlled by the external ligand.

Nucleases

In certain embodiments, the fusion molecule comprises a DNA-binding binding domain associated with a cleavage (nuclease) domain. As such, gene modification can be achieved using a nuclease, for example an engineered nuclease. Engineered nuclease technology is based on the engineering of naturally occurring DNA-binding proteins. For example, engineering of homing endonucleases with tailored DNA-binding specificities has been described. Chames, et al. (2005) *Nucleic Acids Res* 33(20):e178; Arnould, et al. (2006)*J. Mol. Biol.* 355:443-458. In addition, engineering of ZFPs has also been described. See, e.g., U.S. Pat. Nos. 6,534,261; 6,607,882; 6,824,978; 6,979,539; 6,933,113; 7,163,824; and 7,013,219.

In addition, ZFPs and/or TALEs can be fused to nuclease domains to create ZFNs and TALENs—a functional entity that is able to recognize its intended nucleic acid target through its engineered (ZFP or TALE) DNA binding domain and cause the DNA to be cut near the DNA binding site via the nuclease activity.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

In any of the nucleases described herein, the nuclease can comprise an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526). In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel, et al. (2013) *Nucl Acid Res:* 1-13, doi: 10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley, et al. (2013) *Nat Comm:* 1-8 DOI: 10.1038/ncomms2782). Any TALENs may be used in combination with additional TALENs (e.g., one or more TALENs (cTALENs or FokI-TALENs) with one or more mega-TALs) or other DNA cleavage enzymes.

In certain embodiments, the nuclease comprises a meganuclease (homing endonuclease) or a portion thereof that exhibits cleavage activity. Naturally-occurring meganucleases recognize 15-40 base-pair cleavage sites and are commonly grouped into four families: the LAGLIDADG family ("LAGLIDADG" disclosed as SEQ ID NO: 122), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort, et al. (1997) *Nucleic Acids Res.* 25:3379-3388; Dujon, et al. (1989) *Gene* 82:115-118; Perler, et al. (1994) *Nucleic Acids Res.* 22:1125-1127; Jasin (1996) *Trends Genet.* 12:224-228; Gimble, et al. (1996) *J. Mol. Biol.* 263:163-180; Argast, et al. (1998) *J. Mol. Biol.* 280: 345-353 and the New England Biolabs catalogue.

DNA-binding domains from naturally-occurring meganucleases, primarily from the LAGLIDADG family ("LAGLIDADG" disclosed as SEQ ID NO: 122), have been used to promote site-specific genome modification in plants, yeast, *Drosophila*, mammalian cells and mice, but this approach has been limited to the modification of either homologous genes that conserve the meganuclease recognition sequence (Monet, et al. (1999), *Biochem. Biophysics. Res. Common.* 255: 88-93) or to pre-engineered genomes into which a recognition sequence has been introduced (Route, et al. (1994), *Mol. Cell. Biol.* 14:8096-106; Chilton, et al. (2003), *Plant Physiology.* 133:956-65; Puchta, et al. (1996), *Proc. Natl. Acad. Sci. USA* 93:5055-60; Rong, et al. (2002), *Genes Dev.* 16:1568-81; Gouble, et al. (2006), *J. Gene Med.* 8(5):616-622). Accordingly, attempts have been made to engineer meganucleases to exhibit novel binding specificity at medically or biotechnologically relevant sites (Porteus, et al. (2005), *Nat. Biotechnol.* 23:967-73; Sussman, et al. (2004), *J. Mol. Biol.* 342:31-41; Epinat, et al. (2003) *Nucleic Acids Res.* 31:2952-62; Chevalier, et al. (2002) *Molec. Cell* 10:895-905; Epinat, et al. (2003) *Nucleic Acids Res.* 31:2952-2962; Ashworth, et al. (2006) *Nature* 441:656-659; Paques, et al. (2007) *Current Gene Therapy* 7:49-66; U.S. Patent Publication Nos. 2007/0117128; 2006/0206949; 2006/0153826; 2006/0078552; and 2004/0002092). In addition, naturally-occurring or engineered DNA-binding domains from meganucleases can be operably linked with a cleavage domain from a heterologous nuclease (e.g., FokI) and/or cleavage domains from meganucleases can be operably linked with a heterologous DNA-binding domain (e.g., ZFP or TALE).

In other embodiments, the nuclease is a zinc finger nuclease (ZFN) or TALE DNA binding domain-nuclease fusion (TALEN). ZFNs and TALENs comprise a DNA binding domain (zinc finger protein or TALE DNA binding domain) that has been engineered to bind to a target site in a gene of choice and cleavage domain or a cleavage half-domain (e.g., from a restriction and/or meganuclease as described herein).

As described in detail above, zinc finger binding domains and TALE DNA binding domains can be engineered to bind to a sequence of choice. See, for example, Beerli, et al. (2002) *Nature Biotechnol.* 20:135-141; Pabo, et al. (2001) *Ann. Rev. Biochem.* 70:313-340; Isalan, et al. (2001) *Nature Biotechnol.* 19:656-660; Segal, et al. (2001) *Curr. Opin. Biotechnol.* 12:632-637; Choo, et al. (2000) *Curr. Opin. Struct. Biol.* 10:411-416. An engineered zinc finger binding domain or TALE protein can have a novel binding specificity, compared to a naturally-occurring protein. Engineering methods include, but are not limited to, rational design and various types of selection. Rational design includes, for example, using databases comprising triplet (or quadruplet) nucleotide sequences and individual zinc finger or TALE amino acid sequences, in which each triplet or quadruplet nucleotide sequence is associated with one or more amino acid sequences of zinc fingers or TALE repeat units which bind the particular triplet or quadruplet sequence. See, for example, U.S. Pat. Nos. 6,453,242 and 6,534,261, incorporated by reference herein in their entireties. In certain embodiments, the DNA-binding domains comprise ZFPs derived from (e.g., the ZFP component) of the ZFNs designated 68957, 72678, 72732, 72748 (B2M) or 68846 (TCR).

Selection of target sites; and methods for design and construction of fusion proteins (and polynucleotides encoding same) are known to those of skill in the art and described in detail in U.S. Pat. Nos. 7,888,121 and 8,409,861, incorporated by reference in their entireties herein.

In addition, as disclosed in these and other references, zinc finger domains, TALEs and/or multi-fingered zinc finger proteins may be linked together using any suitable linker sequences, including for example, linkers of 5 or more amino acids in length. See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. See, also, U.S. Pat. No. 8,772,453.

Thus, nucleases such as ZFNs, TALENs and/or meganucleases can comprise any DNA-binding domain and any nuclease (cleavage) domain (cleavage domain, cleavage half-domain). As noted above, the cleavage domain may be heterologous to the DNA-binding domain, for example a zinc finger or TAL-effector DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort, et al. (1997) Nucleic Acids Res. 25:3379-3388. Additional enzymes which cleave DNA are known (e.g., S1 Nuclease; mung bean nuclease; pancreatic DNase I; micrococcal nuclease; yeast HO endonuclease; see also Linn, et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites, but may lie 1 or more kilobases away from the cleavage site, including between 1-50 base pairs (or any value therebetween including 1-5, 1-10, and 1-20 base pairs), 1-100 base pairs (or any value therebetween), 100-500 base pairs (or any value therebetween), 500 to 1000 base pairs (or any value therebetween) or even more than 1 kb from the cleavage site.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li, et al. (1992) Proc. Natl. Acad. Sci. USA 89:4275-4279; Li, et al. (1993) Proc. Natl. Acad. Sci. USA 90:2764-2768; Kim, et al. (1994a) Proc. Natl. Acad. Sci. USA 91:883-887; Kim, et al. (1994b)J. Biol. Chem. 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite, et al. (1998) Proc. Natl. Acad. Sci. USA 95:10,570-10,575. The sequence of the full-length FokI is shown below. The cleavage domain used in the nucleases described herein is shown in italics and underlining (positions 384 to 579 of the full-length protein) where the holo protein sequence is described below (SEQ ID NO: 138):

```
                                          (SEQ ID NO: 138)
MVSKIRTFGWVQNPGKFENLKRVVQVFDRNSKVHNEVKNIKIPTLVKESK

IQKELVAIMNQHDLIYTYKELVGTGTSIRSEAPCDAIIQATIADQGNKKG

YIDNWSSDGFLRWAHALGFIEYINKSDSFVITDVGLAYSKSADGSAIEKE

ILIEAISSYPPAIRILTLLEDGQHLTKFDLGKNLGFSGESGFTSLPEGIL

LDTLANAMPKDKGEIRNNWEGSSDKYARMIGGWLDKLGLVKQGKKEFIIP

TLGKPDNKEFISHAFKITGEGLKVLRRAKGSTKFTRVPKRVYWEMLATNL

TDKEYVRTRRALILEILIKAGSLKIEQIQDNLKKLGFDEVIETIENDIKG

LINTGIFIEIKGRFYQLKDHILQFVIPNRGVTKQLVKSELEEKKSELRHK

LKYVPHEYIELIEIARNSTQDRILEMKVMEFFMKVYGYRGKHLGGSRKPD

GAIYTVGSPIDYGVIVDTKAYSGGYNLPIGQADEMQRYVEENQTRNKHIN

PNEWWKVYPSSVTEFKFLFVSGHFKGNYKAQLTRLNHITNCNGAVLSVEE

LLIGGEMIKAGTLTLEEVRRKFNNGEINF
```

Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Patent Publication No. WO 07/014275, incorporated herein in its entirety. Additional restriction enzymes also contain separable binding and cleavage domains, and these are contemplated by the present disclosure. See, for example, Roberts, et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 7,914,796; 8,034,598; and 8,623,618; and U.S. Patent Publication No. 2011/0201055, the disclosures of all of which are incorporated by reference in their entireties herein. "Sharkey" mutations (e.g., 418 and 441, numbered relative to full-length) and additional mutations, for example, to residue 416 (e.g., R416S) and/or residue 525 (e.g., K525S) as described in U.S. Patent Publication No. 2018/0087072, may also be included. Thus, the FokI cleavage domains used in the nucleases of the invention may be mutated at one or more of the following amino acid residues positions (numbered relative to full length): 416, 418, 441, 446, 447, 479, 483, 484, 486, 487, 490, 491, 496, 498, 499, 500, 525, 531, 534, 537, and/or 538.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Pat. Nos. 7,914,796 and 8,034,598, the disclosures of which are incorporated by reference in their entireties for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively).

In other embodiments, the engineered cleavage half-domain comprises mutations at positions 487, 499 and 496 (numbered relative to wild-type FokI), for instance mutations that replace the wild-type Arg (R) residue at position 487 with an Asp (D) residue and the wild-type Ile (I) residue at position 499 with an Ala (A) and the wild-type Asn (N) residue at position 496 with an Asp (D) residue (also referred to as "DAD") and/or mutations at positions 483, 538 and 537 (numbered relative to wild-type FokI), for instance, mutations that replace the wild-type Asp (D) residue at position 483 with an Arg (R) residue and the wild-type Ile (I) residue at position 538 with a Val (V) residue, and the wild-type His (H) residue at position 537 with an Arg (R) residue (also referred to as "RVR"). See, e.g., U.S. Pat. Nos. 8,962,281; 7,914,796; 8,034,598; and 8,623,618, the disclosures of which are incorporated by reference in its entirety for all purposes. In other embodiments, the engineered cleavage half domain comprises the "Sharkey" and/or "Sharkey" mutations (see Guo, et al. (2010) *J. Mol. Biol.* 400(1):96-107).

Thus, non-limiting examples of FokI domains that can be used in the nucleases described herein include: Fok mutants shown in Table 8 (e.g., ELD, KKR, etc.), FokI-Sharkey (S418P+K441E), FokI ELD (Q→E at position 486, I→L at 499, N→D at position 496), FokI ELD, Sharkey (Q→E at position 486, I→L at position 499, N→D at position 496, S418P+K441E), FokI ELD, R416E (Q→E at position 486, I→L at position 499, N→D at position 496, R416E), FokI ELD, Sharkey, R416E (Q→E at position 486, I→L at position 499, N→D at position 496, S418P+K441E, R416E), FokI ELD, R416Y (Q→E at position 486, I→L at position 499, N→D at position 496, R416Y), FokI ELD, Sharkey, R416E (Q→E at position 486, I→L at position 499, N→D at position 496, S418P+K441E, R416E), FokI ELD, S418E (Q→E at position 486, I→L at position 499, N→D at position 496, S418E), FokI ELD, Sharkey partial, S418E (Q→E at position 486, I→L at position 499, N→D at position 496, K441E, S418E), FokI ELD, K525S (Q→E at position 486, I→L at position 499, N→D at position 496, K525S), FokI ELD, Sharkey K525S (Q→E at position 486, I→L at position 499, N→D at position 496, S418P+K441E, K525S), FokI ELD, I479T (Q→E at position 486, I→L at position 499, N→D at position 496, I1479T), FokI ELD, Sharkey, I479T (Q→E at position 486, I→L at position 499, N→D at position 496, S418P+K441E, I479T), FokI ELD, P478D (Q→E at position 486, I→L at position 499, N→D at position 496, P478D), FokI ELD, Sharkey, P478D (Q→E at position 486, I→L at position 499, N→D at position 496, S418P+K441E, P478D), FokI ELD, Q481D (Q→E at position 486, I→L at position 499, N→D at position 496, Q481D), FokI ELD, Sharkey, Q481D (Q→E at position 486, I→L at position 499, N→D at position 496, S418P+K441E, Q481D), FokI KKR (E→K at position 490, I→K at position 538, H→R at position 537), FokI KKR Sharkey, (E→K at position 490, I→K at position 538, H→R at position 537, S418P+K441E), FokI KKR, Q481E (E→K at position 490, I→K at position 538, H→R at position 537, Q481E), FokI KKR, Sharkey Q481E (E→K at position 490, I→K at position 538, H→R at position 537, S418P+K441E, Q481E), FokI KKR, R416E (E→K at position 490, I→K at position 538, H→R at position 537, R416E), FokI KKR, Sharkey, R416E (E→K at position 490, I→K at position 538, H→R at position 537, S418P+K441E, R416E), FokI KKR, K525S (E→K at position 490, I→K at position 538, H→R at position 537, K525S), FokI KKR, Sharkey, K525S (E→K at position 490, I→K at position 538, H→R at position 537, S418P+K441E, K525S), FokI KKR, R416Y (E→K at position 490, I→K position 538, H→R at position 537, R416Y), FokI KKR, Sharkey, R416Y (E→K at position 490, I→K at position 538, H→R at position 537, S418P+K441E, R416Y), FokI, KKR I479T (E→K at position 490, I→K at position 538, H→R at position 537, I1479T), FokI, KKR Sharkey I479T (E→K at position 490, I→K at position 538, H→R at position 537, S418P+K441E, 1479T, FokI, KKR P478D (E→K at position 490, I→K at positions 538, H→R at position 537, P478D), FokI, KKR Sharkey P478D (E→K at position 490, I→K at position 538, H→R at position 537, P478D), FokI DAD (R→D at position 487, N→D at position 496, I→A at position 499), FokI DAD Sharkey (R→D at position 487, N→D at position 496, I→A at position 499, S418P+K441E), FokI RVR (D→R at position 483, H→R at position 537, I→V at position 538), FokI RVR Sharkey (D→R at position 483, H→R at position 537, I→V at position 538, S418P+K441E).

The ZFNs described herein may also include any linker sequence, including but not limited to sequences disclosed herein (L0, N7a, N7c, etc.) and/or those disclosed in U.S. Pat. Nos. 7,888,121; 7,914,796; 8,034,598; 8,623,618; 9,567,609; and U.S. Publication No. 20170218349, which may be used between the N- or C-terminal of the DNA-binding domain and N- or C-terminal of the FokI cleavage domain.

ZFPs of the ZFNs as described herein (including engineered and/or wild-type cleavage domains) may also include modifications to increase the specificity of a ZFN, including a nuclease pair, for its intended target relative to other unintended cleavage sites, known as off-target sites (see U.S. Patent Publication No. 20180087072). Thus, nucleases described herein can comprise specific linkers between the DNA-binding domain and cleavage domain; and/or can comprise mutations in one or more of their DNA binding domain backbone regions and/or one or more mutations in their nuclease cleavage domains as described above. The ZFPs of these nucleases can include mutations to amino acids within the ZFP DNA binding domain ('ZFP backbone') that can interact non-specifically with phosphates on the DNA backbone, but they do not comprise changes in the DNA recognition helices. Thus, the invention includes ZFPs comprising mutations of cationic amino acid residues in the ZFP backbone that are not required for nucleotide target specificity. In some embodiments, these mutations in the ZFP backbone comprise mutating a cationic amino acid residue to a neutral or anionic amino acid residue. In some embodiments, these mutations in the ZFP backbone comprise mutating a polar amino acid residue to a neutral or non-polar amino acid residue. In preferred embodiments, mutations at made at position (−5), (−9) and/or position (−14) relative to the DNA binding helix. In some embodiments, a zinc finger may comprise one or more mutations at (−5), (−9) and/or (−14). In further embodiments, one or more zinc finger in a multi-finger zinc finger protein may comprise mutations in (−5), (−9) and/or (−14). In some embodiments, the amino acids at (−5), (−9) and/or (−14) (e.g., an arginine (R) or lysine (K)) are mutated to an alanine (A), leucine (L), Ser (S), Asp (N), Glu (E), Tyr (Y) and/or glutamine (Q).

In certain embodiments, the ZFNs comprise at least one of the following pairs: 68796 and 68813; 68796 and 68861; 68812 and 68813; 68876 and 68877; 68815 and 55266; 68879 and 55266; 68798 and 68815; or 68846 and 53853 as shown in Table 6. In other embodiments, the ZFNs comprise at least one of the following pairs: 57531 and 72732; 57531 and 72748; 68957 and 57071; 68957 and 72732; 68957 and 72748; 72678 and 57071; 72678 and 72732; or 72678 and 72748 as shown in Table 8.

Alternatively, nucleases may be assembled in vivo at the nucleic acid target site using so-called "split-enzyme" technology (see, e.g., U.S. Patent Publication No. 2009/0068164). Components of such split enzymes may be expressed either on separate expression constructs or can be linked in one open reading frame where the individual components are separated, for example, by a self-cleaving 2A peptide or IRES sequence. Components may be individual zinc finger binding domains or domains of a meganuclease nucleic acid binding domain.

Nucleases (e.g., ZFNs and/or TALENs) can be screened for activity prior to use, for example in a yeast-based chromosomal system as described in as described in U.S. Pat. No. 8,563,314.

In certain embodiments, the nuclease comprises a CRISPR/Cas system. The CRISPR (clustered regularly interspaced short palindromic repeats) locus, which encodes RNA components of the system, and the Cas (CRISPR-associated) locus, which encodes proteins (Jansen, et al. (2002) *Mol. Microbiol.* 43:1565-1575; Makarova, et al. (2002) *Nucleic Acids Res.* 30:482-496; Makarova, et al. (2006) *Biol. Direct* 1:7; Haft, et al. (2005) *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Exemplary CRISPR/Cas nuclease systems targeted to TCR genes and other genes are disclosed for example, in U.S. Patent Publication No. 2015/0056705. The nuclease(s) may make one or more double-stranded and/or single-stranded cuts in the target site. In certain embodiments, the nuclease comprises a catalytically inactive cleavage domain (e.g., FokI and/or Cas protein). See, e.g., U.S. Pat. Nos. 9,200,266 and 8,703,489 and Guillinger, et al. (2014) *Nature Biotech.* 32(6):577-582. The catalytically inactive cleavage domain may, in combination with a catalytically active domain act as a nickase to make a single-stranded cut. Therefore, two nickases can be used in combination to make a double-stranded cut in a specific region. Additional nickases are also known in the art, for example, McCaffrey, et al. (2016) *Nucleic Acids Res.* 44(2):e11. doi: 10.1093/nar/gkv878. Epub 2015 Oct. 19. In addition, dead Cas ('dCas') or a Cas nickase may be fused to a base modifying enzyme (e.g., cytidine deaminase) to create a base editing system (Komor, et al. (2016) *Nature* 533:420). These systems allow for the alteration of a DNA base (modification) by the base editor complex without creating a double strand break in the DNA. Thus, in some embodiments, guide RNAs (Table 2) may be used to introduce mutations in a TRAC gene to cause a knock out.

Delivery

The proteins (e.g., transcription factors, nucleases, TCR and CAR molecules), polynucleotides and/or compositions comprising the proteins and/or polynucleotides described herein may be delivered to a target cell by any suitable means, including, for example, by injection of the protein and/or mRNA components. In some embodiments, the proteins are introduced into the cell by cell squeezing (see Kollmannsperger, et al. (2016) *Nat Comm* 7, 10372 doi: 10.1038/ncomms10372).

Suitable cells include but not limited to eukaryotic and prokaryotic cells and/or cell lines. Non-limiting examples of such cells or cell lines generated from such cells include T-cells, COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as Spodopterafugiperda (Sf), or fungal cells such as *Saccharomyces, Pichia* and *Schizosaccharomyces*. In certain embodiments, the cell line is a CHO-K1, MDCK or HEK293 cell line. Suitable cells also include stem cells such as, by way of example, embryonic stem cells, induced pluripotent stem cells (iPS cells), hematopoietic stem cells, neuronal stem cells and mesenchymal stem cells.

Methods of delivering proteins comprising DNA-binding domains as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

DNA binding domains and fusion proteins comprising these DNA binding domains as described herein may also be delivered using vectors containing sequences encoding one or more of the DNA-binding protein(s). Additionally, additional nucleic acids (e.g., donors) also may be delivered via these vectors. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more DNA-binding protein-encoding sequences and/or additional nucleic acids as appropriate. Thus, when one or more DNA-binding proteins as described herein are introduced into the cell, and additional DNAs as appropriate, they may be carried on the same vector or on different vectors. When multiple vectors are used, each vector may comprise a sequence encoding one or multiple DNA-binding proteins and additional nucleic acids as desired.

Conventional viral and non-viral based gene transfer methods can be used to introduce nucleic acids encoding engineered DNA-binding proteins in cells (e.g., mammalian cells) and target tissues and to co-introduce additional nucleotide sequences as desired. Such methods can also be used to administer nucleic acids (e.g., encoding DNA-binding proteins and/or donors) to cells in vitro. In certain embodiments, nucleic acids are administered for in vivo or ex vivo gene therapy uses. Non-viral vector delivery systems include DNA plasmids, naked nucleic acid, and nucleic acid complexed with a delivery vehicle such as a liposome, lipid nanoparticle or poloxamer. Viral vector delivery systems include DNA and RNA viruses, which have either episomal or integrated genomes after delivery to the cell. For a review of gene therapy procedures, see Anderson (1992) *Science* 256:808-813; Nabel & Felgner (1993) *TIBTECH* 11:211-217; Mitani & Caskey (1993) *TIBTECH* 11:162-166; Dillon (1993) *TIBTECH* 11:167-175; Miller (1992) *Nature* 357:455-460; Van Brunt (1988) *Biotechnology* 6(10): 1149-1154; Vigne (1995) *Restorative Neurology andNeuroscience* 8:35-36; Kremer & Perricaudet (1995) *British Medical Bulletin* 51(1):31-44; Haddada, et al. (1995) *Current Topics in Microbiology and Immunology* Doerfler and Böhm (eds.); and Yu, et al. (1994) *Gene Therapy* 1:13-26.

Methods of non-viral delivery of nucleic acids include electroporation, lipofection, microinjection, biolistics, virosomes, liposomes, lipid nanoparticles, immunoliposomes, polycation or lipid:nucleic acid conjugates, naked DNA, mRNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™, Lipofectin™, and Lipofectamine™ RNAiMAX). Cationic and neutral lipids that are suitable for efficient receptor-recognition lipofection of polynucleotides include those of Felgner, International Patent Publication Nos. WO 91/17424 and WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal (1995) Science 270:404-410; Blaese, et al. (1995) Cancer Gene Ther. 2:291-297; Behr, et al. (1994) Bioconjugate Chem. 5:382-389; Remy, et al. (1994) Bioconjugate Chem. 5:647-654; Gao, et al. (1995) Gene Therapy 2:710-722; Ahmad, et al. (1992) Cancer Res. 52:4817-4820; U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid, et al. (2009) Nature Biotechnology 27(7):643).

The use of RNA or DNA viral based systems for the delivery of nucleic acids encoding engineered DNA-binding proteins, and/or donors (e.g., CARs or ACTRs) as desired takes advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher, et al. (1992) J. Virol. 66:2731-2739; Johann, et al. (1992) J. Virol. 66:1635-1640; Sommerfelt, et al. (1990) Virol. 176: 58-59; Wilson, et al. (1989) J. Virol. 63:2374-2378; Miller, et al. (1991) J. Virol. 65:2220-2224; International Patent Publication No. WO 1994/026877).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West, et al. (1987) Virology 160:38-47; U.S. Pat. No. 4,797,368; International Patent Publication No. WO 93/24641; Kotin (1994) Human Gene Therapy 5:793-801; Muzyczka (1994) J. Clin. Invest. 94:1351. Construction of recombinant AAV vectors are described in a number of publications, including U.S. Pat. No. 5,173,414; Tratschin, et al. (1985) Mol. Cell. Biol. 5:3251-3260; Tratschin, et al. (1984) Mol. Cell. Biol. 4:2072-2081; Hermonat & Muzyczka (1984) PNAS USA 81:6466-6470; and Samulski et al. (1989) J. Virol. 63:03822-3828.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar, et al. (1995) Blood 85:3048-305; Kohn, et al. (1995) Nat. Med. 1:1017-102; Malech, et al. (1997) PNAS USA 94:22 12133-12138). PA317/pLASN was the first therapeutic vector used in a gene therapy trial. (Blaese, et al. (1995) Science 270:475-480). Transduction efficiencies of 50% or greater have been observed for MFG-S packaged vectors. (Ellem, et al. (1997) Immunol Immunother. 44(1): 10-20; Dranoff, et al. (1997) Hum. Gene Ther. 1:111-2.

Recombinant adeno-associated virus vectors (rAAV) are a promising alternative gene delivery system based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner, et al. (1998) Lancet 351(9117): 1702-3, Kearns, et al. (1996) Gene Ther. 9:748-55). Other AAV serotypes, including AAV1, AAV3, AAV4, AAV5, AAV6, AAV8, AAV8.2, AAV9 and AAVrh10 and pseudotyped AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman, et al. (1998) Hum. Gene Ther. 7:1083-9). Additional examples of the use of adenovirus vectors for gene transfer in clinical trials include Rosenecker, et al. (1996) Infection 24(1):5-10; Sterman, et al. (1998) Hum. Gene Ther. 9(7):1083-1089; Welsh, et al. (1995) Hum. Gene Ther. 2:205-18; Alvarez, et al. (1997) Hum. Gene Ther. 5:597-613; Topf, et al. (1998) Gene Ther. 5:507-513; Sterman, et al. (1998) Hum. Gene Ther. 7:1083-1089.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. In addition, AAV can be manufactured using a baculovirus system (see, e.g., U.S. Pat. Nos. 6,723,551 and 7,271,002).

Purification of AAV particles from a 293 or baculovirus system typically involves growth of the cells which produce the virus, followed by collection of the viral particles from the cell supernatant or lysing the cells and collecting the virus from the crude lysate. AAV is then purified by methods known in the art including ion exchange chromatography (e.g., see U.S. Pat. Nos. 7,419,817 and 6,989,264), ion exchange chromatography and CsCl density centrifugation (e.g., International Patent Publication No. WO 2011/094198 A10), immunoaffinity chromatography (e.g., International Patent Publication No. WO 2016/128408) or purification using AVB Sepharose (e.g., GE Healthcare Life Sciences).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han, et al. (1995) Proc. Natl. Acad. Sci. USA 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by re-implantation of the cells into a patient, usually after selection for cells which have incorporated the vector.

The cells described herein may also be used for cell therapies, for example adoptive cell therapy for treatment and/or prevention of a cancer. Cell therapy is a specialized type of transplant wherein cells of a certain type (e.g., T cells reactive to a tumor antigen or B cells) are given to a recipient. Cell therapy can be done with cells that are either autologous (derived from the recipient) or allogenic (derived from a donor) and the cells may be immature cells such as stem cells, or completely mature and functional cells such as T cells. In fact, in some diseases such certain cancers, T cells may be manipulated ex vivo to increase their avidity for certain tumor antigens, expanded and then introduced into the patient suffering from that cancer type in an attempt to eradicate the tumor. This is particularly useful when the endogenous T cell response is suppressed by the tumor itself.

Ex vivo cell transfection for diagnostics, research, transplant or for gene and/or cell therapy (e.g., via re-infusion of the transfected cells into the host organism) is well known to those of skill in the art. In a preferred embodiment, cells are isolated from the subject organism, transfected with a DNA-binding proteins nucleic acid (gene or cDNA), and re-infused back into the subject organism (e.g., patient). Various cell types suitable for ex vivo transfection are well known to those of skill in the art (see, e.g., Freshney, et al., Culture of Animal Cells, A Manual of Basic Technique (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba, et al. (1992) J. Exp. Med. 176:1693-1702).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+(panB cells), GR-1 (granulocytes), and Iad (differentiated antigen presenting cells) (see Inaba, et al. (1992) J. Exp. Med. 176:1693-1702).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific ZFNs (see, U.S. Pat. No. 8,597,912) in the stem cells, or those that are disrupted in a caspase, again using caspase-6 specific ZFNs for example. These cells can be transfected with the ZFP TFs that are known to regulate TCR.

Vectors (e.g., retroviruses, adenoviruses, liposomes, etc.) containing therapeutic DNA-binding proteins (or nucleic acids encoding these proteins) can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory, et al. (1996) *Proc. Natl. Acad. Sci. USA* 93:11382-11388; Dull, et al. (1998) *J. Virol.* 72:8463-8471; Zuffery, et al. (1998) *J. Virol.* 72:9873-9880; Follenzi, et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells, including T-cells and stem cells of any type. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as Spodopterafugiperda (Sf), and fungal cells such as *Saccharomyces*, *Pichia* and *Schizosaccharomyces*. Progeny, variants and derivatives of these cell lines can also be used.

Applications

The disclosed compositions and methods can be used for any application in which it is desired to modulate TCR and/or B2M expression and/or functionality, including but not limited to, therapeutic and research applications in which TCR and/or B2M modulation is desirable. For example, the disclosed compositions can be used in vivo and/or ex vivo (cell therapies) to disrupt the expression of endogenous TCRs and/or B2M in T cells modified for adoptive cell therapy to express one or more exogenous CARs, exogenous TCRs, or other cancer-specific receptor molecules, thereby treating and/or preventing the cancer. T cells may be effector T cells or regulatory T cells. In addition, in such settings, abrogation of TCR expression within a cell can eliminate or substantially reduce the risk of an unwanted cross reaction with healthy, nontargeted tissue (i.e. a graft-vs-host response). Modified cells as described herein can also be used for treatment of cancers, including, but not limited to, prostate, chronic lymphocytic leukemia (CLL) and Non-Hodgkin's lymphomas.

Methods and compositions also include stem cell compositions (e.g., iPSC and HSC/HSPC) wherein the B2M, TCRA and/or TCRB genes within the stem cells has been modulated (modified) and the cells further comprise an ACTR and/or a CAR and/or an isolated or engineered TCR. For example, TCR knock out or knock down modulated allogeneic hematopoietic stem cells can be introduced into an HLA-matched patient following bone marrow ablation. These altered HSC would allow the re-colonization of the patient but would not cause potential GvHD. The introduced cells may also have other alterations to help during subsequent therapy (e.g., chemotherapy resistance) to treat the underlying disease. The HLA class I null cells also have use as an "off the shelf" therapy in emergency room situations with trauma patients.

The methods and compositions of the invention are also useful for the design and implementation of in vitro and in vivo models, for example, animal models of TCR or B2M and associated disorders, which allows for the study of these disorders.

All patents, patent applications and publications mentioned herein are hereby incorporated by reference in their entireties.

Although disclosure has been provided in some detail by way of illustration and example for the purposes of clarity and understanding, it will be apparent to those of skill in the art that various changes and modifications can be practiced without departing from the spirit or scope of the disclosure. Accordingly, the foregoing disclosure and following examples should not be construed as limiting.

EXAMPLES

Example 1: Design of TCR-Specific Nucleases

TCR-specific ZFNs were constructed to enable site specific introduction of double strand breaks at the TCRa (TCRA) gene. ZFNs were designed essentially as described in Urnov, et al. (2005) Nature 435(7042):646-651, Lombardo, et al. (2007) Nat Biotechnol. 25(11):1298-306, and U.S. Patent Publication Nos. 2008/0131962; 2015/0164954; 2014/0120622; and 2014/0301990 and U.S. Pat. No. 8,956, 828. The ZFN pairs targeted different sites in the constant region of the TCRA gene (see FIG. 1). The recognition helices for exemplary ZFN pairs as well as the target sequence are shown below in Table 1. Target sites of the TCRA zinc-finger designs are shown in the first column. Nucleotides in the target site that are targeted by the ZFP recognition helices are indicated in uppercase letters; non-targeted nucleotides indicated in lowercase. Linkers used to join the Fokl nuclease domain and the ZFP DNA binding domain are also shown (see U.S. Patent Publication No. 2015/0132269). For example, the amino acid sequence of the domain linker L0 is DNA binding domain-QLVKS-Fokl nuclease domain (SEQ ID NO:5). Similarly, the amino acid sequences for the domain linker N7a is Fokl nuclease domain-SGTPHEVGVYTL-DNA binding domain (SEQ ID NO:6), and N7c is Fokl nuclease domain-SGAIRCH-DEFWF-DNA binding domain (SEQ ID NO:7).

TABLE 1

TCR-α (TCRA) Zinc-finger Designs

| ZFN Name target sequence | F1 | F2 | F3 | F4 | F5 | F6 | Domain linker |
|---|---|---|---|---|---|---|---|
| SBS55204 5'ttGCTC TTGAAGTC cATAGACc tcatgt (SEQ ID NO: 8) | DRSNLSR (SEQ ID NO: 22) | QKVTLAA (SEQ ID NO: 23) | DRSALSR (SEQ ID NO: 24) | TSGNLTR (SEQ ID NO: 25) | YRSSLKE (SEQ ID NO: 26) | TSGNLTR (SEQ ID NO: 25) | L0 |
| SBS53759 5'gtGCTG TGgCCTGG AGCAACAa atctga (SEQ ID NO: 9) | QQNVLIN (SEQ ID NO: 27) | QNATRTK (SEQ ID NO: 28) | QSGHLAR (SEQ ID NO: 29) | NRYDLMT (SEQ ID NO: 30) | RSDSLLR (SEQ ID NO: 31) | QSSDLTR (SEQ ID NO: 32) | L0 |
| SBS55229 5'ctGTTG CTCTTGAA GTCcatag acctca (SEQ ID NO: 10) | DRSALAR (SEQ ID NO: 33) | QSGNLAR (SEQ ID NO: 34) | HRSTLQG (SEQ ID NO: 35) | QSGDLTR (SEQ ID NO: 36) | TSGSLTR (SEQ ID NO: 37) | NA | L0 |
| SBS53785 5'ctGTGG CCtGGAGC AACAaatc tgactt (SEQ ID NO: 11) | QHQVLVR (SEQ ID NO: 38) | QNATRTK (SEQ ID NO: 28) | QSGHLSR (SEQ ID NO: 39) | DRSDLSR (SEQ ID NO: 40) | RSDALAR (SEQ ID NO: 41) | NA | L0 |
| SBS53810 5'agGATT CGGAACCC AATCACtg (SEQ ID NO: 12) | DQSNLRA (SEQ ID NO: 42) | TSSNRKT (SEQ ID NO: 43) | DSSTRKT (SEQ ID NO: 44) | QSGNLAR (SEQ ID NO: 34) | RSDDLSE (SEQ ID NO: 45) | TNSNRKR (SEQ ID NO: 46) | L0 |
| SBS55255 5'ctCCTG AAAGTGGC CGGgttta atctgc (SEQ ID NO: 13) | RSDHLST (SEQ ID NO: 47) | DRSHLAR (SEQ ID NO: 48) | LKQHLNE (SEQ ID NO: 49) | TSGNLTR (SEQ ID NO: 25) | HRTSLTD (SEQ ID NO: 50) | NA | L0 |
| SBS55248 5'agGATT CGGAACCC AATCACtg acaggt (SEQ ID NO: 14) | DQSNLRA (SEQ ID NO: 42) | TSSNRKT (SEQ ID NO: 43) | LQQTLAD (SEQ ID NO: 51) | QSGNLAR (SEQ ID NO: 34) | RREDLIT (SEQ ID NO: 52) | TSSNLSR (SEQ ID NO: 53) | L0 |
| SBS55254 5'ctCCTG AAAGTGGC CGGgttta atctgc (SEQ ID NO: 13) | RSDHLST (SEQ ID NO: 47) | DRSHLAR (SEQ ID NO: 48) | LKQHLNE (SEQ ID NO: 49) | QSGNLAR (SEQ ID NO: 34) | HNSSLKD (SEQ ID NO: 54) | NA | L0 |
| SBS55260 5'ctCCTG AAAGTGGC CGGgttta atctgc (SEQ ID NO: 13) | RSDHLST (SEQ ID NO: 47) | DRSHLAR (SEQ ID NO: 48) | LNHHLQQ (SEQ ID NO: 55) | QSGNLAR (SEQ ID NO: 34) | HKTSLKD (SEQ ID NO: 56) | NA | L0 |

TABLE 1-continued

TCR-α (TCRA) Zinc-finger Designs

| ZFN Name target sequence | F1 | F2 | F3 | F4 | F5 | F6 | Domain linker |
|---|---|---|---|---|---|---|---|
| SBS55266 5'tcAAGC TGGTCGAG aAAAGCTt tgaaac (SEQ ID NO: 15) | QSSDLSR (SEQ ID NO: 57) | QSGNRTT (SEQ ID NO: 58) | RSANLAR (SEQ ID NO: 59) | DRSALAR (SEQ ID NO: 33) | RSDVLSE (SEQ ID NO: 60) | KHSTRRV (SEQ ID NO: 61) | N7c |
| SBS53853 5'aaCAGG TAaGACAG GGGTCTAg cctggg (SEQ ID NO: 16) | TMHQRVE (SEQ ID NO: 62) | TSGHLSR (SEQ ID NO: 63) | RSDHLTQ (SEQ ID NO: 64) | DSANLSR (SEQ ID NO: 65) | QSGSLTR (SEQ ID NO: 66) | AKWNLDA (SEQ ID NO: 67) | L0 |
| SBS53860 5'ctGTGC TAGACATG aGGTCTAt ggactt (SEQ ID NO: 17) | TMHQRVE (SEQ ID NO: 62) | TSGHLSR (SEQ ID NO: 63) | RNDSLKT (SEQ ID NO: 68) | DSSNLSR (SEQ ID NO: 69) | QKATRTT (SEQ ID NO: 70) | RNASRTR (SEQ ID NO: 72) | N7a |
| SBS53863 5'ttCAAG AGCAACAG tGCTGTGg cctgga (SEQ ID NO: 18) | RSDSLLR (SEQ ID NO: 31) | QSSDLRR (SEQ ID NO: 73) | RSDNLSE (SEQ ID NO: 74) | ERANRNS (SEQ ID NO: 75) | RSDNLAR (SEQ ID NO: 76) | QKVNLMS (SEQ ID NO: 77) | L0 |
| SBS55287 5'ttCAAG AGCAACAG tGCTGTGg cctgga (SEQ ID NO: 18) | RSDSLLR (SEQ ID NO: 31) | QSSDLRR (SEQ ID NO: 73) | RSDNLSE (SEQ ID NO: 74) | ERANRNS (SEQ ID NO: 75) | RSDNLAR (SEQ ID NO: 76) | QKVNLRE (SEQ ID NO: 78) | L0 |
| SBS53855 5'ctGTGC TAGACATG aGGTCTAt ggactt (SEQ ID NO: 17) | TMHQRVE (SEQ ID NO: 62) | TSGHLSR (SEQ ID NO: 63) | RSDTLSQ (SEQ ID NO: 79) | DRSDLSR (SEQ ID NO: 40) | QKATRTT (SEQ ID NO: 70) | RNASRTR (SEQ ID NO: 72) | N7a |
| SES53885 5'ccTGTC AGtGATTG GGTTCCGa atcctc (SEQ ID NO: 19) | RSDTLSE (SEQ ID NO: 186) | TSGSLTR (SEQ ID NO: 37) | RSDHLST (SEQ ID NO: 47) | TSSNRTK (SEQ ID NO: 71) | RSDNLSE (SEQ ID NO: 74) | WHSSLRV (SEQ ID NO: 83) | N7a |
| SBS52774 5'ccTGTC AGtGATTG GGTTCCGa atcctc (SEQ ID NO: 19) | RKQTRTT (SEQ ID NO: 80) | HRSSLRR (SEQ ID NO: 81) | RSDHLST (SEQ ID NO: 47) | TSANLSR (SEQ ID NO: 82) | RSDNLSE (SEQ ID NO: 74) | WHSSLRV (SEQ ID NO: 83) | N7a |
| SBS53909 5'tcCTCC TGAAAGTG GCCGGGtt taatct (SEQ ID NO: 20) | RSAHLSR (SEQ ID NO: 84) | DRSDLSR (SEQ ID NO: 40) | RSDVLSV (SEQ ID NO: 85) | QNNHRIT (SEQ ID NO: 86) | RSDVLSE (SEQ ID NO: 60) | SPSSRRT (SEQ ID NO: 87) | L0 |

TABLE 1-continued

TCR-α (TCRA) Zinc-finger Designs

| ZFN Name target sequence | F1 | F2 | F3 | F4 | F5 | F6 | Domain linker |
|---|---|---|---|---|---|---|---|
| SBS52742 5'tcCTCC TGAAAGTG GCCGGGtt taatct (SEQ ID NO: 20) | RSAHLSR (SEQ ID NO: 84) | DRSDLSR (SEQ ID NO: 40) | RSDSLSV (SEQ ID NO: 88) | QNANRKT (SEQ ID NO: 89) | RSDVLSE (SEQ ID NO: 60) | SPSSRRT (SEQ ID NO: 87) | L0 |
| SBS53856 5'ctGTGC TAGACATG aGGTCTAtg (SEQ ID NO: 21) | TMHQRVE (SEQ ID NO: 62) | TSGHLSR (SEQ ID NO: 63) | RSDSLST (SEQ ID NO: 90) | DRANRIK (SEQ ID NO: 91) | QKATRTT (SEQ ID NO: 70) | RNASRTR (SEQ ID NO: 72) | N7a |

All ZFNs were tested and found to bind to their target sites and found to be active as nucleases.

The ZFPs as described herein may also include one or more mutations to phosphate contact residues of the zinc finger protein and/or the FokI domain, for example, the nR-5Qabc mutant (to ZFP backbone) and/or R416S and/or K525S mutants (to FokI), described in U.S. Patent Publication No. 20180087072.

Guide RNAs for the *S. pyogenes* CRISPR/Cas9 system were also constructed to target the TCRA gene. See, also, U.S. Patent Publication No. 2015/0056705 for additional TCR alpha-targeted guide RNAs. The target sequences in the TCRA gene are indicated as well as the guide RNA sequences in Table 2 below. All guide RNAs are tested in the CRISPR/Cas9 system and are found to be active.

TABLE 2

Guide RNAs for the constant region of human TCRA (TRAC)

| Name | Strand | Target (5'->3') | gRNA (5' -> 3') |
|---|---|---|---|
| TRAC-Gr14 | R | GCTGGTACACGGCAGGGTCAGGG (SEQ ID NO: 92) | GCTGGTACACGGCAGGGTCA (SEQ ID NO: 104) |
| TRAC-Gr25 | R | AGAGTCTCTCAGCTGGTACACGG (SEQ ID NO: 93) | gAGAGTCTCTCAGCTGGTACA (SEQ ID NO: 105) |
| TRAC-Gr71 | R | GAGAATCAAAATCGGTGAATAGG (SEQ ID NO: 94) | GAGAATCAAAATCGGTGAAT (SEQ ID NO: 106) |
| TRAC-Gf155 | F | ACAAAACTGTGCTAGACATGAGG (SEQ ID NO: 95) | gACAAAACTGTGCTAGACATG (SEQ ID NO: 107) |
| TRAC-Gf191 | F | AGAGCAACAGTGCTGTGGCCTGG (SEQ ID NO: 96) | gAGAGCAACAGTGCTGTGGCC (SEQ ID NO: 108) |
| TRAC-Gf271 | F | GACACCTTCTTCCCCAGCCCAGG (SEQ ID NO: 97) | GACACCTTCTTCCCCAGCCC (SEQ ID NO: 109) |
| TRAC-Gr2146 | R | CTCGACCAGCTTGACATCACAGG (SEQ ID NO: 98) | gCTCGACCAGCTTGACATCAC (SEQ ID NO: 110) |
| TRAC-Gf2157 | F | AAGTTCCTGTGATGTCAAGCTGG (SEQ ID NO: 99) | gAAGTTCCTGTGATGTCAAGC (SEQ ID NO: 111) |
| TRAC-Gf2179 | F | GTCGAGAAAGCTTTGAAACAGG (SEQ ID NO: 100) | GTCGAGAAAGCTTTGAAAC (SEQ ID NO: 112) |
| TRAC-Gr3081 | R | TTCGGAACCCAATCACTGACAGG (SEQ ID NO: 101) | gTTCGGAACCCAATCACTGAC (SEQ ID NO: 113) |
| TRAC-Gr3099 | R | CCACTTTCAGGAGGAGGATTCGG (SEQ ID NO: 102) | gCCACTTTCAGGAGGAGGATT (SEQ ID NO: 114) |
| TRAC-Gr3105 | R | ACCCGGCCACTTTCAGGAGGAGG (SEQ ID NO: 103) | gACCCGGCCACTTTCAGGAGG (SEQ ID NO: 115) |

Thus, the nucleases described herein (e.g., nucleases comprising a ZFP or a sgRNA DNA-binding domain) bind to their target sites and cleave the TCRA gene, thereby making genetic modifications within a TCRA gene comprising any of SEQ ID NO:6-48 or 137-205, including modifications (insertions and/or deletions) within any of these sequences (e.g., the target sequences shown in any of SEQ ID NO:8-21 and/or 92-103; 12-25 nucleotides of these target sites; and/or between paired target sites) and/or modifications within the following sequences: AACAGT, AGTGCT, CTCCT, TTGAAA, TGGACTT and/or AATCCTC (see, FIG. 1B). TALE nucleases targeted to these target sites are also designed and found to be functional in terms of binding and activity.

Furthermore, the DNA-binding domains (ZFPs and sgRNAs) all bound to their target sites and ZFP, TALE and sRNA DNA-binding domains that recognize these target sites are also formulated into active engineered transcription factors when associated with one or more transcriptional regulatory domains.

Example 2: Nuclease Activity In Vitro

The ZFNs described in Table 1 were used to test nuclease activity in K562 cells. To test cleavage activity, plasmids encoding the pairs of human TCRA-specific ZFNs described above were transfected into K562 cells with plasmid or mRNAs. K562 cells were obtained from the American Type Culture Collection and grown as recommended in RPMI medium (Invitrogen) supplemented with 10% qualified fetal bovine serum (FBS, Cyclone). For transfection, ORFs for the active nucleases listed in Table 1 were cloned into an expression vector optimized for mRNA production bearing a 5' and 3' UTRs and a synthetic polyA signal. The mRNAs were generated using the mMessage mMachine T7 Ultra kit (Ambion) following the manufacturer's instructions. In vitro synthesis of nuclease mRNAs used either a pVAX-based vector containing a T7 promoter, the nuclease proper and a polyA motif for enzymatic addition of a polyA tail following the in vitro transcription reaction, or a pGEM based vector containing a T7 promoter, a 5'UTR, the nuclease proper, a 3'UTR and a 64 bp polyA stretch (SEQ ID NO:188), or a PCR amplicon containing a T7 promoter, a 5'UTR, the nuclease proper, a 3'UTR and a 60 bp polyA stretch (SEQ ID NO:189). One million K562 cells were mixed with 250 ng or 500 ng of the ZFN encoding mRNA. Cells were transfected in an Amaxa Nucleofector II™ using program T-16 and recovered into 1.4 mL warm RPMI medium+10% FBS. Nuclease activity was assessed by deep sequencing (MiSeq, Illumina) as per standard protocols three days following transfection. The results are presented below in Table 3.

TABLE 3

Zinc Finger Nuclease activity

| Pair # | ZFN pair | NHEJ % (250 ng/ZFN) | SD | NHEJ % (500 ng/ZFN) | SD | Site |
|---|---|---|---|---|---|---|
| 1 | 55204:53759 | 76.7 | 1.3 | 87.7 | 1 | A2 |
| 2 | 55229:53785 | 91.4 | 1.5 | 93.6 | 1.7 | B |
| 3 | 53810:55255 | 81.6 | 0.6 | 91.5 | 1.3 | D1 |
| 4 | 55248:55254 | 95.4 | 1.8 | 96.2 | 1.2 | D2 |
| 5 | 55248:55260 | 87.9 | 1.3 | 93.0 | 1 | D3 |
| 6 | 55266:53853 | 85.3 | 1.4 | 88.9 | 0.4 | E |
| 7 | 53860:53863 | 77.1 | 1.7 | 87.3 | 1.1 | F1 |
| 8 | 53856:55287 | 53.6 | 3.2 | 74.8 | 1.3 | F2 |
| 9 | 53885:53909 | 90.1 | 1.6 | 90.2 | 1.5 | G1 |
| 10 | 52774:52742 | 76.8 | 0.8 | 84.4 | 2.2 | G0 |
| 11 | GFP | 0 | | 0 | | |

Highly active TCRA specific TALENs have also been previously described (see International Patent Publication No. WO 2014/153470).

The human TCRA-specific CRISPR/Cas9 systems were also tested. The activity of the CRISPR/Cas9 systems in human K562 cells was measured by MiSeq analysis. Cleavage of the endogenous TCRA DNA sequence by Cas9 is assayed by high-throughput sequencing (Miseq, Illumina).

In these experiments, Cas9 was supplied on a pVAX plasmid, and the sgRNA is supplied on a plasmid under the control of a promoter (e.g., the U6 promoter or a CMV promoter). The plasmids were mixed at either 100 ng of each or 400 ng of each and were mixed with 2e5 cells per run. The cells were transfected using the Amaxa system. Briefly, an Amaxa transfection kit is used and the nucleic acids are transfected using a standard Amaxa shuttle protocol. Following transfection, the cells are let to rest for 10 minutes at room temperature and then resuspended in prewarmed RPMI. The cells are then grown in standard conditions at 37° C. Genomic DNA was isolated 7 days after transfection and subject to MiSeq analysis.

Briefly, the guide RNAs listed in Table 2 were tested for activity. The guide RNAs were tested in three different configurations: G0 is the set up described above. G1 used a pVAX vector comprising a CMV promoter driving expression of the Cas9 gene and a U6-Guide RNA-tracer expression cassette where transcription of both reading frames is in the same orientation. G2 is similar to G1 except that the Cas9 and U6-Guide expression cassettes are in opposite orientations. These three set ups were tested using either 100 ng or 400 ng of transfected DNA, and the results are presented below in Table 4. Results are expressed as the 'percent indels' or "NHEJ %', where 'indels' means small insertions and/or deletions found as a result of the error prone NHEJ repair process at the site of a nuclease-induced double strand cleavage.

TABLE 4

CRISPR/Cas activity

| | % total_indels | | | | | |
|---|---|---|---|---|---|---|
| | GR0 | | GR1 | | GR2 | |
| Guide used | NHEJ % (100 ng) | NHEJ % (400 ng) | NHEJ % (100 ng) | NHEJ % (400 ng) | NHEJ % (100 ng) | NHEJ % (400 ng) |
| TCRA-Gr14 | 6.4 | 25.8 | 0.6 | 12.4 | 0.5 | 10.2 |
| TCRA-Gr25 | 14.6 | 26.9 | 2.4 | 21.7 | 1.1 | 21.6 |
| TCRA-Gr71 | 3.7 | 13.8 | 0.3 | 4.2 | 0.3 | 7.8 |
| TCRA-Gf155 | 6.0 | 19.5 | 1.2 | 12.7 | 0.8 | 15.9 |
| TCRA-Gf191 | 1.0 | 6.9 | 0.3 | 2.3 | 0.4 | 4.5 |
| TCRA-Gf271 | 4.7 | 21.5 | 0.8 | 10.3 | 0.7 | 15.2 |

TABLE 4-continued

| | CRISPR/Cas activity | | | | | |
|---|---|---|---|---|---|---|
| | % total_indels | | | | | |
| | GR0 | | GR1 | | GR2 | |
| Guide used | NHEJ % (100 ng) | NHEJ % (400 ng) | NHEJ % (100 ng) | NHEJ % (400 ng) | NHEJ % (100 ng) | NHEJ % (400 ng) |
| TCRA-Gr2146 | 1.1 | 8.8 | 0.3 | 1.7 | 0.2 | 2.0 |
| TCRA-Gf2157 | 3.8 | 22.2 | 0.6 | 9.6 | 0.6 | 12.0 |
| TCRA-Gf2179 | 0.8 | 4.9 | 0.2 | 1.8 | 0.2 | 1.4 |
| TCRA-Gr3081 | 5.9 | 23.6 | 0.7 | 11.5 | 0.8 | 12.6 |
| TCRA-Gr3099 | 2.1 | 21.1 | 0.4 | 7.1 | 0.3 | 6.2 |
| TCRA-Gr3105 | 12.1 | 45.9 | 2.2 | 22.0 | 1.0 | 7.6 |
| ZFN controls | | | | | | |
| 55248:55254 | 24.2 | 52.4 | | | | |
| 55229:53785 | 6.0 | 24.5 | | | | |
| 55266:53853 | 12.0 | 37.0 | | | | |

As shown, the nucleases described herein induce cleavage and genomic modifications at the targeted site.

Thus, the nucleases described herein (e.g., nucleases comprising a ZFP, a TALE or a sgRNA DNA-binding domain) bind to their target sites and cleave the TCRA gene, thereby making genetic modifications within a TCRA gene comprising any of SEQ ID NO:8-21 or 92-103, including modifications (insertions and/or deletions) within any of these sequences (SEQ ID NO:8-21, 92-103); modifications within 1-50 (e.g., 1 to 10) base pairs of these gene sequences; modifications between target sites of paired target sites (for dimers); and/or modifications within one or more of the following sequences: AACAGT, AGTGCT, CTCCT, TTGAAA, TGGACTT and/or AATCCTC (see, FIG. 1B).

Furthermore, the DNA-binding domains (ZFPs, TALEs and sgRNAs) all bound to their target sites and are also formulated into active engineered transcription factors when associated with one or more transcriptional regulatory domains.

Example 3: TCRA-Specific ZFN Activity in T Cells

The TCRA-specific ZFN pairs were also tested in human T cells for nuclease activity. mRNAs encoding the ZFNs were transfected into purified T cells. Briefly, T cells were obtained from leukopheresis product and purified using the Miltenyi CliniMACS system (CD4 and CD8 dual selection). These cells were then activated using Dynabeads (ThermoFisher) according to manufacturer's protocol. 3 days post activation, the cells were transfected with three doses of mRNA (60, 120 and 250 µg/mL) using a Maxcyte electroporator (Maxcyte), OC-100, 30e6 cells/mL, volume of 0.1 mL. Cells were analyzed for on target TCRA modification using deep sequencing (Miseq, Illumina) at 10 days after transfection. Cell viability and cell growth (total cell doublings) were measured throughout the 13-14 days of culture. In addition, TCR on the cell surface of the treated cells was measured using standard FACS analysis at day 10 of culture staining for CD3.

Figure 2B:
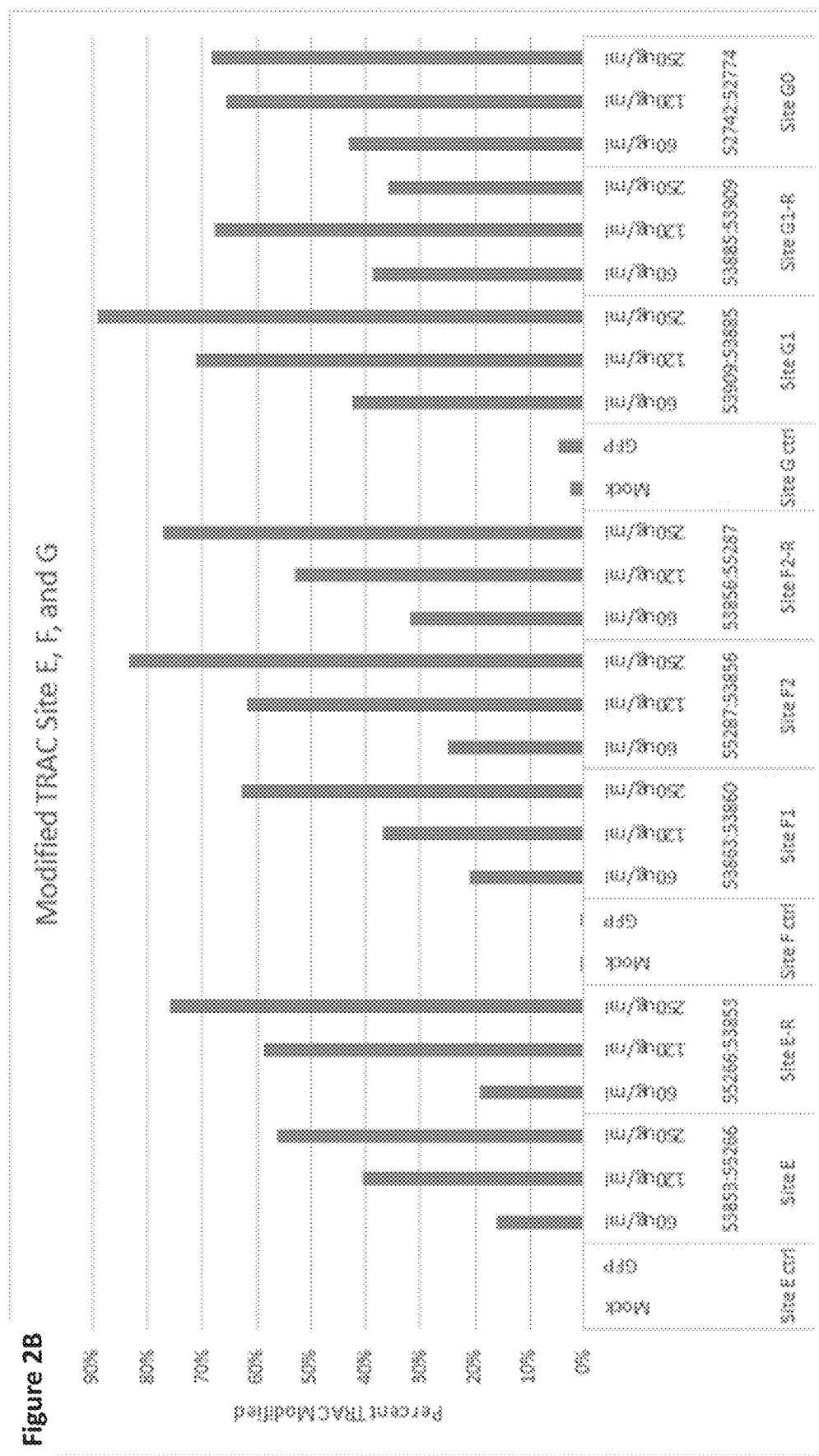
Figure 4:
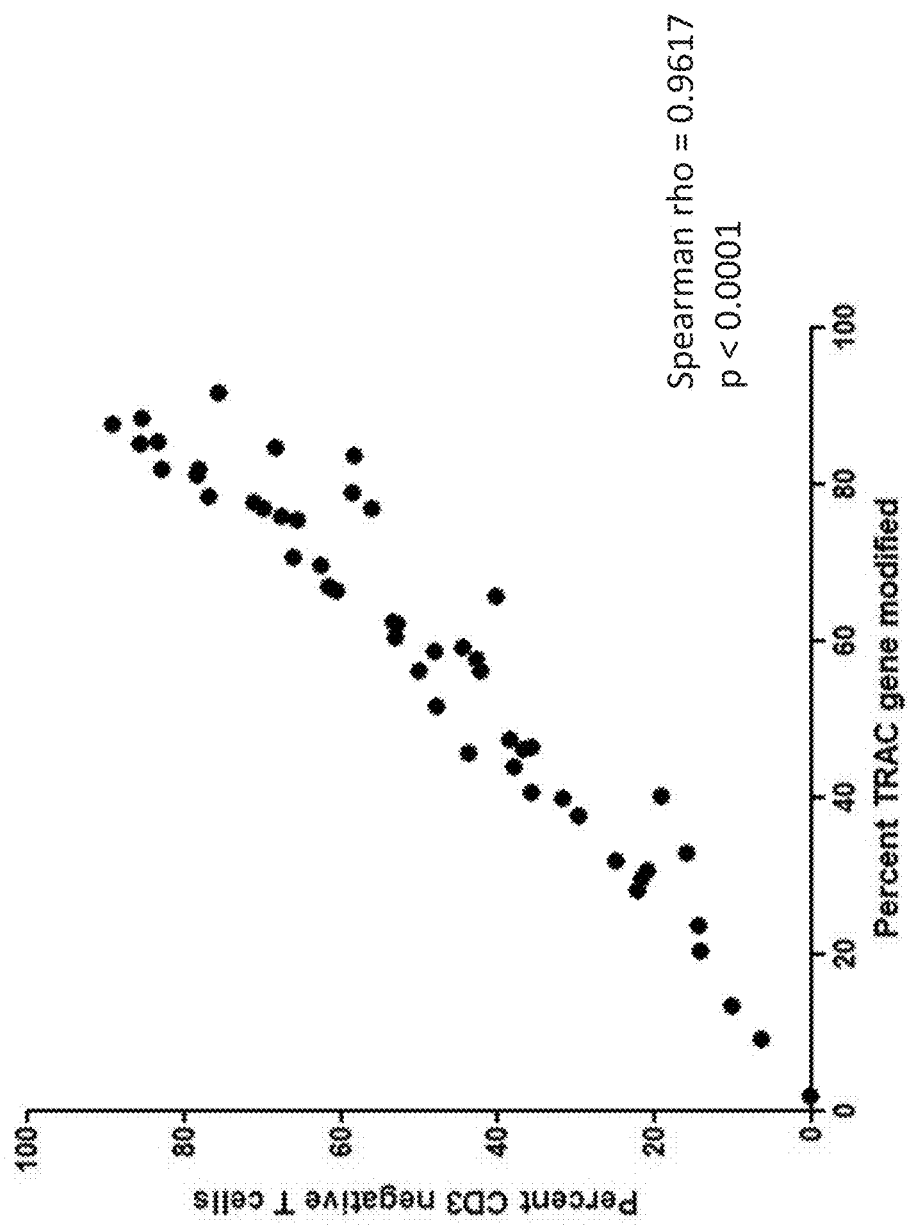
FIG. 4 is a graph showing the high degree of correlation in T cells between levels of TCRA sequence modification as measured via high throughput sequencing and loss of CD3 expression as measured by fluorescence activated cell sorting.

The TCRA-specific ZFN pairs were all active in T cells and some were capable of causing more than 80% TCRA allele modification in these conditions (see FIGS. 2A and 2B). Similarly, T cells treated with the ZFNs lost expression of CD3, where FACS analysis showed that in some cases between 80 and 90% of the T cells were CD3 negative (FIG. 3). A comparison between percent TCRA modified by ZFN and CD3 loss in these cells demonstrated a high degree of correlation (FIG. 4). Cell viability was comparable to the mock treatment controls, and TCRA knockout cell growth was also comparable to the controls (see FIG. 5A-5D).

Example 4: Double Knockout of B2M and TCRA with Targeted Integration

Nucleases as described above and B2M targeted nuclease described in Table 5 (see, also U.S. Patent Publication No. 2017/0173080) were used to inactivate B2M and TCRA and to introduce, via targeted integration, a donor (transgene) into either the TCRA or B2M locus. The B2M specific ZFNs are shown below in Table 5:

TABLE 5

| B2M-specific ZFN designs | | | | | | | |
|---|---|---|---|---|---|---|---|
| ZFN Name target sequence | F1 | F2 | F3 | F4 | F5 | F6 | Domain linker |
| SBS57327 5' taGCAATTC AGGAAaTTT GACtttccat (SEQ ID NO: 123) | DRSNLSR (SEQ ID NO: 22) | ARWYLDK (SEQ ID NO: 125) | QSGNLAR (SEQ ID NO: 34) | AKWNLDA (SEQ ID NO: 67) | QQHVLQN (SEQ ID NO: 119) | QNATRTK (SEQ ID NO: 28) | L0 |

TABLE 5-continued

B2M-specific ZFN designs

| ZFN Name target sequence | F1 | F2 | F3 | F4 | F5 | F6 | Domain linker |
|---|---|---|---|---|---|---|---|
| SBS57332 5'tgTCGGA TgGATGAAA CCCAGacac ata (SEQ ID NO: 117) | RSDNLSE (SEQ ID NO: 74) | ASKTRTN (SEQ ID NO: 120) | QSGNLAR (SEQ ID NO: 34) | TSANLSR (SEQ ID NO: 82) | TSGNLTR (SEQ ID NO: 25) | RTEDRLA (SEQ ID NO: 121) | N6a |
| SBS57531 5' gaGTAGCGc GAGCACAGC taaggccac g (SEQ ID NO: 126) | AQCCLFH (SEQ ID NO: 128) | DQSNLRA (SEQ ID NO: 42) | RSANLTR (SEQ ID NO: 129) | RSDDLTR (SEQ ID NO: 130) | QSGSLTR (SEQ ID NO: 66) | N/A | N6a |
| SBS57071 gcCACGGAg CGAGACATC TCGgcccgaa (SEQ ID NO: 127) | RSDDLSK (SEQ ID NO: 131) | DSSARKK (SEQ ID NO: 132) | DRSNLSR (SEQ ID NO: 22) | QRTHLRD (SEQ ID NO: 133) | QSGHLAR (SEQ ID NO: 29) | DSSNREA (SEQ ID NO: 134) | L0 |

In this experiment, the TCRA-specific ZFN pair was SBS #55266/SBS #53853, comprising the sequence TTGAAA between the TCRA-specific ZFN target sites (Table 1), and the B2M pair was SBS #57332/SBS #57327 (Table 5), comprising the sequence TCAAAT between the B2M-specific ZFN target sites.

Briefly, T-Cells (AC-TC-006) were thawed and activated with CD3/28 dynabeads (1:3 cells:bead ratio) in X-vivo15 T-cell culture media (day 0). After two days in culture (day 2), an AAV donor (comprising a GFP transgene and homology arms to the TCRA or B2M gene) was added to the cell culture, except control groups without donor were also maintained. The following day (day 3), TCRA and B2M ZFNs were added via mRNA delivery in the following 5 Groups:
(a) Group 1 (TCRA and B2M ZFNs only, no donor): TCRA 120 ug/mL: B2M only 60 ug/mL;
(b) Group 2 (TCRA and B2M ZFNs and donor with TCRA homology arms): TCRA 120 ug/mL; B2M 60 ug/mL and AAV (TCRA-Site E-hPGK-eGFP-Clone E2) 1E5vg/cell;
(c) Group 3 (TCRA and B2M ZFNs and donor with TCRA homology arms): TCRA 120 ug/mL; B2M 60 ug/mL; and AAV (TCRA-Site E-hPGK-eGFP-Clone E2) 3E4vg/cell;
(d) Group 4 (TCRA and B2M ZFNs and donor with B2M homology arms): TCRA 120 ug/mL; B2M 60 ug/mL and AAV (pAAV B2M-hPGK GFP) 1E5vg/cell
(e) Group 5 (TCRA and B2M ZFNs and donor with B2M homology arms): TCRA 120 ug/mL; B2M 60 ug/mL and AAV (pAAV B2M-hPGK GFP) 3E4vg/cell.
All experiments were conducted at 3e7 cells/ml cell density using the protocol as described in U.S. Patent Publication No. 2017/0137845 (extreme cold shock) and were cultured to cold shock at 30° C. overnight post electroporation.

The following day (day 4), cells were diluted to 0.5e6 cells/ml and transferred to cultures at 37° C. Three days later (day 7), cells diluted to 0.5e6 cells/ml again. After three and seven more days in culture (days 10 and 14, respectively), cells were harvested for FACS and MiSeq analysis (diluted to 0.5e6 cells/ml).

As shown in FIG. 6, GFP expression indicated that target integration was successful and that genetically modified cells comprising B2M and TCRA modifications (insertions and/or deletions) within the nuclease target sites (or within 1 to 50, 1-20, 1-10 or 1-5 base pairs of the nuclease target sites), including within the TTGAAA and TCAAAT (between the paired target sites) as disclosed herein were obtained.

Additional experiments were performed to generate cells with double-knockouts of TRAC and B2M and targeted integration of a donor vector. In particular, the TRAC-specific ZFN pair SBS #55266/SBS #53853 and the B2M pair SBS #57071/SBS #57531 were introduced into T-cells. Briefly, a 1:1 ratio of CD4:CD8 human T-Cells were thawed and activated with CD3/28 Dynabeads® (1:3 cells:bead ratio) in X-vivo15 T-cell culture media (day 0).

After 3 days in culture (day 3), cells were concentrated to 3e7 cells/mL in Maxcyte electroporation buffer in the presence of ZFN mRNA, then were electroporated using the Maxcyte device. Concentrated, electroporated cells were then placed in a tissue culture well, then AAV6 encoding for a hPGK-GFP-BGHpolyA transgene donor was added to the concentrated cells, which were allowed to recover and incubate at 37° C. for 20 minutes. Alternatively, the donor vector can be added to the electroporation buffer in the device. Cells were then diluted in culture medium to 3e6 cells/mL and cultured at 30° C. overnight. The next morning cells were diluted to 0.5e6 cells/mL in additional culture medium. The following is a description of the groups:
(a) Sham: cells electroporated with no ZFN mRNA or AAV donor added;
(b) TRAC and B2M ZFNs only, no donor): TRAC 120 ug/mL: B2M only 30 ug/mL;
(c) TRAC and B2M ZFNs and donor with B2M homology arms: TRAC 120 ug/mL; B2M 30 ug/mL and AAV6 (B2M-Site A-hPGK-eGFP) 3E4 vg/cell;
(d) TCAC and B2M ZFNs and donor with TRAC homology arms: TRAC 120 ug/mL; B2M 30 ug/mL; and AAV6 (TCRA-Site E-hPGK-eGFP) 3E4 vg/cell.

All experiments were conducted at 3e7 cells/ml cell density using the protocol as described in U.S. Patent Publication No. 2017/0137845 (extreme cold shock) and were cultured to cold shock at 30° C. overnight post electroporation. The following day (day 4), cells were diluted to 0.5e6 cells/mL and transferred to cultures at 37 C. Three days later (day 7), cells diluted to 0.5e6 cells/mL again. After three and seven more days in culture (days 10 and 14, respectively), cells were harvested for FACS and MiSeq analysis (diluted to 0.5e6 cells/mL).

Figure 7:
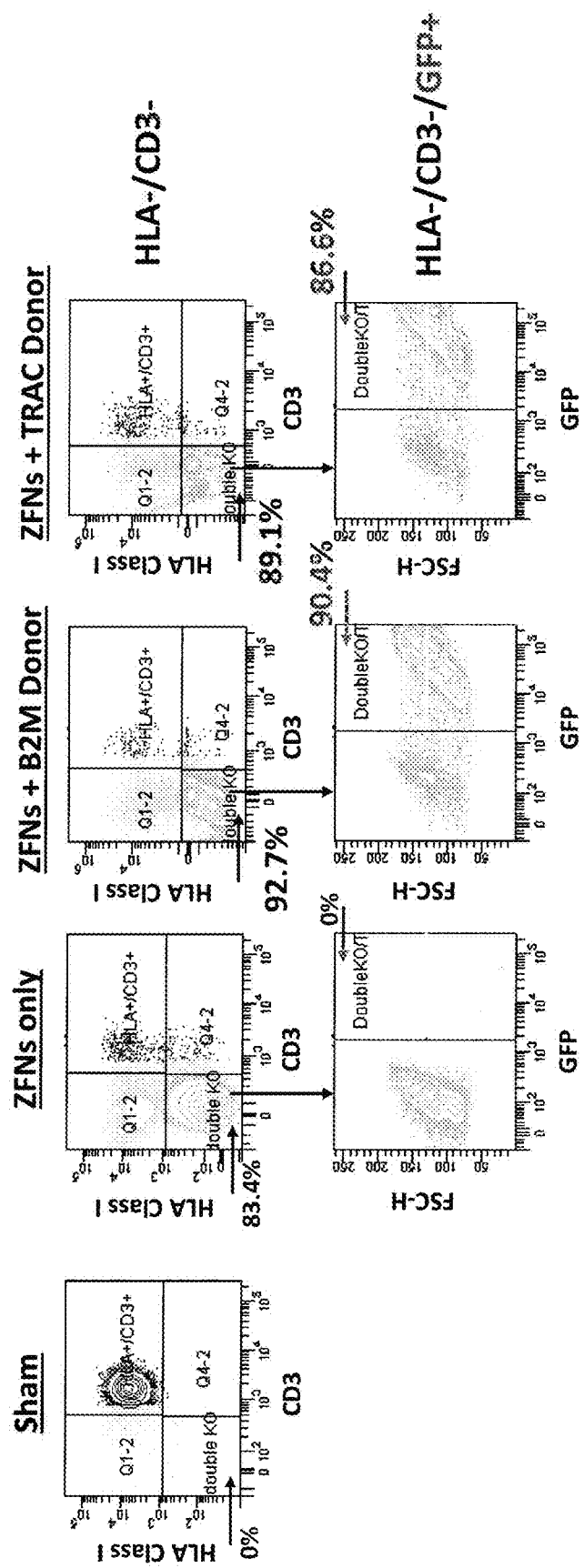
FIG. 7 shows FACS results from TRAC (TCRA) and B2M double knockout and targeted integration of a donor into either the TRAC (TCRA) or B2M locus. FACS results are shown for the indicated conditions (from left to right of upper panels: control (sham); TRAC and B2M ZFNs without a donor; TRAC and B2M ZFNs with donor targeted to B2M; and TRAC and B2M ZFNs with donor targeted to TRAC). The lower left quadrant of the top row of FACs plots shows cells with a double (TRAC/B2M) knockout and the right half of the bottom row of FACs plots shows cells with a double knockout and targeted integration. The percentage of cells is also indicated by arrows pointing towards the appropriate section of the FACs plot. As indicated by the arrows, 85-90% or more of cells were double KO and were also positive for targeted integration.

As shown in FIG. 7, GFP expression (donor) indicated that target integration was successful and that genetically modified cells comprising B2M and TRAC modifications (insertions and/or deletions) within the nuclease target sites (or within 1 to 50, 1-20, 1-10 or 1-5 base pairs of the nuclease target sites, including between paired sites) as disclosed herein were obtained with high frequency (including 80-90% knockout and targeted integration rates).

Experiments are also performed in which a CAR transgene is integrated into B2M and TCRA double-knockouts, either at the B2M, TCRA or another locus to created double B2M/TCRA knockouts that express a CAR.

Example 5: Optimization of TCRA and B2M ZFNs

To decrease off target cleavage, a strategy for nuclease optimization in which nonspecific phosphate contacts are selectively removed to bring about global suppression off-target cleavage (Guilinger, et al. (2014) *Nat Methods*. 11(4): 429-35. doi: 10.1038/nmeth.2845; Kleinstiver, et al. (2016) *Nature* 529(7587):490-5. doi: 10.1038/nature16526; Slaymaker, et al. (2016) *Science*) 351(6268):84-8. doi: 10.1126/science.aad5227) was adopted (see U.S. Patent Publication No. 2018/0087072). Amino acid substitutions were made at one or more key positions within the zinc finger framework that interacts with the phosphate backbone of the DNA (Pavletich and Pabo (1991) *Science* 252(5007):809-17; Elrod-Erickson, et al. (1996) *Structure* 4(10): 1171-80) as well as at positions in the right ZFN FokI domain also predicted to make a phosphate contact.

In Table 6 below, characterizing information for each ZFN is shown. Starting from the left, the SBS number (e.g., 55254) is displayed with the DNA target that the ZFN binds to displayed below the SBS number. Next are shown the amino acid recognition helix designs for fingers 1-6 or 1-5 (subdivided column 2 of Table 6). Also shown in Table 6 under the appropriate helix designs are mutations made to the ZFP backbone sequences of the indicated finger, as described in U.S. Patent Publication No. 2018/0087072. In the notation used in Table 6, "Qm5" means that at position minus 5 (relative to the helix which is numbered −1 to +6) of the indicated finger, the arginine at this position has been replaced with a glutamine (Q), while "Qm14" means that the arginine (R) normally present in position minus 14 has been replaced with a glutamine (Q). The abbreviation "n" as in nQm5 means that the mutation is in the N-terminal finger of the two-finger module used in the build of the 5 or 6 fingered protein. "None" indicates no changes outside the recognition helix region. Thus, for example, SBS #68797 includes the nQm5 mutation in fingers 1, 3 and 5 while fingers 2, 4 and 6 do not have mutations to the zinc finger backbone (e.g., the zinc finger sequence outside the recognition helix region).

Finally, the right-most column of Table 6 shows the linker used to link the DNA binding domain to the FokI cleavage domain (e.g., "L0" LRGSQLVKS (SEQ ID NO: 135), as referred to as the 'standard' linker, and described for example in U.S. Pat. No. 9,567,609) is displayed on top line of the column, with the sites of the FokI phosphate contact mutations and dimerization mutations shown in the box below the linker designation. Other linkers include N7c (SGAIRCHDEFWF, SEQ ID NO: 136) and N7a (SGTPHEVGVYTL, SEQ ID NO: 137). In specifics, indicated on top line of the Fok mutants box is the type of mutation found in the dimerizing domain (e.g., ELD or KKR as described for example in U.S. Pat. No. 8,962,281). Below the dimerization mutant designations is shown any mutations present in the FokI domain made to remove a nonspecific phosphate contact shown on the bottom (e.g., K525S or R416S where serine residues at amino acid positions 525 or 416 have been substituted for either a lysine or arginine, respectively as described in U.S. Publication No. 20180087072). Thus, for example, in SBS #68796, the linker is an L0 linker and the FokI cleavage domain includes the ELD dimerization mutants and no phosphate contact mutations. Further, for SBS #68812, the linker is an L0 linker and the FokI cleavage domain includes the KKR dimerization mutations where the FokI domain further comprises an R416E substitutional mutation.

Other FokI domain variants that may be used with the ZFPs described herein (including ZFPs derived from the ZFNs described herein) include the addition of a Sharkey mutation (S418P+K441E, see Guo, et al. (2010) J Mol Biol, doi:10.1016/j.jmb.2010.04.060) and the DAD and RVR FokI mutations (see U.S. Pat. No. 8,962,281). Non-limiting examples of engineered FokI variants that may be used include:

```
Wildtype FokI cleavage domain(SEQ ID NO: 139):
QLVKSELEEK KSELRHKLKY VPHEYIELIE IARNSTQDRI LEMKVMEFFM  384-433

KVYGYRGKHL GGSRKPDGAI YTVGSPIDYG VIVDTKAYSG GYNLPIGQAD  434-483

EMQRYVEENQ TRNKHINPNE WWKVYPSSVT EFKFLFVSGH FKGNYKAQLT  484-533

RLNHITNCNG AVLSVEELLI GGEMIKAGTL TLEEVRRKFN NGEINF      534-579

FokI-Sharkey (S418P + K441E, SEQ ID NO: 140):
QLVKSELEEK KSELRHKLKY VPHEYIELIE IARNPTQDRI LEMKVMEFFM  384-433

KVYGYRGEHL GGSRKPDGAI YTVGSPIDYG VIVDTKAYSG GYNLPIGQAD  434-483

EMQRYVEENQ TRNKHINPNE WWKVYPSSVT EFKFLFVSGH FKGNYKAQLT  484-533

RLNHITNCNG AVLSVEELLI GGEMIKAGTL TLEEVRRKFN NGEINF      534-579
```

```
FokI ELD (Q->E @ 486, I->L @499, N->D @496,
SEQ ID NO: 141)
QLVKSELEEK KSELRHKLKY VPHEYIELIE IARNSTQDRI LEMKVMEFFM    384-433

KVYGYRGKHL GGSRKPDGAI YTVGSPIDYG VIVDTKAYSG GYNLPIGQAD    434-483

EMERYVEENQ TRDKHLNPNE WWKVYPSSVT EFKFLFVSGH FKGNYKAQLT    484-533

RLNHITNCNG AVLSVEELLI GGEMIKAGTL TLEEVRRKFN NGEINF         534-579

FokI ELD, Sharkey (Q->E @ 486, I->L @499,
N->D @496, S418P + K441E SEQ ID NO: 142)
QLVKSELEEK KSELRHKLKY VPHEYIELIE IARNPTQDRI LEMKVMEFFM    384-433

KVYGYRGEHL GGSRKPDGAI YTVGSPIDYG VIVDTKAYSG GYNLPIGQAD    434-483

EMERYVEENQ TRDKHLNPNE WWKVYPSSVT EFKFLFVSGH FKGNYKAQLT    484-533

RLNHITNCNG AVLSVEELLI GGEMIKAGTL TLEEVRRKFN NGEINF         534-579

FokI ELD, R416E (Q->E @ 486, I->L @499,
N->D @496, R416E, SEQ ID NO: 143)
QLVKSELEEK KSELRHKLKY VPHEYIELIE IAENSTQDRI LEMKVMEFFM    384-433

KVYGYRGKHL GGSRKPDGAI YTVGSPIDYG VIVDTKAYSG GYNLPIGQAD    434-483

EMERYVEENQ TRDKHLNPNE WWKVYPSSVT EFKFLFVSGH FKGNYKAQLT    484-533

RLNHITNCNG AVLSVEELLI GGEMIKAGTL TLEEVRRKFN NGEINF         534-579

FokI ELD, Sharkey, R416 (Q->E @ 486, I->L @499,
N->D @496, S418P + K441E, R416E, SEQ ID NO: 144)
QLVKSELEEK KSELRHKLKY VPHEYIELIE IAENPTQDRI LEMKVMEFFM    384-433

KVYGYRGEHL GGSRKPDGAI YTVGSPIDYG VIVDTKAYSG GYNLPIGQAD    434-483

EMERYVEENQ TRDKHLNPNE WWKVYPSSVT EFKFLFVSGH FKGNYKAQLT    484-533

RLNHITNCNG AVLSVEELLI GGEMIKAGTL TLEEVRRKFN NGEINF         534-579

FokI ELD, R416Y (Q->E @ 486, I->L @499,
N->D @496, R416Y, SEQ ID NO: 145)
QLVKSELEEK KSELRHKLKY VPHEYIELIE IAYNSTQDRI LEMKVMEFFM    384-433

KVYGYRGKHL GGSRKPDGAI YTVGSPIDYG VIVDTKAYSG GYNLPIGQAD    434-483

EMERYVEENQ TRDKHLNPNE WWKVYPSSVT EFKFLFVSGH FKGNYKAQLT    484-533

RLNHITNCNG AVLSVEELLI GGEMIKAGTL TLEEVRRKFN NGEINF         534-579

FokI ELD, Sharkey, R416E (Q->E @ 486, I->L @499,
N->D @496, S418P + K441E, R416E, SEQ ID NO: 146)
QLVKSELEEK KSELRHKLKY VPHEYIELIE IAYNPTQDRI LEMKVMEFFM    384-433

KVYGYRGEHL GGSRKPDGAI YTVGSPIDYG VIVDTKAYSG GYNLPIGQAD    434-483

EMERYVEENQ TRDKHLNPNE WWKVYPSSVT EFKFLFVSGH FKGNYKAQLT    484-533

RLNHITNCNG AVLSVEELLI GGEMIKAGTL TLEEVRRKFN NGEINF         534-579

FokI ELD, S418E (Q->E @ 486, I->L @499,
N->D @496, S418E, SEQ ID NO: 147)
QLVKSELEEK KSELRHKLKY VPHEYIELIE IARNETQDRI LEMKVMEFFM    384-433

KVYGYRGKHL GGSRKPDGAI YTVGSPIDYG VIVDTKAYSG GYNLPIGQAD    434-483

EMERYVEENQ TRDKHLNPNE WWKVYPSSVT EFKFLFVSGH FKGNYKAQLT    484-533

RLNHITNCNG AVLSVEELLI GGEMIKAGTL TLEEVRRKFN NGEINF         534-579

FokI ELD, Sharkey partial, S418E (Q->E @ 486,
I->L @499, N->D @496, K441E, S418E,
SEQ ID NO: 148)
QLVKSELEEK KSELRHKLKY VPHEYIELIE IARNETQDRI LEMKVMEFFM    384-433

KVYGYRGEHL GGSRKPDGAI YTVGSPIDYG VIVDTKAYSG GYNLPIGQAD    434-483

EMERYVEENQ TRDKHLNPNE WWKVYPSSVT EFKFLFVSGH FKGNYKAQLT    484-533

RLNHITNCNG AVLSVEELLI GGEMIKAGTL TLEEVRRKFN NGEINF         534-579
```

```
FokI ELD, K525S (Q->E @ 486, I->L @499,
N->D @496, K525S, SEQ ID NO: 149)
QLVKSELEEK KSELRHKLKY VPHEYIELIE IARNSTQDRI LEMKVMEFFM    384-433

KVYGYRGKHL GGSRKPDGAI YTVGSPIDYG VIVDTKAYSG GYNLPIGQAD    434-483

EMERYVEENQ TRDKHLNPNE WWKVYPSSVT EFKFLFVSGH FSGNYKAQLT    484-533

RLNHITNCNG AVLSVEELLI GGEMIKAGTL TLEEVRRKFN NGEINF        534-579

FokI ELD, Sharkey K525S (Q->E @ 486, I->L @499,
N->D @496, S418P + K441E, K525S, SEQ ID NO: 150)
QLVKSELEEK KSELRHKLKY VPHEYIELIE IARNPTQDRI LEMKVMEFFM    384-433

KVYGYRGEHL GGSRKPDGAI YTVGSPIDYG VIVDTKAYSG GYNLPIGQAD    434-483

EMERYVEENQ TRDKHLNPNE WWKVYPSSVT EFKFLFVSGH FSGNYKAQLT    484-533

RLNHITNCNG AVLSVEELLI GGEMIKAGTL TLEEVRRKFN NGEINF        534-579

FokI ELD, I479T (Q->E @ 486, I->L @499,
N->D @496, I479T, SEQ ID NO: 151)
QLVKSELEEK KSELRHKLKY VPHEYIELIE IARNSTQDRI LEMKVMEFFM    384-433

KVYGYRGKHL GGSRKPDGAI YTVGSPIDYG VIVDTKAYSG GYNLPTGQAD    434-483

EMERYVEENQ TRDKHLNPNE WWKVYPSSVT EFKFLFVSGH FKGNYKAQLT    484-533

RLNHITNCNG AVLSVEELLI GGEMIKAGTL TLEEVRRKFN NGEINF        534-579

FokI ELD, Sharkey, I479T (Q->E @ 486, I->L @499,
N->D @496, S418P + K441E, I479T, SEQ ID NO: 152)
QLVKSELEEK KSELRHKLKY VPHEYIELIE IARNPTQDRI LEMKVMEFFM    384-433

KVYGYRGEHL GGSRKPDGAI YTVGSPIDYG VIVDTKAYSG GYNLPTGQAD    434-483

EMERYVEENQ TRDKHLNPNE WWKVYPSSVT EFKFLFVSGH FKGNYKAQLT    484-533

RLNHITNCNG AVLSVEELLI GGEMIKAGTL TLEEVRRKFN NGEINF        534-579

FokI ELD, P478D (Q->E @ 486, I->L @499,
N->D @496, P478D, SEQ ID NO: 153)
QLVKSELEEK KSELRHKLKY VPHEYIELIE IARNSTQDRI LEMKVMEFFM    384-433

KVYGYRGKHL GGSRKPDGAI YTVGSPIDYG VIVDTKAYSG GYNLDIGQAD    434-483

EMERYVEENQ TRDKHLNPNE WWKVYPSSVT EFKFLFVSGH FKGNYKAQLT    484-533

RLNHITNCNG AVLSVEELLI GGEMIKAGTL TLEEVRRKFN NGEINF        534-579

FokI ELD, Sharkey, P478D (Q->E @ 486, I->L @499,
N->D @496, S418P + K441E, P478D, SEQ ID NO: 154)
QLVKSELEEK KSELRHKLKY VPHEYIELIE IARNPTQDRI LEMKVMEFFM    384-433

KVYGYRGEHL GGSRKPDGAI YTVGSPIDYG VIVDTKAYSG GYNLDIGQAD    434-483

EMERYVEENQ TRDKHLNPNE WWKVYPSSVT EFKFLFVSGH FKGNYKAQLT    484-533

RLNHITNCNG AVLSVEELLI GGEMIKAGTL TLEEVRRKFN NGEINF        534-579

FokI ELD, Q481D (Q->E @ 486, I->L @499,
N->D @496, Q481D, SEQ ID NO: 155)
QLVKSELEEK KSELRHKLKY VPHEYIELIE IARNSTQDRI LEMKVMEFFM    384-433

KVYGYRGKHL GGSRKPDGAI YTVGSPIDYG VIVDTKAYSG GYNLPIGDAD    434-483

EMERYVEENQ TRDKHLNPNE WWKVYPSSVT EFKFLFVSGH FKGNYKAQLT    484-533

RLNHITNCNG AVLSVEELLI GGEMIKAGTL TLEEVRRKFN NGEINF        534-579

FokI ELD, Sharkey, Q481D (Q->E @ 486, I->L @499,
N->D @496, S418P + K441E, Q481D, SEQ ID NO: 156)
QLVKSELEEK KSELRHKLKY VPHEYIELIE IARNPTQDRI LEMKVMEFFM    384-433

KVYGYRGEHL GGSRKPDGAI YTVGSPIDYG VIVDTKAYSG GYNLPIGDAD    434-483

EMERYVEENQ TRDKHLNPNE WWKVYPSSVT EFKFLFVSGH FKGNYKAQLT    484-533

RLNHITNCNG AVLSVEELLI GGEMIKAGTL TLEEVRRKFN NGEINF        534-579
```

-continued

```
FokI KKR (E->K @490, I->K@538, H->R@537,
SEQ ID NO: 157)
QLVKSELEEK KSELRHKLKY VPHEYIELIE IARNSTQDRI LEMKVMEFFM    384-433

KVYGYRGKHL GGSRKPDGAI YTVGSPIDYG VIVDTKAYSG GYNLPIGQAD    434-483

EMQRYVKENQ TRNKHINPNE WWKVYPSSVT EFKFLFVSGH FKGNYKAQLT    484-533

RLNRKTNCNG AVLSVEELLI GGEMIKAGTL TLEEVRRKFN NGEINF        534-579

FokI KKR Sharkey, (E->K @490, I->K@538,
H->R@537, S418P + K441E, SEQ ID NO: 158)
QLVKSELEEK KSELRHKLKY VPHEYIELIE IARNPTQDRI LEMKVMEFFM    384-433

KVYGYRGEHL GGSRKPDGAI YTVGSPIDYG VIVDTKAYSG GYNLPIGQAD    434-483

EMQRYVKENQ TRNKHINPNE WWKVYPSSVT EFKFLFVSGH FKGNYKAQLT    484-533

RLNRKTNCNG AVLSVEELLI GGEMIKAGTL TLEEVRRKFN NGEINF        534-579

FokI KKR, Q481E (E->K @490, I->K@538,
H->R@537, Q481E, SEQ ID NO: 159)
QLVKSELEEK KSELRHKLKY VPHEYIELIE IARNSTQDRI LEMKVMEFFM    384-433

KVYGYRGKHL GGSRKPDGAI YTVGSPIDYG VIVDTKAYSG GYNLPIGEAD    434-483

EMQRYVKENQ TRNKHINPNE WWKVYPSSVT EFKFLFVSGH FKGNYKAQLT    484-533

RLNRKTNCNG AVLSVEELLI GGEMIKAGTL TLEEVRRKFN NGEINF        534-579

FokI KKR, Sharkey Q481E (E->K @490, I->K@538,
H->R@537, S418P + K441E, Q481E, SEQ ID NO: 160)
QLVKSELEEK KSELRHKLKY VPHEYIELIE IARNPTQDRI LEMKVMEFFM    384-433

KVYGYRGEHL GGSRKPDGAI YTVGSPIDYG VIVDTKAYSG GYNLPIGEAD    434-483

EMQRYVKENQ TRNKHINPNE WWKVYPSSVT EFKFLFVSGH FKGNYKAQLT    484-533

RLNRKTNCNG AVLSVEELLI GGEMIKAGTL TLEEVRRKFN NGEINF        534-579

FokI KKR, R416E (E->K @490, I->K@538,
H->R@537, R416E, SEQ ID NO: 161)
QLVKSELEEK KSELRHKLKY VPHEYIELIE IAENSTQDRI LEMKVMEFFM    384-433

KVYGYRGKHL GGSRKPDGAI YTVGSPIDYG VIVDTKAYSG GYNLPIGQAD    434-483

EMQRYVKENQ TRNKHINPNE WWKVYPSSVT EFKFLFVSGH FKGNYKAQLT    484-533

RLNRKTNCNG AVLSVEELLI GGEMIKAGTL TLEEVRRKFN NGEINF        534-579

FokI KKR, Sharkey, R416E (E->K @490, I->K@538,
H->R@537, S418P + K441E, R416E, SEQ ID NO: 162)
QLVKSELEEK KSELRHKLKY VPHEYIELIE IAENPTQDRI LEMKVMEFFM    384-433

KVYGYRGEHL GGSRKPDGAI YTVGSPIDYG VIVDTKAYSG GYNLPIGQAD    434-483

EMQRYVKENQ TRNKHINPNE WWKVYPSSVT EFKFLFVSGH FKGNYKAQLT    484-533

RLNRKTNCNG AVLSVEELLI GGEMIKAGTL TLEEVRRKFN NGEINF        534-579

FokI KKR, K525S (E->K @490, I->K@538,
H->R@537, K525S, SEQ ID NO: 163)
QLVKSELEEK KSELRHKLKY VPHEYIELIE IARNSTQDRI LEMKVMEFFM    384-433

KVYGYRGKHL GGSRKPDGAI YTVGSPIDYG VIVDTKAYSG GYNLPIGQAD    434-483

EMQRYVKENQ TRNKHINPNE WWKVYPSSVT EFKFLFVSGH FSGNYKAQLT    484-533

RLNRKTNCNG AVLSVEELLI GGEMIKAGTL TLEEVRRKFN NGEINF        534-579

FokI KKR, Sharkey, K525S (E->K @490, I->K@538,
H->R@537, S418P + K441E, K525S, SEQ ID NO: 164)
QLVKSELEEK KSELRHKLKY VPHEYIELIE IARNPTQDRI LEMKVMEFFM    384-433

KVYGYRGEHL GGSRKPDGAI YTVGSPIDYG VIVDTKAYSG GYNLPIGQAD    434-483

EMQRYVKENQ TRNKHINPNE WWKVYPSSVT EFKFLFVSGH FSGNYKAQLT    484-533

RLNRKTNCNG AVLSVEELLI GGEMIKAGTL TLEEVRRKFN NGEINF        534-579
```

```
FokI KKR, R416Y (E->K @490, I->K@538,
H->R@537, R416Y, SEQ ID NO: 165)
QLVKSELEEK KSELRHKLKY VPHEYIELIE IAYNSTQDRI LEMKVMEFFM    384-433

KVYGYRGKHL GGSRKPDGAI YTVGSPIDYG VIVDTKAYSG GYNLPIGQAD    434-483

EMQRYVKENQ TRNKHINPNE WWKVYPSSVT EFKFLFVSGH FKGNYKAQLT    484-533

RLNRKTNCNG AVLSVEELLI GGEMIKAGTL TLEEVRRKFN NGEINF        534-579

FokI KKR, Sharkey, R416Y (E->K @490, I->K@538,
H->R@537, S418P + K441E, R416Y, SEQ ID NO: 166)
QLVKSELEEK KSELRHKLKY VPHEYIELIE IAYNPTQDRI LEMKVMEFFM    384-433

KVYGYRGEHL GGSRKPDGAI YTVGSPIDYG VIVDTKAYSG GYNLPIGQAD    434-483

EMQRYVKENQ TRNKHINPNE WWKVYPSSVT EFKFLFVSGH FKGNYKAQLT    484-533

RLNRKTNCNG AVLSVEELLI GGEMIKAGTL TLEEVRRKFN NGEINF        534-579

FokI, KKR I479T (E->K @490, I->K@538,
H->R@537, I479T, SEQ ID NO: 167)
QLVKSELEEK KSELRHKLKY VPHEYIELIE IARNSTQDRI LEMKVMEFFM    384-433

KVYGYRGKHL GGSRKPDGAI YTVGSPIDYG VIVDTKAYSG GYNLPTGQAD    434-483

EMQRYVKENQ TRNKHINPNE WWKVYPSSVT EFKFLFVSGH FKGNYKAQLT    484-533

RLNRKTNCNG AVLSVEELLI GGEMIKAGTL TLEEVRRKFN NGEINF        534-579

FokI, KKR Sharkey I479T (E->K @490, I->K@538,
H->R@537, S418P + K441E, I479T, SEQ ID NO: 168)
QLVKSELEEK KSELRHKLKY VPHEYIELIE IARNPTQDRI LEMKVMEFFM    384-433

KVYGYRGEHL GGSRKPDGAI YTVGSPIDYG VIVDTKAYSG GYNLPTGQAD    434-483

EMQRYVKENQ TRNKHINPNE WWKVYPSSVT EFKFLFVSGH FKGNYKAQLT    484-533

RLNRKTNCNG AVLSVEELLI GGEMIKAGTL TLEEVRRKFN NGEINF        534-579

FokI, KKR P478D(E->K @490, I->K@538,
H->R@537, P478D, SEQ ID NO: 169)
QLVKSELEEK KSELRHKLKY VPHEYIELIE IARNSTQDRI LEMKVMEFFM    384-433

KVYGYRGKHL GGSRKPDGAI YTVGSPIDYG VIVDTKAYSG GYNLDIGQAD    434-483

EMQRYVKENQ TRNKHINPNE WWKVYPSSVT EFKFLFVSGH FKGNYKAQLT    484-533

RLNRKTNCNG AVLSVEELLI GGEMIKAGTL TLEEVRRKFN NGEINF        534-579

FokI, KKR Sharkey P478D(E->K @490, I->K@538,
H->R@537, P478D, SEQ ID NO: 170)
QLVKSELEEK KSELRHKLKY VPHEYIELIE IARNPTQDRI LEMKVMEFFM    384-433

KVYGYRGEHL GGSRKPDGAI YTVGSPIDYG VIVDTKAYSG GYNLDIGQAD    434-483

EMQRYVKENQ TRNKHINPNE WWKVYPSSVT EFKFLFVSGH FKGNYKAQLT    484-533

RLNRKTNCNG AVLSVEELLI GGEMIKAGTL TLEEVRRKFN NGEINF        534-579

FokI DAD (R->D@487, N->D@496,
I->A@499, SEQ ID NO: 171)
QLVKSELEEK KSELRHKLKY VPHEYIELIE IARNSTQDRI LEMKVMEFFM    384-433

KVYGYRGKHL GGSRKPDGAI YTVGSPIDYG VIVDTKAYSG GYNLPIGQAD    434-483

EMQDYVEENQ TRDKHANPNE WWKVYPSSVT EFKFLFVSGH FKGNYKAQLT    484-533

RLNHITNCNG AVLSVEELLI GGEMIKAGTL TLEEVRRKFN NGEINF        534-579

FokI DAD Sharkey (R->D@487, N->D@496,
I->A@499, S418P + K441E, SEQ ID NO: 172)
QLVKSELEEK KSELRHKLKY VPHEYIELIE IARNPTQDRI LEMKVMEFFM    384-433

KVYGYRGEHL GGSRKPDGAI YTVGSPIDYG VIVDTKAYSG GYNLPIGQAD    434-483

EMQDYVEENQ TRDKHANPNE WWKVYPSSVT EFKFLFVSGH FKGNYKAQLT    484-533

RLNHITNCNG AVLSVEELLI GGEMIKAGTL TLEEVRRKFN NGEINF        534-579
```

-continued

```
FokI RVR (D->R@483, H->R@537,
I->V@538, SEQ ID NO: 173)
QLVKSELEEK KSELRHKLKY VPHEYIELIE IARNSTQDRI LEMKVMEFFM    384-433

KVYGYRGKHL GGSRKPDGAI YTVGSPIDYG VIVDTKAYSG GYNLPIGQAR    434-483

EMQRYVEENQ TRNKHINPNE WWKVYPSSVT EFKFLFVSGH FKGNYKAQLT    484-533

RLNRVTNCNG AVLSVEELLI GGEMIKAGTL TLEEVRRKFN NGEINF        534-579

FokI RVR Sharkey (D->R@483, H->R@537,
I->V@538, S418P + K441E, SEQ ID NO: 174)
QLVKSELEEK KSELRHKLKY VPHEYIELIE IARNPTQDRI LEMKVMEFFM    384-433

KVYGYRGEHL GGSRKPDGAI YTVGSPIDYG VIVDTKAYSG GYNLPIGQAR    434-483

EMQRYVEENQ TRNKHINPNE WWKVYPSSVT EFKFLFVSGH FKGNYKAQLT    484-533

RLNRVTNCNG AVLSVEELLI GGEMIKAGTL TLEEVRRKFN NGEINF        534-579
```

All pairwise combinations of ZFNs were tested for functionality and all were found to be active.

TABLE 6

ZFN pairs specific for TCRA

| SBS # (target site, 5'-3') | Design [Helix Sequence, SEQ ID] [Mutations to finger backbone] | | | | | | Linker Fok mutants |
|---|---|---|---|---|---|---|---|
| | F1 | F2 | F3 | F4 | F5 | F6 | |
| Site D Left partner | | | | | | | |
| 55254 5' ctCC TGAAAGT GGCCGGg ttttaatc tgc (SEQ ID NO: 13) | RSDHLST (SEQ ID NO: 47) none | DRSHLAR (SEQ ID NO: 48) none | LKQHLNE (SEQ ID NO: 49) none | QSGNLAR (SEQ ID NO: 34) none | HNSSLKD (SEQ ID NO: 54) none | N/A N/A | L0 ELD C-term Fok |
| 68796 ctCCTGA AAGTGGC CGGgttt aatctgc (SEQ ID NO: 13) | RSDHLST (SEQ ID NO: 47) nQm5 | DRSHLAR (SEQ ID NO: 48) none | LKQHLNE (SEQ ID NO: 49) nQm5s | QSGNLAR (SEQ ID NO: 34) nQm5 | HNSSLKD (SEQ ID NO: 54) none | N/A N/A | L0 ELD C-term Fok |
| 68812 ctCCTGA AAGTGGC CGGgttt aatctgc (SEQ ID NO: 13) | RSDHLST (SEQ ID NO: 47) nQm5 | DRSHLAR (SEQ ID NO: 48) none | LKQHLNE (SEQ ID NO: 49) nQm5s | QSGNLAR (SEQ ID NO: 34) nQm5 | HNSSLKD (SEQ ID NO: 54) none | N/A N/A | L0 ELD R416E C-term Fok |
| 68820 ctCCTGA AAGTGGC CGGgttt aatctgc (SEQ ID NO: 13) | RSDHLST (SEQ ID NO: 47) none | DRSHLAR (SEQ ID NO: 48) none | LKQHLNE (SEQ ID NO: 49) none | QSGNLAR (SEQ ID NO: 34) none | HNSSLKD (SEQ ID NO: 54) none | N/A N/A | L0 ELD S418E C-term Fok |
| 68876 ctCCTGA AAGTGGC CGGgttt aatctgc (SEQ ID NO: 13) | RSDHLST (SEQ ID NO: 47) nQm5 | DRSHLAR (SEQ ID NO: 48) none | LKQHLNE (SEQ ID NO: 49) nQm5s | QSGNLAR (SEQ ID NO: 34) nQm5 | HNSSLKD (SEQ ID NO: 54) none | N/A N/A | L0 ELD K525S C-term Fok |

TABLE 6-continued

ZFN pairs specific for TCRA

| SBS # (target site, 5'-3') | Design [Helix Sequence, SEQ ID] [Mutations to finger backbone] | | | | | | Linker Fok mutants |
|---|---|---|---|---|---|---|---|
| | F1 | F2 | F3 | F4 | F5 | F6 | |

Right partner

| 55248 5'agGAT TCGGAAC CCAATCA Ctgacag gt (SEQ ID NO: 14) | DQSNLRA (SEQ ID NO: 42) none | TSSNRKT (SEQ ID NO: 43) none | LQQTLAD (SEQ ID NO: 51) none | QSGNLAR (SEQ ID NO: 34) none | RREDLIT (SEQ ID NO: 52) none | TSSNLSR (SEQ ID NO: 53) none | L0 KKR C-term Fok |
| 68797 agGATTC GGAACCC AATCACt gacaggt (SEQ ID NO: 14) | DQSNLRA (SEQ ID NO: 42) nQm5 | TSSNRKT (SEQ ID NO: 43) none | LQQTLAD (SEQ ID NO: 51) nQm5 | QSGNLAR (SEQ ID NO: 34) none | RREDLIT (SEQ ID NO: 52) nQm5 | TSSNLSR (SEQ ID NO: 53) none | L0 KKR C-term Fok |
| 68813 agGATTC GGAACCC AATCACt gacaggt (SEQ ID NO: 14) | DQSNLRA (SEQ ID NO: 42) nQm5 | TSSNRKT (SEQ ID NO: 43) none | LQQTLAD (SEQ ID NO: 51) nQm5 | QSGNLAR (SEQ ID NO: 34) none | RREDLIT (SEQ ID NO: 52) nQm5 | TSSNLSR (SEQ ID NO: 53) none | L0 KKR R416E C-term Fok |
| 68861 agGATTC GGAACCC AATCACt gacaggt (SEQ ID NO: 14) | DQSNLRA (SEQ ID NO: 42) nQm5 | TSSNRKT (SEQ ID NO: 43) none | LQQTLAD (SEQ ID NO: 51) nQm5 | QSGNLAR (SEQ ID NO: 34) none | RREDLIT (SEQ ID NO: 52) nQm5 | TSSNLSR (SEQ ID NO: 53) none | L0 KKR Q481E C-term Fok |
| 68877 agGATTC GGAACCC AATCACt gacaggt (SEQ ID NO: 14) | DQSNLRA (SEQ ID NO: 42) nQm5 | TSSNRKT (SEQ ID NO: 43) none | LQQTLAD (SEQ ID NO: 51) nQm5 | QSGNLAR (SEQ ID NO: 34) none | RREDLIT (SEQ ID NO: 52) nQm5 | TSSNLSR (SEQ ID NO: 53) none | L0 KKR K525S C-term Fok |

Site E
Left partner

| 55266 tcAAGCT GGTCGAG aAAAGCT tttgaaac (SEQ ID NO: 15) | QSSDLSR (SEQ ID NO: 57) none | QSGNRTT (SEQ ID NO: 58) none | RSANLAR (SEQ ID NO: 59) none | DRSALAR (SEQ ID NO: 33) none | RSDVLSE (SEQ ID NO: 60) none | KHSTRRV (SEQ ID NO: 61) none | N7c ELD N-term Fok |
| 68798 tcAAGCT GGTCGAG aAAAGCT tttgaaac (SEQ ID NO: 15) | QSSDLSR (SEQ ID NO: 57) nQm5 | QSGNRTT (SEQ ID NO: 58) none | RSANLAR (SEQ ID NO: 59) nQm5 | DRSALAR (SEQ ID NO: 33) none | RSDVLSE (SEQ ID NO: 60) nQm5 | KHSTRRV (SEQ ID NO: 61) none | N7c ELD N-term Fok |
| 68846 tcAAGCT GGTCGAG aAAAGCT tttgaaac (SEQ ID NO: 15) | QSSDLSR (SEQ ID NO: 57) nQm5 | QSGNRTT (SEQ ID NO: 58) none | RSANLAR (SEQ ID NO: 59) nQm5 | DRSALAR (SEQ ID NO: 33) none | RSDVLSE (SEQ ID NO: 60) nQm5 | KHSTRRV (SEQ ID NO: 61) none | N7c ELD I479T N-term Fok |

TABLE 6-continued

ZFN pairs specific for TCRA

| SBS # (target site, 5'-3') | Design [Helix Sequence, SEQ ID] [Mutations to finger backbone] | | | | | | Linker Fok mutants |
|---|---|---|---|---|---|---|---|
| | F1 | F2 | F3 | F4 | F5 | F6 | |
| | Right partner | | | | | | |
| 53853 aaCAGGT AaGACAG GGGTCTA gcctggg (SEQ ID NO: 16) | TMHQRVE (SEQ ID NO: 62) none | TSGHLSR (SEQ ID NO: 63) none | RSDHLTQ (SEQ ID NO: 64) none | DSANLSR (SEQ ID NO: 65) none | QSGSLTR (SEQ ID NO: 66) none | AKWNLDA (SEQ ID NO: 67) none | L0 KKR C-term Fok |
| 68879 aaCAGGT AaGACAG GGGTCTA gcctggg (SEQ ID NO: 16) | TMHQRVE (SEQ ID NO: 62) nQm5 | TSGHLSR (SEQ ID NO: 63) none | RSDHLTQ (SEQ ID NO: 64) nQm5 | DSANLSR (SEQ ID NO: 65) none | QSGSLTR (SEQ ID NO: 66) nQm5 | AKWNLDA (SEQ ID NO: 67) none | L0 KKR K525S C-term Fok |
| 68815 aaCAGGT AaGACAG GGGTCTA gcctggg (SEQ ID NO: 16) | TMHQRVE (SEQ ID NO: 62) nQm5 | TSGHLSR (SEQ ID NO: 63) none | RSDHLTQ (SEQ ID NO: 64) nQm5 | DSANLSR (SEQ ID NO: 65) none | QSGSLTR (SEQ ID NO: 66) nQm5 | AKWNLDA (SEQ ID NO: 67) none | L0 KKR R416E C-term Fok |
| 68799 aaCAGGT AaGACAG GGGTCTA gcctggg (SEQ ID NO: 16) | TMHQRVE (SEQ ID NO: 62) nQm5 | TSGHLSR (SEQ ID NO: 63) none | RSDHLTQ (SEQ ID NO: 64) nQm5 | DSANLSR (SEQ ID NO: 65) none | QSGSLTR (SEQ ID NO: 66) nQm5 | AKWNLDA (SEQ ID NO: 67) none | L0 KKR C-term Fok |

Genes encoding the ZFNs for each site were cloned into an expression plasmid as right and left partners separated by a 2A self-cleaving peptide in combinations for each target site. mRNA encoding the ZFNs were derived using standard in vitro transcription methods. Activated T cells (3 days post activation) were then treated with the various mRNAs at 3 different doses (12, 6 or 3 μg in 100 μL, 3E6 T-cells) by electroporation. 4 days post electroporation, the cells were analyzed for cleavage at the target sites and at the target site. The data are presented below in two tables (one for each target site).

TABLE 7a

On Target and Off Target cleavage at Site D

| | SITE D | 55254--2A-55248 | 68796-2A-68813 | 68813-2A-68796 | 68796-2A-68861 | 68861-2A-68796 | 68812-2A-68813 | 68813-2A-68812 | 68876-2A-68877 | 68877-2A-68876 | Control |
|---|---|---|---|---|---|---|---|---|---|---|---|
| On Target | 12 ug | 96.7 | 99.3 | 98.8 | 99.4 | 99.3 | 99.9 | 99.9 | 99.2 | 99.1 | 0.12 |
| | 6 ug | 98.5 | 99.2 | 99.1 | 99.4 | 99.4 | 99 | 98.9 | 99.3 | 99.2 | 0.14 |
| | 3 ug | 96 | 99.1 | 98.8 | 99.3 | 98.9 | 98.3 | 97.8 | 98.7 | 99.3 | 0.15 |
| Off D1 | 12 ug | 39.6 | 0.29 | 0.35 | 0.21 | 0.18 | 0.25 | 0.25 | 0.2 | 0.2 | 0.28 |
| | 6 ug | 18 | 0.25 | 0.3 | 0.25 | 0.2 | 0.28 | 0.22 | 0.29 | 0.23 | 0.34 |
| | 3 ug | 7.3 | 0.28 | 0.24 | 0.46 | 0.26 | 0.24 | 0.27 | 0.22 | 0.25 | 0.26 |
| 12 μg | off sum | 42.22 | 1.67 | 1.53 | 3.17 | 1.19 | 1.46 | 1.74 | 1.33 | 2.05 | 1.28 |
| | on/off | 2.3 | 59 | 65 | 31 | 84 | 68 | 57 | 75 | 48 | 0.09 |
| 6 μg | off sum | 19.14 | 5.94 | 1.53 | 1.53 | 1.06 | 1.28 | 1.36 | 1.3 | 1.32 | 1.22 |
| | on/off | 5.1 | 17 | 65 | 65 | 94 | 77 | 73 | 76 | 75 | 0.12 |
| 3 μg | off sum | 8.28 | 4.3 | 1.18 | 1.56 | 1.29 | 1.22 | 1.54 | 1.21 | 8.13 | 1.2 |
| | on/off | 12 | 23 | 83 | 63 | 77 | 81 | 63 | 82 | 12 | 0.13 |
| | sum off | 69.63 | 11.91 | 4.23 | 6.26 | 3.54 | 3.96 | 4.64 | 3.84 | 11.5 | 3.7 |
| | Ave. on/off | 6.3 | 33 | 71 | 53 | 85 | 75 | 65 | 77 | 45 | 0.11 |

TABLE 7b

On Target and Off Target cleavage at Site E

| | SITE E | 55266-2A-53853 | 55266-2A-68815 | 68815-2A-55266 | 55266-2A-68879 | 68879-2A-55266 | 68798-2A-68815 | 68815-2A-68798 | 68846-2A-53853 | 53853-2A-68846 | Site E control |
|---|---|---|---|---|---|---|---|---|---|---|---|
| On Target | 12 ug | 96.7 | 97.6 | 86.5 | 96.3 | 95.5 | 97.5 | 96.4 | 96.5 | 97 | 0.19 |
| | 6 ug | 95.3 | 94.6 | 81.3 | 95.2 | 91.5 | 96.5 | 97.2 | 94.4 | NA | 0.34 |
| | 3 ug | 95.3 | NA | NA | NA | NA | NA | NA | NA | NA | 0.17 |
| Off E1 | 12 ug | 1.24 | 0.32 | 0.23 | 0.24 | 0.3 | 0.23 | 0.27 | 0.19 | 0.21 | 0.29 |
| | 6 ug | 0.79 | 0.23 | 0.24 | 0.27 | 0.25 | 0.22 | 0.22 | 0.18 | 0.23 | 0.25 |
| | 3 ug | 0.5 | 0.26 | 0.18 | 0.2 | 0.23 | 0.2 | 0.23 | 0.23 | 0.23 | 0.26 |
| Off E2 | 12 ug | 19.69 | 1.05 | 0.51 | 0.95 | 1.04 | 0.37 | 0.36 | 0.18 | 0.23 | 0.24 |
| | 6 ug | 11.09 | NA | 0.34 | 0.67 | 0.69 | 0.31 | 0.26 | 0.17 | 0.22 | 0.17 |
| | 3 ug | 4.05 | 0.36 | 0.28 | 0.34 | 0.33 | 0.24 | 0.26 | 0.23 | 0.22 | 0.13 |
| Off E3 | 12 ug | 4.32 | 0.14 | 0.19 | 0.4 | 0.19 | 0.17 | 0.19 | 0.18 | 0.16 | 0.19 |
| | 6 ug | 1.33 | 0.13 | 0.13 | 0.21 | 0.17 | 0.19 | 0.14 | 0.11 | 0.19 | 0.21 |
| | 3 ug | 0.47 | 0.13 | 0.15 | 0.2 | 0.18 | 0.14 | 0.15 | 0.12 | 0.1 | 0.14 |
| 12 ug | off sum | 25.24 | 1.51 | 0.93 | 1.59 | 1.53 | 0.77 | 0.82 | 0.54 | 0.6 | 0.71 |
| | on/off | 3.8 | 65 | 93 | 61 | 62 | 127 | 117 | 177 | 161 | 0.27 |
| 6 ug | off sum | 13.21 | 0.36 | 0.72 | 1.15 | 1.11 | 0.72 | 0.61 | 0.46 | 0.64 | 0.63 |
| | on/off | 7.2 | 261 | 113 | 83 | 82 | 135 | 160 | 204 | NA | 0.54 |
| 3 ug | off sum | 5.02 | 0.74 | 0.61 | 0.74 | 0.74 | 0.57 | 0.64 | 0.58 | 0.55 | 0.52 |
| | on/off | 18.98 | NA | NA | NA | NA | NA | NA | NA | NA | 0.32 |
| sum off | | 43.47 | 2.62 | 2.26 | 3.48 | 3.38 | 2.06 | 2.07 | 1.59 | 1.79 | 1.86 |
| Ave. on/off | | 10 | 163 | 103 | 72 | 72 | 131 | 139 | 191 | 161 | 0.38 |

Thus, following modifications, the ZFN reagents maintained the excellent on-target cutting activity, often while diminishing off-target cleavage activity to background (compare for example, the on-target cleavage activity of the parental 55254/55248 pair with the modified 68861/68796 pair, showing 96.7 and 99.3 percent on target cleavage at the saturating doses of 12 µg, respectively, while also having a total off target activity as this dose of 42.22 percent in the parent pair and 1.19% in the modified pair—similar to the control level of 1.28.

As with the TRAC ZFNs: potential phosphate contacting amino acids were modified in the FokI domain of the B2M proteins. Exemplary modifications of the ZFP components ("designs") are shown below in Table 8.

TABLE 8

B2M-specific ZFN optimization

| SBS # (target site, 5'-3') | Design [Helix Sequence, SEQ ID] [Mutations to finger backbone] | | | | | | Linker Fok mutants |
|---|---|---|---|---|---|---|---|
| | F1 | F2 | F3 | F4 | F5 | F6 | |
| SBS57531 5' gaGTAGCG cGAGCACA GCtaaggc cacg (SEQ ID NO: 126) | AQCCLFH (SEQ ID NO: 128) | DQSNLRA (SEQ ID NO: 42) | RSANLTR (SEQ ID NO: 129) | RSDDLTR (SEQ ID NO: 130) | QSGSLTR (SEQ ID NO: 66) | N/A | N6a KKR N-term Fok |
| SBS68957 5' gaGTAGCG cGAGCACA GCtaaggc cacg (SEQ ID NO: 126) | AQCCLFH (SEQ ID NO: 128) none | DQSNLRA (SEQ ID NO: 42) none | RSANLTR (SEQ ID NO: 129) None | RSDDLTR (SEQ ID NO: 130) none | QSGSLTR (SEQ ID NO: 66) none | N/A N/A | N6a KKR K525S N-term Fok |

TABLE 8-continued

B2M-specific ZFN optimization

| SBS # (target site, 5'-3') | Design [Helix Sequence, SEQ ID] [Mutations to finger backbone] | | | | | | Linker Fok mutants |
|---|---|---|---|---|---|---|---|
| | F1 | F2 | F3 | F4 | F5 | F6 | |
| SBS72678 5' gaGTAGCG cGAGCACA GCtaaggc cacg (SEQ ID NO: 126) | AQCCLFH (SEQ ID NO: 128) none | DQSNLRA (SEQ ID NO: 42) none | RSANLTR (SEQ ID NO: 129) None | RSDDLTR (SEQ ID NO: 130) none | QSGSLTR (SEQ ID NO: 66) none | N/A N/A | N6a KKR R416Y N-term Fok |
| SBS57071 gcCACGGA gCGAGACA TCTCGgcc cgaa (SEQ ID NO: 127) | RSDDLSK (SEQ ID NO: 131) | DSSARKK (SEQ ID NO: 132) | DRSNLSR (SEQ ID NO: 22) | QRTHLRD (SEQ ID NO: 133) | QSGHLAR (SEQ ID NO: 29) | DSSNREA (SEQ ID NO: 134) | L0 ELD C-term Fok |
| SBS72732 gcCACGGA gCGAGACA TCTCGgcc cgaa (SEQ ID NO: 127) | RSDDLSK (SEQ ID NO: 131) none | DSSARKK (SEQ ID NO: 132) none | DRSNLSR (SEQ ID NO: 22) None | QRTHLRD (SEQ ID NO: 133) none | QSGHLAR (SEQ ID NO: 29) none | DSSNREA (SEQ ID NO: 134) none | L0 ELD P478D C-term Fok |
| SBS72748 gcCACGGA gCGAGACA TCTCGgcc cgaa (SEQ ID NO: 127) | RSDDLSK (SEQ ID NO: 131) none | DSSARKK (SEQ ID NO: 132) none | DRSNLSR (SEQ ID NO: 22) None | QRTHLRD (SEQ ID NO: 133) none | QSGHLAR (SEQ ID NO: 29) none | DSSNREA (SEQ ID NO: 134) N/A | L0 ELD Q481D C-term Fok |

The modified B2M reagents were tested for activity as above and were analyzed for phenotypic knockout by FACs analysis using an antibody specific for HLA. All pairwise combinations (57531/57071; 57531/72732; 57531/72748; 68957/57071; 68957/72732; 68957/72748; 72678/57071; 72678/72732; 72678/72748) were found be active with exemplary results for the indicated pairs shown below in Table 9 and demonstrate that the modified variants are active.

TABLE 9

Phenotypic analysis of B2M-specific ZFN

| | ZFN Concentration (µg/mL) | | | |
|---|---|---|---|---|
| ZFN pair (2A mRNA) | 30 | 60 | 90 | 120 |
| | % Indels | | | |
| 57071/68957 | 74 | 79 | 83 | 81 |
| 72732/57531 | 83 | 86 | 87 | 85 |
| 72732/72678 | 86 | nt | nt | 87 |
| 72748/68957 | 37 | nt | nt | 80 | nt: not tested.

On- and off-target analyses were also carried out using MiSeq for each of the pairs listed above in Table 9. The results are shown below for each pair in tables 10A-10D, and demonstrate that these reagents are highly specific.

TABLE 10A

Off target analysis for 57071/68957 pair

| | ZFP | | GFP | | | |
|---|---|---|---|---|---|---|
| 57071/68957 | corrected | raw | corrected | raw | p-value | curation |
| Target | 91.64 | 91.94 | 0.19 | 0.25 | 0.00 | positive |
| OT1 | 0.08 | 0.39 | 0.04 | 0.35 | 0.12 | negative |
| OT2 | 0.03 | 0.33 | 0.01 | 0.24 | 0.06 | negative |
| OT3 | 0.08 | 1.22 | 0.03 | 1.00 | 0.05 | negative |
| OT4 | 0.02 | 0.16 | 0.03 | 0.14 | 1.00 | negative |
| OT5 | 0.04 | 0.48 | 0.02 | 0.41 | 1.00 | negative |
| OT6 | 0.04 | 0.27 | 0.03 | 0.22 | 1.00 | maybe |
| OT7 | nt | nt | nt | nt | nt | nt |
| OT8 | 0.02 | 0.18 | 0.02 | 0.13 | 1.00 | negative |
| OT9 | 0.04 | 0.72 | 0.06 | 0.58 | 1.00 | negative |
| OT10 | 0.03 | 0.15 | 0.03 | 0.12 | 1.00 | negative |

TABLE 10B

Off target analysis for 72732/57531 pair

| | ZFP | | GFP | | | |
|---|---|---|---|---|---|---|
| 72732/57531 | corrected | raw | corrected | raw | p-value | curation |
| Target | 95.75 | 96.88 | 0.25 | 0.31 | 0.00 | positive |
| OT1 | 0.03 | 0.26 | 0.02 | 0.26 | 1.00 | negative |
| OT2 | 0.08 | 0.52 | 0.06 | 0.41 | 1.00 | negative |
| OT3 | 0.06 | 0.19 | 0.05 | 0.21 | 1.00 | negative |
| OT4 | 0.06 | 0.47 | 0.04 | 0.40 | 1.00 | negative |
| OT5 | 0.03 | 0.19 | 0.02 | 0.19 | 1.00 | negative |

TABLE 10B-continued

Off target analysis for 72732/57531 pair

| 72732/57531 | ZFP corrected | raw | GFP corrected | raw | p-value | curation |
|---|---|---|---|---|---|---|
| OT6 | 0.02 | 0.77 | 0.02 | 0.84 | 1.00 | negative |
| OT7 | 0.04 | 0.98 | 0.06 | 0.79 | 1.00 | negative |
| OT8 | 0.07 | 7.42 | 0.07 | 7.45 | 1.00 | negative |
| OT9 | 0.02 | 0.14 | 0.02 | 0.16 | 1.00 | negative |
| OT10 | 0.03 | 0.27 | 0.03 | 0.28 | 1.00 | negative |

TABLE 10C

Off target analysis for 72732/72678 pair

| 72732/72678 | ZFP corrected | raw | GFP corrected | raw | p-value | curation |
|---|---|---|---|---|---|---|
| Target | 94.76 | 95.23 | 0.17 | 0.21 | 0.00 | positive |
| OT1 | 0.09 | 0.48 | 0.02 | 0.36 | 0.00 | negative |
| OT2 | 0.05 | 0.37 | 0.02 | 0.39 | 0.43 | maybe |
| OT3 | 0.03 | 0.28 | 0.03 | 0.19 | 1.00 | negative |
| OT4 | 0.02 | 0.18 | 0.01 | 0.15 | 1.00 | negative |
| OT5 | 0.01 | 0.09 | 0.03 | 0.11 | 1.00 | negative |
| OT6 | 0.09 | 0.42 | 0.03 | 0.41 | 0.00 | negative |
| OT7 | 1.02 | 17.40 | 2.35 | 19.23 | 1.00 | negative |
| OT8 | 0.07 | 0.71 | 0.04 | 0.58 | 1.00 | negative |
| OT9 | 0.02 | 0.21 | 0.05 | 0.20 | 1.00 | negative |
| OT10 | 0.03 | 0.25 | 0.02 | 0.18 | 1.00 | negative |

TABLE 10D

Off target analysis for 72748/68957 pair

| 72748/68957 | ZFP corrected | raw | GFP corrected | raw | p-value | curation |
|---|---|---|---|---|---|---|
| Target | 93.39 | 93.50 | 0.16 | 0.20 | 0.00 | positive |
| OT1 | 0.05 | 0.30 | 0.02 | 0.24 | 0.69 | negative |
| OT2 | 0.02 | 0.14 | 0.02 | 0.14 | 1.00 | negative |
| OT3 | 0.05 | 2.24 | 0.04 | 2.29 | 1.00 | negative |
| OT4 | 0.02 | 0.33 | 0.03 | 0.31 | 1.00 | negative |
| OT5 | 0.05 | 7.57 | 0.07 | 7.21 | 1.00 | negative |
| OT6 | 0.03 | 1.03 | 0.03 | 1.03 | 1.00 | negative |
| OT7 | 0.76 | 1.86 | 0.59 | 1.79 | 1.00 | negative |
| OT8 | 0.02 | 0.14 | 0.02 | 0.13 | 1.00 | negative |
| OT9 | 0.03 | 0.23 | 0.03 | 0.29 | 1.00 | negative |
| OT10 | 0.33 | 94.52 | 0.29 | 94.49 | 1.00 | negative |

The modified TRAC- and B2M-specific ZFNs were tested in combination and evaluated for knock out efficiency, both by Miseq analysis and by phenotypic analysis analyzing the amount of CD3+ or HLA+ cells by FACs analysis. The analysis was done in T cells, using two different concentrations of added ZFN-encoding mRNA (90 µg/mL or 120 µg/mL). The results are shown below in Table 11 and demonstrate that these reagents are highly efficient.

TABLE 11

TRAC/B2M cleavage

| ZFN reagents (2A-mRNAs) | | Phenotypic screen | | Miseq analysis | |
|---|---|---|---|---|---|
| 68846-2A-53853 (TRAC) µg/mL | 72732-2A-72678 (B2M) µg/mL | % CD3- neg | % HLA-I- neg | % TRAC indels | % B2M indels |
| 0 | 30 | — | 86 | — | 95 |
| 60 | 0 | 98 | — | 92 | — |
| 90 | 90 | 95 | 86 | 90 | 95 |
| 120 | 90 | 94 | 86 | 90 | 94 |
| 90 | 120 | 94 | 86 | 90 | 95 |
| 120 | 120 | 95 | 87 | 91 | 95 |

The reagents were also tested in combination in the presence or absence of a GFP donor construct driven by a PGK promoter. The results are shown in Table 12 where the insertion was done either into the cleaved B2M or TRAC locus. In each case, the PGK-GFP donor was delivered by AAV6 and comprised homology arms with homology flanking either the TRAC or B2M cut sites. The TRAC-specific ZFN pair construct used was 68846-2A-53853 while the construct for the B2M specific pair was 72732-2A-72678.

TABLE 12

Activity of double knock out in two T cell donors.

| | T cell donor #1 | | | T cell donor #2 | |
|---|---|---|---|---|---|
| Sample | Targeted locus | % indel | Sample | Targeted locus | % indel |
| Mock | B2M | 0.3 | Mock | B2M | 0.04 |
| TRAC + B2M | B2M | 84.14 | TRAC + B2M | B2M | 75.33 |
| TRAC + B2M PGK-GFP | B2M | 83.55 | TRAC + B2M PGK-GFP | B2M | 80.96 |
| Mock | TRAC | 0.08 | Mock | TRAC | 0.38 |
| TRAC + B2M | TRAC | 88.05 | TRAC + B2M | TRAC | 85.09 |
| TRAC + B2M PGK-GFP | TRAC | 78.94 | TRAC + B2M PGK-GFP | TRAC | 74.54 |

Thus, optimized pairs of ZFNs specific for B2M were constructed by choosing a FokI variant (see above) in combination with a ZFP DNA binding domain.

The optimized amino acid sequences for the DNA binding domain for the B2M ZFNs 72732 and 72678 are shown below:

72732 N term:
(SEQ ID NO: 175)
RPFQCRICMRNFSRSDDLSKHIRTHTGEKPFACDICGRKFADSSARKKHT

KIHTGEKPFQCRICMRNFSDRSNLSRHIRTHTGEKPFACDICGRKFAQRT

HLRDHTKIHTHPRAPIPKPFQCRICMRNFSQSGHLARHIRTHTGEKPFAC

DICGRKFADSSNREAHTKIH

72678 C-term:
(SEQ ID NO: 176)
RPFQCRICMRKFAAQCCLFHHTKIHTGEKPFQCRICMRNFSDQSNLRAHI

RTHTGEKPFACDICGRKFARSANLTRHTKIHTHPRAPIPKPFQCRICMRN

FSRSDDLTRHIRTHTGEKPFACDICGRKFAQSGSLTRHTKIH

Additional ZFNs comprising the modified ZFPs of the ZFNs described herein (e.g., SEQ ID NO: 175 and SEQ ID NO: 176) are also generated using different FokI and/or linker domains.

Similarly, the optimized pairs of ZFNs specific for TRAC were constructed by choosing a FokI variant (see for example above) in combination with a ZFP DNA binding domain. The optimized amino acid sequences for the DNA binding domain for the B2M ZFNs 68846 and 53853 are shown below:

68846 C-term:
(SEQ ID NO: 177)
RPFQCRICMQNFSQSSDLSRHIRTHTGEKPFACDICGRKFAQSGNRTTHT

KIHTHPRAPIPKPFQCRICMQNFSRSANLARHIRTHTGEKPFACDICGRK

FADRSALARHTKIHTGSQKPFQCRICMQNFSRSDVLSEHIRTHTGEKPFA

CDICGRKFAKHSTRRVHTKIH

53853 N-term:
SEQ ID NO: 178)
RPFQCRICMRNFSTMHQRVEHIRTHTGEKPFACDICGRKFATSGHLSRHT

KIHTGSQKPFQCRICMRNFSRSDHLTQHIRTHTGEKPFACDICGRKFADS

ANLSRHTKIHTHPRAPIPKPFQCRICMRNFSQSGSLTRHIRTHTGEKPFA

CDICGRKFAAKWNLDAHTKIH.

The ZFNs may be assembled with the DNA binding domain N terminal to the FokI domain, wherein the linker sequence between the DNA binding domain and the FokI domain was the L0 linker: LRGS (SEQ ID NO:190). Alternatively, if the ZFN is assembled such that the FokI domain is N-terminal to the DNA binding domain, the linker used was the N7c linker: SGAIRCHDEFWF (SEQ ID NO:179).

Additional features were added into the constructs including a 3× FLAG TAG in the N-terminus region (DYKDHDGDYKDHDIDYKDDDDK, SEQ ID NO:180), and a nuclear localization sequence (PKKKRKV, SEQ ID NO:181).

In addition, in some constructs, sequences encoding the ZFN pair of interest are linked together in one DNA sequence where the open reading frames for each ZFN partner are separated by a 2A sequence. Such a DNA sequence, for the 68846-2A-53853 is shown below:

(SEQ ID NO: 182)
5'ATGGACTACAAAGACCATGACGGTGATTATAAAGATCATGACATC

GATTACAAGGATGACGATGACAAGATGGCCCCCAAGAAGAAGAGGAAGGT

CGGCATCCACGGGGTACCCGCCGCTATGGGACAGCTGGTGAAGAGCGAGC

TGGAGGAGAAGAAGTCCGAGCTGCGGCACAAGCTGAAGTACGTGCCCCAC

GAGTACATCGAGCTGATCGAGATCGCCAGGAACAGCACCCAGGACCGCAT

CCTGGAGATGAAGGTGATGGAGTTCTTCATGAAGGTGTACGGCTACAGGG

GAAAGCACCTGGGCGGAAGCAGAAAGCCTGACGGCGCCATCTATACAGTG

GGCAGCCCCATCGATTACGGCGTGATCGTGGACACAAAGGCCTACAGCGG

CGGCTACAATCTGCCTACCGGCCAGGCCGACGAGATGGAGAGATACGTGG

AGGAGAACCAGACCCGGGATAAGCACCTCAACCCCAACGAGTGGTGGAAG

GTGTACCCTAGCAGCGTGACCGAGTTCAAGTTCCTGTTCGTGAGCGGCCA

CTTCAAGGGCAACTACAAGGCCCAGCTGACCAGGCTGAACCACATCACCA

ACTGCAATGGCGCCGTGCTGAGCGTGGAGGAGCTGCTGATCGGCGGCGAG

-continued
ATGATCAAAGCCGGCACCCTGACACTGGAGGAGGTGCGGCGCAAGTTCAA

CAACGGCGAGATCAACTTCAGCGGCGCCATCAGATGCCACGACGAGTTCT

GGTTCAGGCCCTTCCAGTGTCGAATCTGCATGCAGAACTTCAGTCAGTCC

TCCGACCTGTCCCGCCACATCCGCACCCACACCGGCGAGAAGCCTTTTGC

CTGTGACATTTGTGGGAGGAAATTTGCCCAGTCCGGCAACCGCACCACCC

ATACCAAGATACACACGCATCCCAGGGCACCTATTCCCAAGCCCTTCCAG

TGTCGAATCTGCATGCAGAACTTCAGTCGCTCCGCCAACCTGGCCCGCCA

CATCCGCACCCACACCGGCGAGAAGCCTTTTGCCTGTGACATTTGTGGGA

GGAAATTTGCCGACCGCTCCGCCCTGGCCCGCCATACCAAGATACACACG

GGATCTCAGAAGCCCTTCCAGTGTCGAATCTGCATGCAGAACTTCAGTCG

CTCCGACGTGCTGTCCGAGCACATCCGCACCCACACCGGCGAGAAGCCTT

TTGCCTGTGACATTTGTGGGAGGAAATTTGCCAAGCACTCCACCCGCCGC

GTGCATACCAAGATACACCTGCGGCAGAAGGACAGATCTGGCGGCGGAGA

GGGCAGAGGAAGTCTTCTAACCTGCGGTGACGTGGAGGAGAATCCCGGCC

CTAGGACCATGGACTACAAAGACCATGACGGTGATTATAAAGATCATGAC

ATCGATTACAAGGATGACGATGACAAGATGGCCCCCAAGAAGAAGAGGAA

GGTCGGCATTCATGGGGTACCCGCCGCTATGGCTGAGAGGCCCTTCCAGT

GTCGAATCTGCATGCGTAACTTCAGTACCATGCACCAGCGCGTGGAGCAC

ATCCGCACCCACACCGGCGAGAAGCCTTTCGCCTGTGACATTTGTGGGAG

GAAATTTGCCACCTCCGGCCACCTGTCCCGCCATACCAAGATACACACGG

GCAGCCAAAAGCCCTTCCAGTGTCGAATCTGCATGCGTAACTTCAGTCGC

TCCGACCACCTGACCCAGCACATCCGCACCCACACCGGCGAGAAGCCTTT

TGCCTGTGACATTTGTGGGAGGAAATTTGCCGACTCCGCCAACCTGTCCC

GCCATACCAAGATACACACGCACCCGCGCGCCCCGATCCCGAAGCCCTTC

CAGTGTCGAATCTGCATGCGTAACTTCAGTCAGTCCGGCTCCCTGACCCG

CCACATCCGCACCCACACCGGCGAGAAGCCTTTTGCCTGTGACATTTGTG

GGAGGAAATTTGCCGCCAAGTGGAACCTGGACGCCCATACCAAGATACAC

CTGCGGGGATCCCAGCTGGTGAAGAGCGAGCTGGAGGAGAAGAAGTCCGA

GCTGCGGCACAAGCTGAAGTACGTGCCCCACGAGTACATCGAGCTGATCG

AGATCGCCAGGAACAGCACCCAGGACCGCATCCTGGAGATGAAGGTGATG

GAGTTCTTCATGAAGGTGTACGGCTACAGGGGAAAGCACCTGGGCGGAAG

CAGAAAGCCTGACGGCGCCATCTATACAGTGGGCAGCCCCATCGATTACG

GCGTGATCGTGGACACAAAGGCCTACAGCGGCGGCTACAATCTGCCTATC

GGCCAGGCCGACGAGATGCAGAGATACGTGAAGGAGAACCAGACCCGGAA

TAAGCACATCAACCCCAACGAGTGGTGGAAGGTGTACCCTAGCAGCGTGA

CCGAGTTCAAGTTCCTGTTCGTGAGCGGCCACTTCAAGGGCAACTACAAG

GCCCAGCTGACCAGGCTGAACCGCAAAACCAACTGCAATGGCGCCGTGCT

GAGCGTGGAGGAGCTGCTGATCGGCGGCGAGATGATCAAAGCCGGCACCC

TGACACTGGAGGAGGTGCGGCGCAAGTTCAACAACGGCGAGATCAACTTC

TGATAA.

The amino acid sequence of the 68846-2A-53853 open reading frame is:

(SEQ ID NO: 183)

| Sequence | Positions |
|---|---|
| MDYKDHDGDY KDHDIDYKDD DDKMAPKKKR KVGIHGVPAA MGQLVKSELE EKKSELRHKL | 1-60 |
| KYVPHEYIEL IEIARNSTQD RILEMKVMEF FMKVYGYRGK HLGGSRKPDG AIYTVGSPID | 61-120 |
| YGVIVDTKAY SGGYNLPTGQ ADEMERYVEE NQTRDKHLNP NEWWKVYPSS VTEFKFLFVS | 121-180 |
| GHFKGNYKAQ LTRLNHITNC NGAVLSVEEL LIGGEMIKAG TLTLEEVRRK FNNGEINF*SG* | 181-240 |
| *AIRCHDEFWF* RPFQCRICMQ NFSQSSDLSR HIRTHTGEKP FACDICGRKF AQSGNRTTHT | 241-300 |
| KIHTHPRAPI PKPFQCRICM QNFSRSANLA RHIRTHTGEK PFACDICGRK FADRSALARH | 301-360 |
| TKIHTGSOKP FQCRICMQNF SRSDVLSEHI RTHTGEKPFA CDICGRKFAK HSTRRVHTKI | 361-420 |
| HLRQKDRSGG GEGRGSLLTC GDVEENPGPR TMDYKDHDGD YKDHDIDYKD DDDKMAPKKK | 421-480 |
| RKVGIHGVPA AMAERPFQCR ICMRNFSTMH QRVEHIRTHT GEKPFACDIC GRKFATSGHL | 481-540 |
| SRHTKIHTGS QKPFQCRICM RNFSRSDHLT QHIRTHTGEK PFACDICGRK FADSANLSRH | 541-600 |
| TKIHTHPRAP IPKPFQCRIC MRNFSQSGSL TRHIRTHTGE KPFACDICGR KFAAKWNLDA | 601-660 |
| HTKIH*LRGSQ* LVKSELEEKK SELRHKLKYV PHEYIELIEI ARNSTQDRIL EMKVMEFFMK | 661-720 |
| VYGYRGKHLG GSRKPDGAIY TVGSPIDYGV IVDTKAYSGG YNLPIGQADE MQRYVKENQT | 721-780 |
| RNKHINPNEW WKVYPSSVTE FKFLFVSGHF KGNYKAQLTR LNRKTNCNGA VLSVEELLIG | 781-840 |
| GEMIKAGTLT LEEVRRKFNN GEINF | 841-865 |

The features of this polypeptide are broken out below in Table 13.

TABLE 13

Features of 68846-2A-53853 peptide sequence

| Feature | Designation | Location (within SEQ ID NO: 183) |
|---|---|---|
| 3x FLAG sequence | xx | 2-23 |
| Nuclear localization sequence | xx | 26-32 |
| ELD I479T FokI domain | xx | 43-238 |
| N7c linker | xx | 239-250 |
| 68846 DNA binding domain | xx | 251-421 |

TABLE 13-continued

Features of 68846-2A-53853 peptide sequence

| Feature | Designation | Location (within SEQ ID NO: 183) |
|---|---|---|
| 2A Linker | xx | 432-449 |
| 3x FLAG sequence | xx | 452-474 |
| Nuclear localization sequence | xx | 477-483 |
| 53853 DNA binding domain | xx | 495-665 |
| L0 linker | xx | 666-669 |
| KKR FokI domain | xx | 670-865 |

The sequence for the 72732-2A-72678 opening reading frame is shown below:

(SEQ ID NO: 184)
```
ATGGACTACA AAGACCATGA CGGTGATTAT AAAGATCATG ACATCGATTA CAAGGATGAC
GATGACAAGA TGGCCCCCAA GAAGAAGAGG AAGGTCGGCA TCCACGGGGT ACCCGCCGCT
ATGGCTGAGA GGCCCTTCCA GTGTCGAATC TGCATGCGTA ACTTCAGTCG TAGTGACGAC
CTGAGCAAGC ACATCCGCAC CCACACAGGG GAGAAGCCTT TTGCCTGTGA CATTTGTGGG
AGGAAATTTG CCGACAGCAG CGCCCGCAAA AGCATACCA AGATACACAC GGGCGAGAAG
CCCTTCCAGT GTCGAATCTG CATGCGTAAC TTCAGTGACC GCTCCAACCT GTCCCGCCAC
ATCCGCACCC ACACCGGCGA GAAGCCTTTT GCCTGTGACA TTTGTGGGAG GAAATTTGCC
CAGCGCACCC ACCTGCGCGA CCATACCAAG ATACACACGC ACCCGCGCGC CCCGATCCCG
AAGCCCTTCC AGTGTCGAAT CTGCATGCGT AACTTCAGTC AGTCCGGCCA CCTGGCCCGC
CACATCCGCA CCCACACCGG CGAGAAGCCT TTTGCCTGTG ACATTTGTGG GAGGAAATTT
GCCGACTCCT CCAACCGCGA GGCCCATACC AAGATACACC TGCGGGGATC CCAGCTGGTG
AAGAGCGAGC TGGAGGAGAA GAAGTCCGAG CTGCGCACA AGCTGAAGTA CGTGCCCCAC
GAGTACATCG AGCTGATCGA GATCGCCAGG AACAGCACCC AGGACCGCAT CCTGGAGATG
```

-continued

```
AAGGTGATGG AGTTCTTCAT GAAGGTGTAC GGCTACAGGG GAAAGCACCT GGGCGGAAGC

AGAAAGCCTG ACGGCGCCAT CTATACAGTG GGCAGCCCCA TCGATTACGG CGTGATCGTG

GACACAAAGG CCTACAGCGG CGGCTACAAT CTGGACATCG GCCAGGCCGA CGAGATGGAG

AGATACGTGG AGGAGAACCA GACCCGGGAT AAGCACCTCA ACCCCAACGA GTGGTGGAAG

GTGTACCCTA GCAGCGTGAC CGAGTTCAAG TTCCTGTTCG TGAGCGGCCA CTTCAAGGGC

AACTACAAGG CCCAGCTGAC CAGGCTGAAC CACATCACCA ACTGCAATGG CGCCGTGCTG

AGCGTGGAGG AGCTGCTGAT CGGCGGCGAG ATGATCAAAG CCGGCACCCT GACACTGGAG

GAGGTGCGGC GCAAGTTCAA CAACGGCGAG ATCAACTTCA GATCTGGCGG CGGAGAGGGC

AGAGGAAGTC TTCTAACCTG CGGTGACGTG GAGGAGAATC CCGGCCCTAG GACCATGGAC

TACAAAGACC ATGACGGTGA TTATAAAGAT CATGACATCG ATTACAAGGA TGACGATGAC

AAGATGGCCC CCAAGAAGAA GAGGAAGGTC GGCATTCATG GGGTACCCGC CGCTATGGGA

CAGCTGGTGA AGAGCGAGCT GGAGGAGAAG AAGTCCGAGC TGCGGCACAA GCTGAAGTAC

GTGCCCCACG AGTACATCGA GCTGATCGAG ATCGCCTACA ACAGCACCCA GGACCGCATC

CTGGAGATGA AGGTGATGGA GTTCTTCATG AAGGTGTACG GCTACAGGGG AAAGCACCTG

GGCGGAAGCA GAAAGCCTGA CGGCGCCATC TATACAGTGG GCAGCCCCAT CGATTACGGC

GTGATCGTGG ACACAAAGGC CTACAGCGGC GGCTACAATC TGCCTATCGG CCAGGCCGAC

GAGATGCAGA GATACGTGAA GGAGAACCAG ACCCGGAATA AGCACATCAA CCCCAACGAG

TGGTGGAAGG TGTACCCTAG CAGCGTGACC GAGTTCAAGT TCCTGTTCGT GAGCGGCCAC

TTCAAGGGCA ACTACAAGGC CCAGCTGACC AGGCTGAACC GCAAAACCAA CTGCAATGGC

GCCGTGCTGA GCGTGGAGGA GCTGCTGATC GGCGGCGAGA TGATCAAAGC CGGCACCCTG

ACACTGGAGG AGGTGCGGCG CAAGTTCAAC AACGGCGAGA TCAACTTCAG CGGCGCTCAG

GGATCTACCC TGGACTTTAG GCCCTTCCAG TGTCGAATCT GCATGCGTAA GTTTGCCGCC

CAGTGTTGTC TGTTCCACCA TACCAAGATA CACACGGGCG AGAAGCCCTT CCAGTGTCGA

ATCTGCATGC GTAACTTCAG TGACCAGTCC AACCTGCGCG CCCACATCCG CACCCACACC

GGCGAGAAGC CTTTTGCCTG TGACATTTGT GGGAGGAAAT TTGCCCGCTC CGCCAACCTG

ACCCGCCATA CCAAGATACA CACGCACCCG CGCGCCCCGA TCCCGAAGCC CTTCCAGTGT

CGAATCTGCA TGCGTAACTT CAGTCGCTCC GACGACCTGA CCCGCCACAT CCGCACCCAC

ACCGGCGAGA AGCCTTTTGC CTGTGACATT TGTGGGAGGA AATTTGCCCA GTCCGGCTCC

CTGACCCGCC ATACCAAGAT ACACCTGCGG CAGAAGGACT GATAA
```

The amino acid sequence of the 72732-2A-72678 open reading is shown below.

(SEQ ID NO: 185)
```
MDYKDHDGDY KDHDIDYKDD DDKMAPKKKR KVGIHGVPAA MAERPFQCRI CMRNFSRSDD   1-60

LSKHIRTHTG EKPFACDICG RKFADSSARK KHTKIHTGEK PFQCRICMRN FSDRSNLSRH   61-120

IRTHTGEKPF ACDICGRKFA QRTHLRDHTK IHTHPRAPIP KPFQCRICMR NFSQSGHLAR   121-180

HIRTHTGEKP FACDICGRKF ADSSNREAHT KIHLRGSQLV KSELEEKKSE LRHKLKYVPH   181-240

EYIELIEIAR NSTQDRILEM KVMEFFMKVY GYRGKHLGGS RKPDGAIYTV GSPIDYGVIV   241-300

DTKAYSGGYN LDIGQADEME RYVEENQTRD KHLNPNEWWK VYPSSVTEFK FLFVSGHFKG   301-360

NYKAQLTRLN HITNCNGAVL SVEELLIGGE MIKAGTLTLE EVRRKFNNGE INFRSGGGEG   361-420
```

```
RGSLLTCGDV EENPGPRTMD YKDHDGDYKD HDIDYKDDDD KMAPKKKRKV GIHGVPAAMG    421-480

QLVKSELEEK KSELRHKLKY VPHEYIELIE IAYNSTQDRI LEMKVMEFFM KVYGYRGKHL    481-540

GGSRKPDGAI YTVGSPIDYG VIVDTKAYSG GYNLPIGQAD EMQRYVKENQ TRNKHINPNE    541-600

WWKVYPSSVT EFKFLFVSGH FKGNYKAQLT RLNRKTNCNG AVLSVEELLI GGEMIKAGTL    601-660

TLEEVRRKFN NGEINFSGAQ GSTLDFRPFQ CRICMRKFAA QCCLFHHTKI HTGEKPFQCR    661-720

ICMRNFSDQS NLRAHIRTHT GEKPFACDIC GRKFARSANL TRHTKIHTHP RAPIPKPFQC    721-780

RICMRNFSRS DDLTRHIRTH TGEKPFACDI CGRKFAQSGS LTRHTKIHLR QKD           781-833
```

The features of the 72732-2A-72678 amino acid sequence are shown below in Table 14.

TABLE 14

Features of the 72732-2A-72678 amino acid sequence

| Feature | Designation | Location (within SEQ ID NO: 185) |
|---|---|---|
| 3x FLAG sequence | xx | 2-23 |
| Nuclear localization sequence | xx | 26-32 |
| 72732 DNA binding domain | xx | 44-213 |
| L0 linker | xx | 214-217 |
| ELD P478D FokI domain | xx | 218-413 |
| 2A Linker | xx | 419-436 |
| 3x FLAG sequence | xx | 440-461 |
| Nuclear localization sequence | xx | 464-470 |
| KKR R416Y FokI domain | xx | 481-676 |
| N6alinker | xx | 677-686 |
| 72678 DNA binding domain | xx | 687-828 |

Example 6: In Vivo Testing of ZFN Reagents

T cells as described herein are administered to animal models of graft vs. host disease and/or cancer (e.g., nude mice injected with cancer cell lines such as multiple myeloma to establish tumor models). For example, activated human T cells are electroporated with mRNAs encoding the B2M- and TRAC-specific ZFNs where each pair is encoded by a single mRNA separated by a sequence encoding a 2A self-cleaving peptide (MacLeod, et al. (2017) *Mol Ther.* 25(4):949-961). The cells are also transduced with AAV particles comprising a CAR donor (e.g., CD19 CAR). The cells are then cultured and stained for CAR expression and a lack of CD3+ cells. Any residual CD3+ cells are depleted by magnetic separation. NSG mice are injected intravenously with firefly luciferase expressing Raji cells (Raji-ffLuc) and, after four days, are injected with the CD3-/anti-CD19 CAR T cells. Engraftment and growth of the Raji-ffLuc cells is evident by day four post injection and increases significantly in untreated mice. Peak CAR T cell frequencies in the blood of treated mice are observed on day 8, reaching ~10% of cells in peripheral blood in the high-dose group. By days 17-19, all mice in control groups show evidence of significant tumor burden, especially in the spine and bone marrow, resulting in complete hindlimb paralysis, and are euthanized. In contrast, all groups of mice treated with anti-CD19 CAR T cells show no evidence of tumor growth by day 11 and, remained tumor-free through day 32 of the study.

No or minimal residual disease is detected in tissue of animals (e.g., bone marrow, spleen, lungs, liver, heart, etc.) receiving T cells as described herein. By contrast, control subjects have detectable tumor cells in most tissues.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing description and examples should not be construed as limiting.

What is claimed is:

1. A zinc finger nuclease (ZFN) comprising a FokI cleavage domain and a zinc finger protein (ZFP) that binds to a target site in a mammalian β2 microglobulin (B2M) gene, wherein the ZFN comprises a pair of ZFPs from ZFNs selected from: a ZFN designated 57531 and a ZFN designated 72732; a ZFN designated 57531 and a ZFN designated 72748; a ZFN designated 68957 and a ZFN designated 57071; a ZFN designated 68957 and a ZFN designated 72732; a ZFN designated 68957 and a ZFN designated 72748: a ZFN designated 72678 and a ZFN designated 57071; a ZFN designated 72678 and a ZFN designated 72732; or a ZFN designated 72678 and a ZFN designated 72748, wherein
   (i) the ZFP from the ZFN designated 57531 comprises 5 zinc finger domains ordered F1 to F5, the zinc finger domains comprising the following recognition helix regions:
   FL: AQCCLFH (SEQ ID NO:128):
   F2: DQSNLRA (SEQ ID NO:42):
   F3: RSANLTR (SEQ ID NO: 129);
   F4: RSDDLTR (SEQ ID NO: 130); and
   F5: QSGSLTR (SEQ ID NO:66); and
   (ii)) the ZFP from the ZFN designated 57071 comprises 6 zinc finger domains ordered F1 to F6, the zinc finger domains comprising the following recognition helix regions:
   FL: RSDDLSK (SEQ ID NO:131):
   F2: DSSARKK (SEQ ID NO:132):
   F3: DRSNLSR (SEQ ID NO:22),
   F4: QRTHLRD (SEQ ID NO:133);
   F5: QSGHLAR (SEQ ID NO:29);
   F6: DSSNREA (SEQ ID NO:134).

2. The zinc finger nuclease of claim 1 the first ZFP comprising amino acid residues 687-828 of SEQ ID NO:185 and the second ZFP comprising amino acid residues 44-213 of SEQ ID NO:185.

3. An isolated cell comprising the zinc finger nuclease of claim 1, wherein the genome of the cell is modified by the zinc finger nuclease.

4. The cell of claim 3, wherein the cell is a stem cell or a precursor cell.

5. The cell of claim 4, wherein the cell is a human cell.

6. The cell of claim 3, wherein the genomic modification is selected from the group consisting of insertions, deletions and combinations thereof.

7. The cell of claim 3, further comprising one or more additional genomic modifications.

8. The cell of claim 7, wherein the one or more_additional genomic modifications comprise modification of a T cell receptor (TCR) gene, modification of an HLA-A gene, modification of an HLA-B gene, modification of an HLA-C gene, modification of a TAP gene, modification of a CTLA-4 gene, modification of a PD1 gene, modification of a CISH gene, modification of a tet-2 gene, and/or insertion of a transgene into the genome.

9. The cell of claim 8, wherein the transgene encodes at least one chimeric antigen receptor (CAR).

10. The cell of claim 9, wherein the cell is an effector T cell or a regulatory T cell.

11. A pharmaceutical composition comprising the cell of claim 4 and further comprising genetically modified cells descended therefrom.

12. The pharmaceutical composition of claim 11, wherein the genetically modified cells are effector T cells or regulatory T cells.

* * * * *

UNITED STATES PATENT AND TRADEMARK OFFICE
CERTIFICATE OF CORRECTION

PATENT NO. : 11,512,287 B2
APPLICATION NO. : 16/009975
DATED : November 29, 2022
INVENTOR(S) : Anthony Conway et al.

Page 1 of 1

It is certified that error appears in the above-identified patent and that said Letters Patent is hereby corrected as shown below:

In the Claims

Column 209, Claim 1, Line 47 should read:
F1:     AQCCLFH (SEQ ID NO:128);

Column 209, Claim 1, Line 56 should read:
F1:     RSDDLSK (SEQ ID NO:131);

Column 210, Claim 11, Line 57 should read:
claim 3 and further comprising genetically modified cells Signed and Sealed this
Twenty-fourth Day of January, 2023

Katherine Kelly Vidal
*Director of the United States Patent and Trademark Office*